United States Patent [19]

DeHaven-Hudkins et al.

[11] Patent Number: 5,380,729
[45] Date of Patent: Jan. 10, 1995

[54] 12-HETERO SUBSTITUTED 6,11-ETHANO-6,11-DIHYDROBENZO (B) QUINOLIZINIUM SALTS AND COMPOSITIONS AND METHOD OF USE THEREOF

[75] Inventors: Diane L. DeHaven-Hudkins, West Pikeland Township, Chester County; William G. Earley, Lower Providence Township, Montgomery County; Virendra Kumar, Tredyffrin Township, Chester County; John P. Mallamo, Uwchlan Township, Chester County; Matthew S. Miller, Lower Makefield Township, Bucks County, all of Pa.

[73] Assignee: Sterling Winthrop Inc., New York, N.Y.

[21] Appl. No.: 122,039

[22] Filed: Sep. 14, 1993

[51] Int. Cl.$^6$ .................. A61K 31/435; A61K 31/44; C07D 521/00; C07D 471/00
[52] U.S. Cl. .................. 514/284; 514/285; 514/294; 514/306; 546/71; 546/73; 546/93; 546/94; 546/95
[58] Field of Search .................. 546/73, 93, 94, 95; 514/306, 294, 285, 284

[56] References Cited

U.S. PATENT DOCUMENTS

| | | | |
|---|---|---|---|
| 3,408,352 | 10/1968 | Hardtmann | 546/94 |
| 3,517,073 | 6/1970 | Fields | 546/76 |
| 3,565,899 | 2/1971 | Doebbl et al. | 546/94 |

FOREIGN PATENT DOCUMENTS

| | | | |
|---|---|---|---|
| 5439097 | 3/1976 | Japan | 546/94 |

OTHER PUBLICATIONS

Fields, et al., I J. Org. Chem. 1968, 33(1), 390–395.
Fields et al III, J. Org. Chem. 1971, 36(20), 2986–2990.
Fields et al IV, J. Org. Chem. 1971, 36(20), 2991–2994.
Fields, II J. Org. Chem. 1971, 36(20), 3002–3005.
Westerman and Bradsher, J. Org. Chem. 1971, 36(7), 969–970.
Bradsher and Day, J. Org. Chem. 1973, 10, 1031–1033.
Fields et al II, J. Org. Chem. 1970, 35(6), 1870–1875.
Fields et al. V, J. Org. Chem. 1971, 36(20), 2995–3001.
Fields et al. VI, J. Het. Chem. 1970, 7, 91–97.
Bradsher et al II, J. Org. Chem. 1968, 33(2), 519–523.
Bradsher et al I, J. Am. Chem. Soc. 1958, 80, 933–934.
Bradsher et al III, J. Org. Chem. 1969, 34(6), 1700–1702.
Burnham et al IV, J. Org. Chem. 1972, 37(3), 355–358.
Parham et al., J. Org. Chem. 1972, 37(3), 358–362.
Bradsher et al V, J. Am. Chem. Soc. 1977, 99(8), 2588–2591.
Bradsher et al. VI, J. Org. Chem. 1978, 43(5), 822–827.
Westerman et al I, J. Org. Chem. 1978, 43(15), 3002–3006.
Westerman et al. II, J. Org. Chem. 1979, 44(5), 727–733.
Bradsher et al., VII J. Org. Chem. 1979, 44(8), 1199–1201.
Hart et al., Tetrahedron Letters 1975, 52, 4639–4642.

*Primary Examiner*—Floyd D. Higel
*Attorney, Agent, or Firm*—Michael D. Alexander; Paul E. Dupont

[57] ABSTRACT

1-Hetero substituted 6,11-ethano-6,11-dihydrobenzo[b-]quinolizinium salts, pharmaceutical compositions containing them, and methods for the treatment or prevention of neurodegenerative disorders or neurotoxic injuries utilizing them.

49 Claims, No Drawings

12-HETERO SUBSTITUTED 6,11-ETHANO-6,11-DIHYDROBENZO (B) QUINOLIZINIUM SALTS AND COMPOSITIONS AND METHOD OF USE THEREOF

BACKGROUND OF THE INVENTION (a) Field of the Invention

The invention relates to 12-hetero substituted 6,11-ethano-6,11-dihydrobenzo [b]quinolizinium salts, to compositions containing the same, to the method of use thereof in the treatment or prevention of neurodegenerative disorders or neurotoxic injuries and to a process for preparing intermediates.

(b) Information Disclosure Statement

Fields, U.S. Pat. No. 3,517,073 issued Jun. 23, 1970, discloses compounds of the formula:

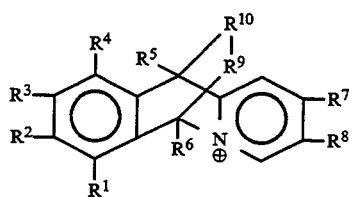

wherein each of $R^1$, $R^2$, $R^3$ and $R^4$ when taken separately, is hydrogen, lower alkyl, lower aryl, lower acyloxy, lower alkoxy, nitro, halogen, lower acylamino, di(lower alkyl) amino; one group of $R^1$ and $R^2$, $R^2$ and $R^3$, and $R^3$ and $R^4$, preferably $R^1$ and $R^2$, and $R^3$ and $R^4$, each group when taken together, represents a fused ring system containing up to three 6- member carbocyclic and nitrogen-containing heterocyclic rings at least one of which is an aromatic ring, and having no more than two nuclear nitrogens in any ring, which may be unsubstituted or substituted with one or more of the substituents defined by $R^1$, $R^2$, $R^3$ and $R^4$; each of $R^5$ and $R^6$, when taken separately is hydrogen, lower alkyl or lower aryl; each of $R^7$ and $R^8$ when taken separately, is hydrogen; $R^7$ and $R^8$, when taken together, represent a fused ring system as defined hereinbefore; $R^9$, when taken individually, is methylene or lower alkyl, lower aryl, lower alkenyl, halogen, or cyano substituted methylene; $R^{10}$, when taken individually, is a protected carbonyl group; $R^9$ and $R^{10}$, when taken together, represent a fused aromatic carbocyclic or heterocyclic ring system, whose valence bonds are from adjacent carbons, containing up to three 6-membered carbocyclic and nitrogen-containing heterocyclic rings having no more than two nitrogens in any ring and which may be substituted with one or more of the substituents defined by $R^1$, $R^2$, $R^3$ and $R^4$. Among the compounds specifically disclosed are 12,12-diethoxy-11-methyl-9,10-ethano-9,10-dihydro-4a-azoniaanthracene perchlorate and 9,10-(O-benzeno)-9,10-dihydro-5-methyl-4a-azoniaanthracene perchlorate. Also disclosed are compounds of the formula:

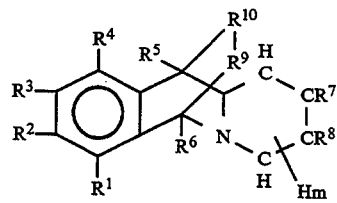

wherein $R^1$–$R^{10}$ are as defined above and m is an odd integer having a value of from 1 to 5, inclusive. Among the compounds specifically disclosed are 12,12-diethoxy-11-methyl-9,10-ethano-4a-aza-1,2,3,4,4a,9,9a,10-octahydroanthracene perchlorate acid salt, 9,10-(O-benzeno)-5-methyl-4a-aza-1,2,3,4,4a,9,9a,10-octahydroanthracene and 12,12-diethoxy-9,10-ethano-11-bromo-4a-aza-1,2,3,4,4a,9,9a,10-octahydroanthracene. The above-described compounds are disclosed as being intermediates in the synthesis of 2-napthol derivatives and various anthracene derivatives.

Fields et al. , J. Org. Chem. 1968, 33 (1), 390–395, disclose a series of sixteen Diels-Alder adducts prepared from a 4a-azoniaanthracene ion and various dienophiles. Among the compounds specifically disclosed are 12-ethyl, 12-hydroxymethyl and 12-ethylene-9,10-dihydro-4a-azonia-9,10-ethanoanthracene bromides; 12-phenyl-12-(4-morpholinyl), 12-methyl-12-(1-methylethylene), 12,12-diethoxy-11-bromo and 12-diethylamino-11-phenyl-9,10-dihydro-4a-azonia-9,10-ethanoanthracene perchlorates, as well as 9, 10[1',2']cyclopentyl and 9,10[2',3']tetrahydropyranyl-9,10-dihydro-4a-azoniaanthracene perchlorates. No utility is disclosed for these compounds.

Fields and Regan, J. Org. Chem. 1971, 36 (20), 2986–2990, disclose compounds of the formula:

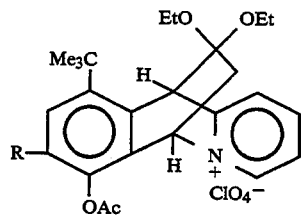

wherein R is H, Br, or OAc, as intermediates in the synthesis of substituted 8-tert-butyl-1-(2-pyridyl)napthalenes. Fields and Regan, J. Org. Chem. 1971, 36(20), 2991–2994, disclose compounds of the formula:

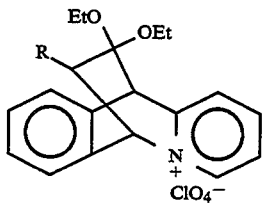

wherein R is H, $CH_3$, $C_6H_5$, or Br, as intermediates in the synthesis of 2-pyridylnapthols. 0 Fields, J. Org. Chem. 1971, 36(20), 3002–3005, discloses a series of substituted 12,12-diethoxy-9,10-ethano-9,10-dihydro-4a-azoniaanthracenes and the corresponding derivatives wherein the pyridinium moiety is partially or completely reduced, as intermediates in the synthesis of substituted 2-napthols. Among the compounds specifically disclosed is 12,12-diethoxy-5,11-dimethyl-9,10-ethano-9,10-dihydro-4a-azoniaanthracene perchlorate. Also disclosed is a series of substituted 9,10-(O-benzeno)-9,10-dihydro-4a-azoniaanthracenes and the corresponding derivatives wherein the pyridinium moiety is partially or completely reduced, as intermediates in the synthesis of substituted anthracenes. Among the compounds specifically disclosed is 9,10-(O-benzeno)-9,10-dihydro-4a-azoniaanthracene perchlorate.

Westerman and Bradsher, J. Org. Chem. 1971, 36(7), 969–970, disclose compounds of the formula:

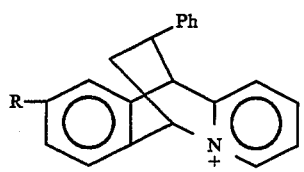

wherein R is $CH_3$, $CH(CH_3)_2$, H, F, I, Cl, Br, $CO_2H$, $CO_2CH_3$, or $NO_2$. No utility is disclosed for these compounds.

Bradsher and Day, J. Het. Chem. 1973, 10, 1031–1033, disclose four Dieis-Alder adducts prepared from acridizinium perchlorate and cyclopentadiene, methyl vinyl ether, norbornadiene and maleic anhydride. No utility is disclosed for these compounds.

Fields and Regan, J. Org. Chem. 1970, 35 (6), 1870–1875, disclose compounds of the formula:

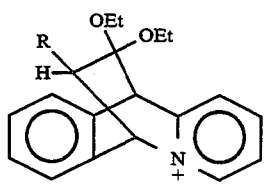

wherein R is H, $CH_3$ or $C_6H_5$. Also specifically disclosed are 9,10-dihydro-12,12-dimethoxy-11,11-dimethyl-4a-azonia-9,10-ethanoanthracene perchlorate and 9,10-dihydro-9,11-dimethyl-12,12-diethoxy-4a-azonia-9,10-ethanoanthracene perchlorate. The compounds are said to be intermediates in the synthesis of 9,10-dihydro-12-oxo-4a-azonia-9,10-ethanoanthracenes.

Fields et al., J. Org. Chem. 1971, 36 (20), 2995–3001, disclose 9,10-dihydro-4a-azonia-9,10-O-benzenoanthracene perchlorate and several analogs as intermediates in the synthesis of various 9- (2-pyridyl) anthracenes.

Fields and Miller, J. Het. Chem. 1970, 7, 91–97, disclose a compound of the formula:

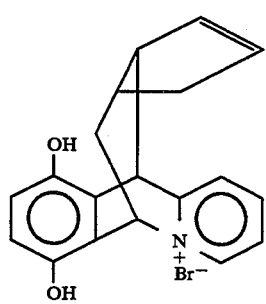

as an intermediate in the synthesis of the corresponding 5,8-dione salt.

Bradsher and Stone, J. Org. Chem. 1968, 33(2), 519–523, disclose a series of Dieis-Alder adducts prepared from an acridizinium ion and maleic anhydride, maleate esters, fumarate esters and various para-substituted styrenes in which the para substituent is H, $CH_3$, $OCH_3$ or $NO_2$. No utility is disclosed for these compounds. A substantially similar disclosure for the preparation of Dieis-Alder adducts from acridizinium bromide and maleic anhydride, maleate or fumarate esters can be found in Bradsher and Solomons, J. Am. Chem. Soc. 1958, 80, 933–934.

Bradsher and Stone, J. Org. Chem. 1969, 34(6), 1700–1702, disclose compounds of the formula:

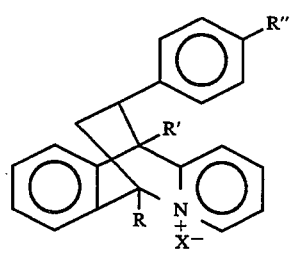

wherein R is H, or $CH_3$; R' is H, or $CH_3$; R" is $OCH_3$, $CH_3$, H, or $NO_2$; and X— is perchlorate; without an indication of utility. Also disclosed are the Dieis-Alder adduces obtained from acridizinium perchlorate and diethyl maleate, diethyl fumarate or dimethyl maleate, without an indication of utility.

Burnham and Bradsher, J. Org. Chem. 1972, 37(3), 355–358, disclose compounds of the formula:

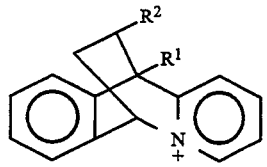

wherein $R^1$ is Ph, and $R^2$ is OEt; or $R^1$ is H, and $R^2$ is OEt, OBu, OAc, N-carbazolyl or 1-pyrrolidin-2-one, without an indication of utility Parham et al., J. Org. Chem. 1972, 37(3), 358–362, disclose compounds of the formula:

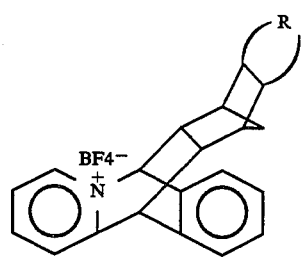

wherein R is $H_2$, $(CH_2)_3$, C(O)NHC(O), $C(O)N(CH_3)$-C(O), C(O)OC(O), $CH_2OCH_2$, or $CH_2NH_2+CH_2$, without an indication of utility.

Bradsher et al., J. Am. Chem. Soc. 1977, 99(8), 2588–2591, disclose compounds of the formula:

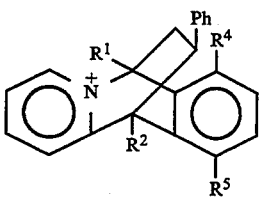

wherein: $R^1=R^2=R^4=R^5=H$; $R^1=Me$, and $R^2=R^4=R^5=H$, $R^1=R^4=R^5=H$, and $R^2=Me$; and $R^1=H$, and $R^2=R^4=R^5=Me$. No utility is disclosed for these compounds.

Bradsher et al., J. Org. Chem. 1978, 43 (5), 822–827, disclose compounds of the formula:

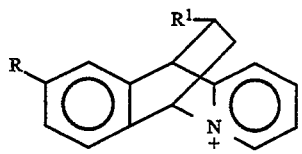

wherein: $R^1$ is OEt and R is Me, H, F, Cl, $CO_2Me$ or $NO_2$; $R^1$ is O-Ph-p-X, wherein X is $CH_3$, $OCH_3$, H, $C(O)CH_3$, or $NO_2$, and R is hydrogen; and $R^1$ is N-carbazolyl and R is hydrogen. No utility is disclosed for these compounds.

Westerman and Bradsher, J. Org. Chem. 1978, 43(15), 3002–3006, disclose a series of Diels-Alder adducts prepared from an acridizinium ion and various unsymmetrical alkenes, without an indication of utility. Among the compounds specifically disclosed are 6,11[2′,3′]indanyl-6,11-dihydroacridizinium tetrafluoroborate, and 12-phenyl-13-(2-pyridyl)-6,11-dihydro-6,11-ethanoacridizinium tetrafluoroborate.

Westerman and Bradsher, J. Org. Chem. 1979, 44 (5), 727–733, disclose a series of Dieis-Alder adducts prepared from a substituted or unsubstituted acridizinium cation and various polarizable alkenes without an indication of utility. Among the compounds specifically disclosed are 12,12-diphenyl-6,11-dihydro-6,11-ethanoacridizinium perchlorate or bromide, 9-methyl-6,11[2′,3′]indanyl-6,11-dihydroacridizinium tetrafluoroborate, and 7,10-dimethyl-12-phenyl-12-(4-morpholinyl), 9-methyl-12-phenyl-12-(4-morpholinyl), 12-(2-pyridyl), and 9-methyl-12-(2-pyridyl)-6,11-dihydro-6,11-ethanoacridizinium tetrafluoroborates.

Bradsher et al., J. Org. Chem. 1979, 44 (8), 1199–1201, disclose a series of Dieis-Alder adducts prepared from a substituted or unsubstituted acridizinium ion and cyclopropene or 1-methylcyclopropene, without an indication of utility.

Hart et al., Tetrahedron Letters 1975, 52, 4639–4642, disclose a compound of the formula:

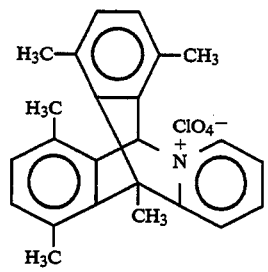

as an intermediate in the synthesis of 1,4,5,8, 9-pentamethylanthracene.

SUMMARY OF THE INVENTION

The invention relates to compounds of the Formula I:

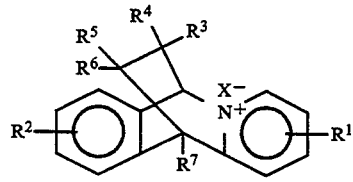

wherein:

$R^1$ is hydrogen, or from one to four, the same or different, substituents in any of the 1-, or 4-positions selected from the group consisting of lower-alkoxy, lower-alkyl, and halogen;

$R^2$ is hydrogen, or from one to four, the same or different, substituents in any of the 7-, 8-, 9-, or 10-positions selected from the group consisting of lower-alkyl, lower-alkanoyloxy, halogen, nitro, hydroxy, lower-alkoxy, methylenedioxy, polyfluorolower-alkyl and polychlorolower-alkyl;

$R^3$ and $R^4$ are the same or different lower-alkyl;

$R^5$ and $R^6$ are independently selected from the group consisting of hydrogen, lower-alkoxy, trilower-alkylsilyloxy and dilower-alkylamino; or $R^5$ and $R^6$ together represent $-O-CHR^8-(CH_2)_nCHR^9-O-$ wherein n is zero or one and $R^8$ and $R^9$ are independently hydrogen, lower-alkyl, or phenyl-lower-alkoxy-lower-alkyl;

$R^7$ is hydrogen, or lower-alkyl; and $X^-$ is an anion;

or a pharmaceutically acceptable acid-addition salt of basic members thereof; or a hydrate thereof; or a stereoisomer thereof; with the proviso that when $R^1$, $R^2$ and $R^7$ are hydrogen, $R^3$ and $R^4$ are methyl and $X^-$ is $ClO_4^-$, $R^5$ and $R^6$ together cannot be $-O-CH(CH_3)CH(CH_3)-O-$; further provided that $R^5$ and $R^6$ cannot both simultaneously be hydrogen; still further provided that when $R^1$, $R^2$ and $R^7$ are hydrogen, $R^3$ and $R^4$ are methyl, and $X^-$ is $ClO_4^-$, $R^5$ and $R^6$ cannot simultaneously be methoxy.

The invention further relates to compounds of the Formula II:

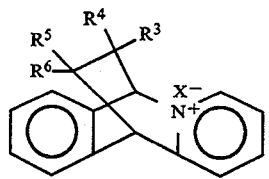

wherein:

$R^3$ and $R^4$ are independently hydrogen, lower-alkoxy, or chlorine;

$R^5$ and $R^6$ are the same or different lower-alkoxy; and $X^-$ is an anion;

or a stereoisomer thereof; with the proviso that $R^3$ and $R^4$ cannot both simultaneously be hydrogen.

The invention further relates to compounds of the Formula III:

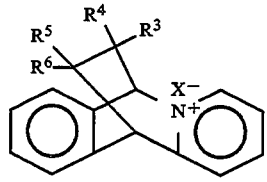

wherein:

$R^3$ and $R^4$ are independently hydrogen, or lower-alkyl;

$R^5$ and $R^6$ are independently hydrogen, or dilower-alkylamino; and $X^-$ is an anion;

or a pharmaceutically acceptable acid-addition salt of basic members thereof; or a stereoisomer thereof; with the proviso that $R^3$ and $R^4$ cannot simultaneously be lower-alkyl; further provided that $R^5$ and $R^6$ cannot simultaneously be hydrogen.

The compounds of the Formulas I, II, and III bind to the PCP receptor and are thus useful in the treatment or prevention of neurodegenerative disorders or neurotoxic injuries.

Preferred compounds of the Formula I above are those wherein:

$R^1$ is hydrogen, 1-lower-alkoxy, or 4-lower-alkyl;

$R^2$ is hydrogen, or from one to two, the same or different, substituents in any of the 7-, 8-, 9-, or 10-positions selected from the group consisting of lower-alkyl, acetoxy, halogen, nitro, hydroxy, lower-alkoxy, methylenedioxy, and trifluoromethyl;

$R^3$ and $R^4$ are the same lower-alkyl; and $R^5$, $R^6$, $R^7$ and $X^-$ have the meanings given above.

Particularly preferred compounds of the Formula I above are those wherein:

$R^1$ is hydrogen, 1-methoxy, or 4-methyl;

$R^2$ is hydrogen, or from one to two, the same or different, substituents in any of the 7-, 8-, 9-, or 10-positions selected from the group consisting of methyl, tert-butyl, acetoxy, bromine, chlorine, fluorine, nitro, hydroxy, methoxy, isopropoxy, methylenedioxy and trifluoromethyl;

$R^3$ and $R^4$ are both methyl or ethyl;

$R^5$ and $R^6$ are independently selected from the group consisting of hydrogen, lower-alkoxy, trimethylsilyloxy, and diethylamino, or $R^5$ and $R^6$ together represent —OCHR$^8$(CH$_2$)$_n$CHR$^9$O— wherein n is zero or one and $R^8$ and $R^9$ are simultaneously hydrogen, lower-alkyl, or phenyl-lower-alkoxy-lower-alkyl;

$R^7$ is hydrogen or methyl; and $X^-$ is an anion.

Preferred compounds of the Formula II above are those wherein $R^3$ and $R^4$ are independently hydrogen, ethoxy, or chlorine; $R^5$ and $R^6$ are the same lower-alkoxy; and $X^-$ is an anion.

Preferred compounds of the Formula III above are those wherein $R^3$ and $R^4$ are independently hydrogen, or methyl; $R^5$ and $R^6$ are independently hydrogen, or diethylamino; and $X^-$ is an anion.

The invention further relates to pharmaceutical compositions which comprise a compound of the Formula I:

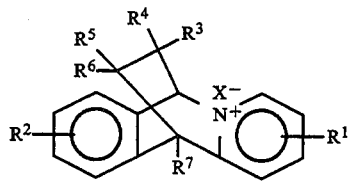

wherein:

$R^1$ is hydrogen, or from one to four, the same or different, substituents in any of the 1-, 2-, 3-, or 4-positions selected from the group consisting of lower-alkoxy, lower-alkyl and halogen;

$R^2$ is hydrogen, or from one to four, the same or different, substituents in any of the 7-, 8-, 9-, or 10-positions selected from the group consisting of lower-alkyl, lower-alkanoyloxy, halogen, nitro, hydroxy, lower-alkoxy, methylenedioxy, polyfluorolower-alkyl, and polychlorolower-alkyl;

$R^3$ and $R^4$ are independently selected from the group consisting of hydrogen, lower-alkoxy, halogen, lower-alkyl, and phenyl;

$R^5$ and $R^6$ are independently selected from the group consisting of hydrogen, lower-alkoxy, trilower-alkylsilyloxy and dilower-alkylamino; or $R^5$ and $R^6$ together represent —O—CHR$^8$(CH$_2$)$_n$CHR$^9$—O— wherein n is zero or one and $R^8$ and $R^9$ are independently hydrogen, lower-alkyl, or phenyl-lower-alkoxy-lower-alkyl;

$R^7$ is hydrogen, or lower-alkyl; and $X^-$ is an anion; or a pharmaceutically acceptable acid-addition salt of basic diluent or vehicle; with the proviso that when $R^1$, $R^3$, $R^4$, and $R^7$ members thereof; or a hydrate thereof; or a stereoisomer thereof; together with a pharmaceutically acceptable carrier, adjuvant, are hydrogen, $R^5$ and $R^6$ are ethoxy and $X^-$ is ClO$_4^-$, $R^2$ cannot be 7,10-diacetoxy or 7-acetoxy-10-tert-butyl; further provided that when $R^1$, $R^2$ and $R^7$ are hydrogen, $R^3$ and $R^4$ are methyl and $X^-$ is ClO$_4^-$, $R^5$ and $R^6$ together cannot be —O—CH(CH$_3$)CH(CH$_3$)—O—; still further provided that when $R^1$, $R^4$, $R^5$ and $R^7$ are hydrogen, $R^3$ and $R^6$ are ethoxy and $X^-$is ClO$_4^-$, $R^2$ cannot be 7—NO$_2$; still further provided that $R^5$ and $R^6$ cannot both simultaneously be hydrogen.

The invention further relates to a method for the treatment or prevention of neurodegenerative disorders, or neurotoxic injuries which comprises administering to a patient in need of such treatment an effective amount of a compound of the Formula I:

[Structure I: fused ring system with R3, R4, R5, R6 substituents, X− N+ center, R1, R2, R7 substituents]

wherein:

R$^1$ is hydrogen, or from one to four, the same or different, substituents in any of the 1-, 2-, 3-, or 4-positions selected from the group consisting of lower-alkoxy, lower-alkyl and halogen;

R$^2$ is hydrogen, or from one to four, the same or different, substituents in any of the 7-, 8-, 9-, or 10-positions selected from the group consisting of lower-alkyl, lower-alkanoyloxy, halogen, nitro, hydroxy, lower-alkoxy, methylenedioxy, polyfluorolower-alkyl, and polychloro-lower-alkyl;

R$^3$ and R$^4$ are independently selected from the group consisting of hydrogen, lower-alkoxy, halogen, lower-alkyl, and phenyl;

R$^5$ and R$^6$ are independently selected from the group consisting of hydrogen, lower-alkoxy, trilower-alkyl-silyloxy and dilower-alkylamino; or R$^5$ and R$^6$ together represent CHR$^8$(CH$_2$)$_n$CHR$^9$—O— wherein n is zero or one and R$^8$ and R$^9$ are independently hydrogen, lower-alkyl, or phenyl-lower-alkoxy-lower-alkyl;

R$^7$ is hydrogen, or lower-alkyl; and

X$^-$ is an anion;

or a pharmaceutically acceptable acid-addition salt of basic members thereof; or a hydrate thereof; or a stereoisomer thereof; with the proviso that when R$^1$, R$^3$, R$^4$, and R$^7$ are hydrogen, R$^5$ and R$^6$ are ethoxy and X$^-$ is ClO$_4^-$, R$^2$ cannot be 7,10-diacetoxy or 7-acetoxy-10-tert-butyl; further provided that when R$^1$, R$^2$ and R$^7$ are hydrogen, R$^3$ and R$^4$ are methyl and X$^-$ is ClO$_4^-$, R$^5$ and R$^6$ together cannot be —O—CH(CH$_3$)CH(CH$_3$)—O—; still further provided that when R$^1$, R$^4$, R$^5$ and R$^7$ are hydrogen, R$^3$ and R$^6$ are ethoxy and X is ClO$_4^-$, R$^2$ cannot be 7—NO$_2$; still further provided that R$^5$ and R$^6$ cannot both simultaneously be hydrogen.

The invention further relates to a process for preparing compounds of the Formula IV, useful as intermediates,

[Structure IV: isoquinolinium-type ring system with R2, R7, R1 substituents, X− N+]

which comprises the steps of:
(a) reacting a compound of formula:

[Structure: benzene ring with R2, OH and Y substituents]

wherein Y is hydrogen, or halogen, with at least two molar equivalents of a lower-alkyl alkali metal, optionally in the presence of at least one mole of tetramethylethylene diamine, in an organic solvent, followed by treatment with an excess of a compound of the formula:

[Structure 5: pyridine ring with R1 and C(=O)R7 substituents]

at room temperature or below, to produce a diol of formula:

[Structure: diol with R2-phenyl-CH(OH)- and pyridine-R1 with C(R7)(OH)- linkage]

and (b) treating said diol with: a) an excess of trifluoromethanesulfonic anhydride, in an organic solvent, at room temperature or above; or b) an excess of an acid at room temperature or above; or c) at least one molar equivalent of a phosphorous oxyhalide at room temperature or above; to produce said compounds of formula IV.

DETAILED DESCRIPTION INCLUSIVE OF PREFERRED EMBODIMENTS

The term lower-alkyl as used herein means linear or branched hydrocarbon chains having one to about four carbon atoms and thus includes methyl, ethyl, propyl, isopropyl, n-butyl, sec-butyl, and the like.

The term lower-alkoxy as used herein means linear or branched alkyloxy substituents having one to about four carbon atoms and thus includes methoxy, ethoxy, propoxy, isopropoxy, butoxy, sec-butoxy, and the like.

The term halogen or halide as used herein means bromine, chlorine, iodine, or fluorine.

The term lower-alkanoyloxy as used herein means linear or branched hydrocarbon chains having two to about four carbon atoms and thus includes acetyloxy, propionyloxy, isobutyryloxy, and the like.

The term trilower-alkylsilyloxy as used herein means silyloxy radicals in which the silyl group is substituted by three lower-alkyl groups and wherein lower-alkyl has the meanings given above. The term thus includes trimethylsilyloxy, triethylsilyloxy, tripropylsilyloxy, triisopropylsilyloxy, tri-n-butylsilyloxy, triisobutyl-silyloxy, and the like.

The term anion (X$^-$) as used herein means the anion of an organic acid (includes anions of organic monoacids, as well as monoanions of organic diacids) which is at least as strong as acetic acid, and thus includes anions of such acids as acetic acid, methanesulfonic acid, toluenesulfonic acid, trifluoromethanesulfonic acid, (1S)-(—)-camphanic acid (the anion of which is hereinbelow referred to as (1S)-(—)-C$_{10}$H$_{13}$O$_4^-$), (—)-dibenzoyl-L-tartaric acid [(—)-DBT], (+)dibenzoyl-D-tartaric acid [(+) DBT], (S)-(+)-2-hydroxy-2-phenylpropionic acid, and the like; or it means an inorganic acid anion such as chloride, bromide, perchlorate, PF$_6^-$ and the like, preferably chloride.

The numbering system used throughout the specification is shown in the ring system which is illustrated below. This ring system is usually named in the chemical literature as a

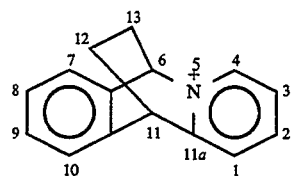

6,11-ethano-6,11-dihydrobenzo[b]quinolizinium or a 6,11-dihydro-6,11-ethanoacridizinium. It should be noted, however, that in some of the earlier chemical literature references (see references cited in Information Disclosure Statement) this ring system was numbered as shown below, and was named as a 9,10-ethano-9,10-dihydro-4a-azoniaanthracene, or a 9,10-dihydro-4a

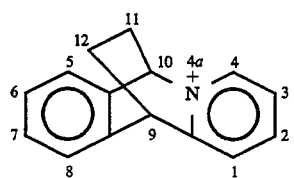

azonia-9,10-ethanoanthracene. Throughout this specification, however, we will use the former numbering system, and we will name the compounds as 6,11-ethano-6,11-dihydrobenzo[b]quinolizinium salts.

The synthesis of the compounds of the invention may be outlined as shown in Scheme A:

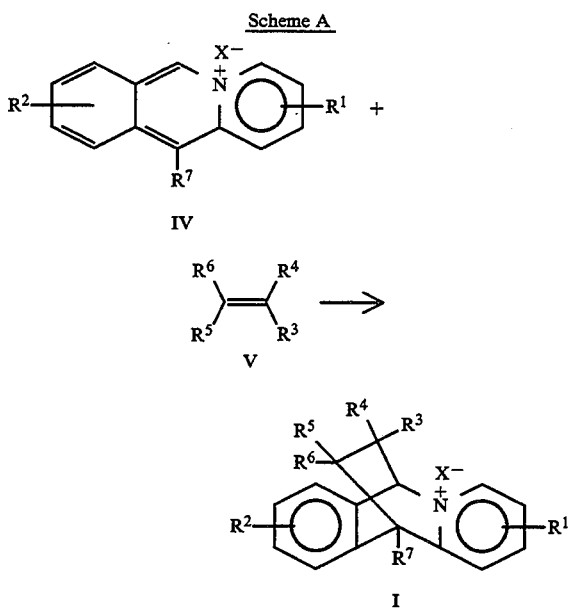

A suitably substituted benzo[b]quinolizinium salt (IV) in an appropriate organic solvent, preferably acetonitrile, is treated with an excess of a suitably substituted olefin (V), at a temperature in the range of about 25° C. up to the boiling point of the solvent used, to afford the compounds of the Formula I. The compounds of the Formulas II and III can be prepared in an analogous manner from the compounds of the Formula IV, wherein $R^1$, $R^2$ and $R^7$ are hydrogen, and an appropriately substituted olefin of the Formula V.

The compounds of the Formulas I, II and III can be converted into other compounds of the Formulas I, II and III which possess various different anion groups, $X^-$, by (a) dissolving a compound of the Formula I, II or III, wherein $X^-$ is an inorganic acid anion, in water, an alcoholic solvent, e.g. methanol, or to a mixture thereof and treating the compound of Formula I, II or III with, or adding it to, a solution of at least one molar equivalent of the alkali metal salt of an inorganic acid anion, $M^+X^-$ wherein the acid of the salt used is a stronger acid than the corresponding acid of the initial acid anion ($X^-$), and wherein $M^+$ is an alkali metal, preferably potassium or sodium, in water, at a temperature in the range of about room temperature up to the boiling point of the solvent used to produce a compound of the Formula I, II or III wherein $X^-$ is various inorganic acid anions; (b) dissolving a compound of the Formula I, II or III, wherein $X^-$ is an inorganic acid anion, in an alcoholic solvent, e.g. methanol or isopropanol, and treating the compound of Formula I, II or III with, or adding it to, a solution of at least one molar equivalent of the potassium salt of an organic monoacid, or the monopotassium salt of an organic diacid, wherein the acid of the salt used is a stronger acid than the corresponding acid of the initial acid anion ($X^-$), in an alcoholic solvent, e.g. methanol or isopropanol, or a mixture of said alcoholic solvent and water, at a temperature in the range of about room temperature up to the boiling point of the solvent used to produce compounds of the Formula I, II or III wherein $X^-$ is various organic acid anions; (c) dissolving a compound of the Formula I, II or III wherein $X^-$ is an organic acid anion, in an alcoholic solvent, e.g. methanol, and adding this solution to a mixture of an excess of a base, preferably sodium bicarbonate, and an excess of the alkali metal salt of an inorganic acid anion, $M^+X^-$ wherein the acid of the salt used is a stronger acid than the corresponding acid of the initial acid anion ($X^-$), in water, at a temperature of about room temperature up to the boiling point of the solvent used, to produce compounds of the Formula I, II or III wherein $X^-$ is an inorganic acid anion; (d) if compounds of the Formula I, II or III wherein $X^-$ is chloride ($Cl^-$) are desired it is preferred to dissolve a compound of the Formula I, II or III, wherein $X^-$ is an organic acid anion, or an inorganic acid anion which is other than chloride, in an appropriate organic solvent, e.g. acetonitrile, ethylacetate, alcoholic solvents such as methanol, or mixtures of said solvents, and pass the solution through Dowex ® 1X2-100 ion-exchange resin (Dowex ®-1-chloride), eluting with water, to provide the corresponding chloride anion; or e) by passing a compound of the Formula I, II, or III through a suitable ion-exchange resin column (prepared, for example, by treating Dowex ® 1×2-200 ion-exchange resin with a suitable organic acid or inorganic acid) to provide various compounds of Formula I, II, or III wherein $X^-$ is other than $Cl^-$, $ClO_4^-$ or $PF_6^-$.

The compounds of general Formulas I, II and III can possess one or more asymmetric carbon atoms and are thus capable of existing in a number of stereoisomeric forms, e.g. enantiomers, diastereomers, and geometric isomers. Unless otherwise specified herein, the invention is intended to extend to each of these stereoisomeric forms, and to mixtures thereof, including the racemates. The different stereoisomeric forms may be separated one from the other by the methods described hereinbelow.

The diastereomers/geometric isomers can be separated by conventional procedures which are well known in the art of chemistry such as chromatography, fractional crystallization and the like. The separation of enantiomers can be accomplished by a) chiral chromatography; b) treating a racemic mixture of a compound of the Formulas I, II or III with the potassium salt of (+)-dibenzoyl-D-tartaric acid (K+[(+)-DBT]) to afford a compound of the Formula I, II or III as the $^-$[(+)-DBT] salt; fractional crystallization of the $^-$[(+)-DBT] salt to afford a single diastereomer of the $^-$[(+)-DBT] salt, and then conversion of the single diastereomer of the $^-$[(+)-DBT] salt into various other non-chiral anions (X$^-$) by following the procedures described hereinabove for the conversion of compounds of the Formulas I, II, and III into other compounds of the Formulas I, II and III with various different anions (X$^-$), to produce the compounds of the Formulas I, II or III as a single enantiomer; or c) treating a racemic mixture of a compound of the Formulas I, II or III with the potassium salt of (−)-dibenzoyl-L-tartaric acid (K+[(−)-DBT]) to afford a compound of the Formulas I, II or III as the $^-$[(−)DBT] salt and then proceeding as described hereinabove in part (b) to afford the compounds of the Formulas I, II or III as the other enantiomer.

Alternatively, the preparation of enantiomers wherein R$^5$ and R$^6$ are the same lower-alkoxy group can proceed as illustrated in Scheme B. A compound of the Formula I, wherein R$^5$ and R$^6$

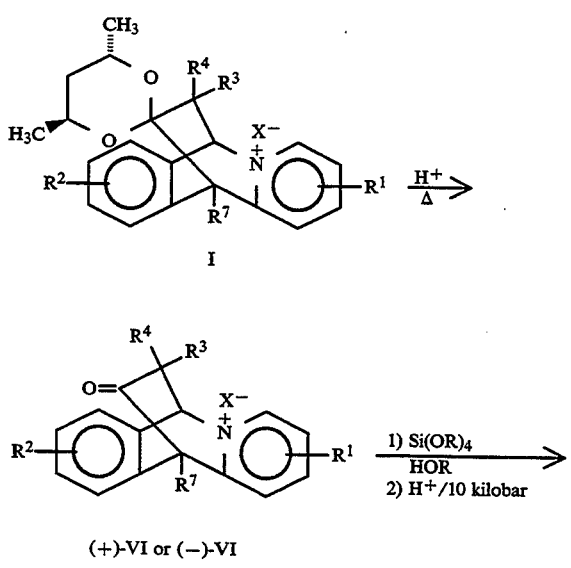

Scheme B

I (+)-VI or (−)-VI

-continued
Scheme B

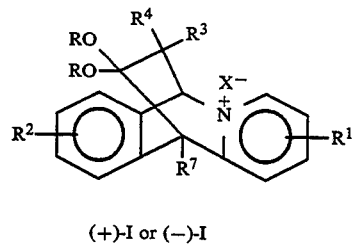

(+)-I or (−)-I together are —O—CH(CH$_3$)CH$_2$CH(CH$_3$)—O—, or a corresponding diastereomer thereof, can each individually be treated with an excess of an acid, preferably concentrated hydrochloric acid, at a temperature in the range of about 25° C. up to about 80° C. to afford the ketones of the Formula VI as the (+)-enantiomer or the (−)-enantiomer. The individual enantiomers can then be converted back into a ketal by (a) treating an enantiomer of the Formula VI with an excess of a tetralower-alkoxysilane (Si(OR)$_4$), wherein OR is a lower-alkoxy group e.g. methoxy or ethoxy, in a solvent mixture consisting of an excess of an organic solvent which is suitable to azeotrope off residual water, preferably chloroform, an excess of a second organic solvent in which the compound of the Formula VI is soluble, preferably nitromethane, and an excess of an alcoholic solvent (ROH), e.g. methanol, or ethanol wherein the RO portion of the alcohol is the same as the lower-alkoxy portion of the tetralower-alkoxysilane, at the boiling point of the azeotropic solvent, for a time sufficient to distill off the azeotropic solvent and any residual water; and (b) cooling the reaction mixture to about 25° C., adding at least one molar equivalent of triflic acid, and placing the mixture in a high pressure apparatus at about 10 kbar to afford the compounds of the Formula I, wherein R$^5$ and R$^6$ are the same-lower-alkoxy group, as the individual (+)- or (−)-enantiomers.

When the enantiomers are resolved as described hereinabove, it has been found that one of the enantiomers may possess advantages of greater potency and fewer side effects when compared to the other enantiomer or the racemate, and such advantages can be readily determined by those skilled in the art. As an illustrative example, the compound of Example 2 was resolved into its separate enantiomers and it was found that the (−)-enantiomer (Example 12(c)) was more potent and had fewer side effects when compared to the (+)-enantiomer (Example 13(c)) or the racemate (Example 2) and that such a compound is therefore a preferred species of the invention.

The suitably substituted benzo[b]quinolizinium salts of the Formula IV, which are required for the synthesis of the compounds of Formulas I, II or III, can be prepared as shown in Scheme C. At least one molar equivalent of an appropriately substituted benzyl halide (VII), wherein Z is a halogen,

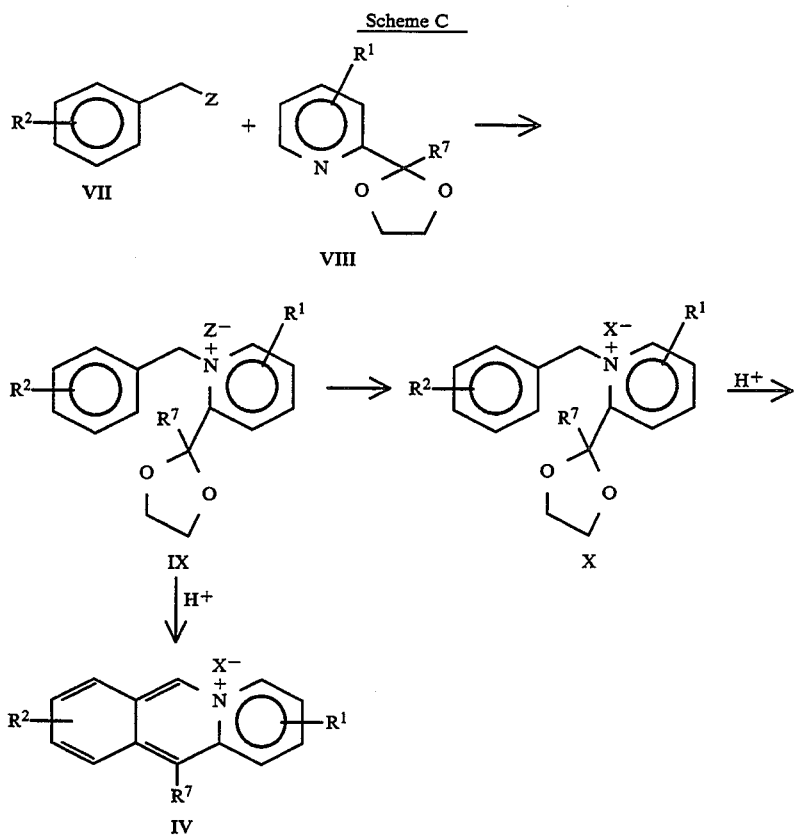

preferably chlorine or bromine, is admixed with an excess of an appropriately substituted 2-(1,3-dioxolan-2-yl)pyridine (VIII), in the presence or absence of a suitable organic solvent, preferably sulpholane, at a temperature in the range of about room temperature up to about 146° C., to produce the pyridinium salt (IX). If desired, the pyridinium salt (IX) can then be converted into other pyridinium salts of the Formula X, wherein X⁻ has the meanings given above, by utilizing procedures similar to those described hereinabove for the preparation of compounds of the Formulas I, II and II with various anions (X⁻). The pyridinium salt (X), or if conversion into various anions, X⁻, was not effected, the pyridinium salt (IX) can then be treated with an excess of an acid, e.g. polyphosphoric acid, 48% hydrobromic acid, concentrated hydrochloric acid, or a mixture of polyphosphoric acid and methanesulfonic acid, at a temperature in the range of about room temperature up to about 115° C., to afford the benzo[b]quinolizinium salts of Formula IV.

Alternatively, the benzo[b]quinolizinium salts of Formula IV can be prepared as shown in Scheme D. A suitably substituted benzyl alcohol (XI), wherein Y is hydrogen, or halogen, especially hydrogen or bromine, is treated with at least

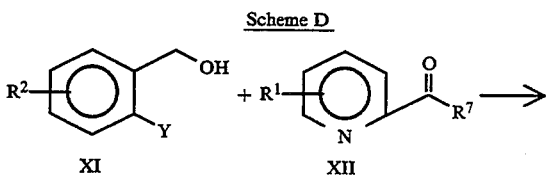

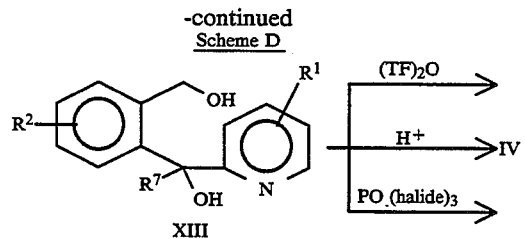

two molar equivalents of a lower-alkyl alkali metal, preferably n-BuLi, optionally in the presence of at least one mole of a second base, e.g. tetramethylethylenediamine, followed by the addition of an excess of a suitable pyridine derivative (XII), in an organic solvent, such as ether, at room temperature or below, preferably at a temperature in the range of about room temperature to about −30° C. to afford the diol (XIII). The diol (XIII) can then be treated with (a) an excess of trifluoromethanesulfonic anhydride ((TF)₂O), in a suitable solvent, e.g. benzene, at about room temperature or above, preferably at a temperature in the range of about room temperature up to about 90° C., to afford a compound of the Formula IV wherein X⁻ is −OTF; or (b) an excess of an acid, e.g. 45% hydrobromic acid in acetic acid, at about room temperature or above, preferably at a temperature in the range of about room temperature to about 100° C., to produce the compounds of the Formula IV; or (c) at least one molar equivalent of a phosphorous oxyhalide, preferably phosphorous oxychloride, at about room temperature or above, preferably at a temperature in the range of about room temperature up to the boiling point of the phosphorous oxyhalide, to afford a compound of the Formula IV wherein X⁻ is halogen. It will be noted that the methods described hereinabove in Scheme D are the preferred methods when it is desired to prepare benzo[b]quinolizinium salts of Formula IV which contain substituents in the 10- and/or 11- positions.

If desired, the benzo[b]quinolizinium salts of Formula IV can be converted into other compounds of the Formula IV which possess various different anion groups, $X^-$, by following procedures similar to those described hereinabove for the conversion of compounds of the Formulas I, II and III, to various other anion groups.

Simple chemical transformations which are conventional and well known to those skilled in the art of chemistry can be used for effecting changes in functional groups of the compounds of the Formulas I, II, III, and IV. For example, dealkylation of ethers to produce the corresponding alcohols, acetylation of alcohols to produce the corresponding acetates, hydrolysis of acetates to produce the corresponding alcohols, and halogenation of aryl rings to produce the corresponding aryl halides.

The appropriately substituted olefin (V), the alkali metal salts of an inorganic acid anion or an organic acid anion, benzyl halide (VII), 2-(1,3-dioxolan-2-yl)pyridine (VIII), benzyl alcohol derivative (XI), and pyridine (XII) are commercially available, or they can be prepared by procedures well known in the art, or by the procedures described herein below.

The compounds of Formulas I, II and III which contain basic substituents are useful both in the free base form and in the form of acid-addition salts, and, both forms are within the purview of the invention. The acid-addition salts are often a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not vitiated by side effects ascribable to the anions. In practicing the present invention it is convenient to use the free base form or the hydrochloride, fumarate, toluenesulfonate, methanesulfonate or maleate salts. However, other appropriate pharmaceutically acceptable salts within the scope of the invention are those derived from other mineral acids and organic acids. The acid-addition salts of the basic compounds are prepared by standard procedures well known in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed for purposes of purification or identification, or when it is used as an intermediate in preparing a medicinally acceptable salt by, for example, ion exchange procedures.

The compounds of Formula I, II and III are quinolizinium salts in which it is preferred that the salts are pharmaceutically acceptable salts, that is, salts whose anions ($X^-$) are relatively innocuous to the animal organism in pharmaceutical doses of the salts, so that the beneficial properties inherent in the compounds of the Formulas I, II and III are not vitiated by side effects ascribable to the anions ($X^-$). In practicing the present invention it is convenient to use the anions ($X^-$) of organic acids such as methanesulfonic acid and toluenesulfonic acid, or the anions ($X^-$) of inorganic acids such as hydrobromic acid and hydrochloric acid. However, other appropriate pharmaceutically acceptable salts within the scope of the invention are those derived from the anions ($X^-$) of other organic acids, organic diacids, or inorganic acids.

The structures of the compounds of the invention were established by the mode of synthesis, and by one or more of elemental analysis, and infrared, nuclear magnetic resonance and mass spectroscopy. The course of the reactions and the identity and homogeneity of the products were assessed by one or more of thin layer chromatography (TLC), high pressure liquid chromatography (HPLC), or gas-liquid chromatography (GLC).

The following examples will further illustrate the invention without, however, limiting it thereto. All melting points (m.p.) are given in degrees C (° C.) and are uncorrected. The abbreviation E/PAW as used herein means ethyl acetate in pyridine/acetic acid/water (55/20/25); and TEA stands for triethylamine.

Preparation of Starting Materials

Preparation 1

A mixture of 1-benzyl-2-(1,3-dioxolan-2-yl)pyridinium bromide (2.43 mol) in 6000 ml of 48% HBr was placed in a 12 L 3-neck flask equipped with a mechanical stirrer and the reaction mixture was allowed to stir at room temperature overnight. The reaction mixture was heated on a steam-bath for 3 hours, concentrated in vacuo, and a light yellow solid was filtered and washed with THF yielding 415 g of a solid product. The bromide was dried in a dessicator under diminished pressure to afford 351 g (56%) of benzo[b]quinolizinium bromide (Formula IV: $R^1=R^2=R^7=H$; $X^-=Br^-$), as a light yellow solid, m.p. 222°–225° C.

Preparation 2

(a)

To a solution of 74.2 g (0.65 mol) of 1,1-dimethyl-2-acetoxyethylene in 300 ml of tetrachloromethane cooled to 0°–5° C. was added in portions 103 g (0.65 mmol) of bromine in 200 ml of tetrachloromethane at a rate to maintain an internal temperature of 0°–10° C. After the addition (approx. 2 hours), 300 ml of methanol was added to the mixture and the resulting mixture was allowed to stir for 46 hours in a reaction flask equipped with a drying tube. The reaction mixture was poured into 1 L of water, the organic layer was separated and dried, the organic solvent was removed (atmospheric pressure), and the residue was distilled to afford 100 g (78.1%) of 1,1-dimethoxy 2-bromo-2-methylpropane, b.p. 62°–67° C.

(b)

A mixture of 101 g (0.67 mol) of L-tartaric acid and 160 g (1.53 mol) of 2-dimethoxypropane in 40 ml of methanol and 400 mg of p-toluenesulfonic acid was heated to 100° C. in an oil-bath and the mixture was allowed to react for 1½ hours. To the resulting dark-red solution was added 80 g (0.77 mol) of 2,2-dimethoxypropane and 450 ml of cyclohexane, and the mixture was allowed to reflux (bath temp. approx. 95° C.) for 13 hours while distilling 590 ml of organic solvents (methanol-cyclohexane, acetone-cyclohexane). The reaction mixture was cooled to room temperature, 1 g of potassium carbonate was added, and concentrated in vacuo. The residue was distilled to afford 122 g (82.4%) of 2,2-dimethyl-4(R), 5(R)-(dicarbomethoxy)-1,3-dioxolane, b.p. 92°–95°/0.04 mm).

(c)

A suspension of 46 g (1.21 mol) of lithium aluminum hydride in 500 ml of ether was refluxed for 10 mins. and cooled to room temperature. To the above mixture was added in portions with vigorous stirring a solution of 122 g (0.599 mol) of 2,2-dimethyl-4(R),5(R)-(dicarbomethoxy)-1,3-dioxolane in 500 ml of ether at a rate to maintain a gentle reflux. After the addition (approx. 2 hours), the reaction mixture was refluxed for 3 hours, cooled in a dry-ice/acetone bath, and 50 ml of ethyl acetate was added carefully followed by 46 ml of water, 4N NaOH solution (46 ml), and water (130 ml) with caution.

The reaction mixture was stirred for 15 mins. The precipitated solid was removed by filtration, washed successively with ether (500 ml), ethyl acetate (750 ml), methylene chloride (750 ml), and ether (500 ml). The combined filtrate was concentrated in vacuo, the residue was dissolved in ethyl acetate (500 ml), and washed with 100 ml of saturated ammonium chloride solution. The organic layer was dried, concentrated in vacuo, and the residue was distilled (Kugelrohr) to afford 29.1 g (32.1%) of 2,2-dimethyl-4(R),5(R)-(-dihydroxymethyl)-1,3-dioxolane, b.p. 120° C. (Kugelrohr).

(d)

Sodium hydride (16.8 g of 60% dispersed in oil; 0.36 mol) was freed of oil by stirring with hexane (2°100 ml) and removing the supernatant using a cannula. Sodium hydride was freed of hexane by evaporation. To a mixture of sodium hydride (oil free) in 150 ml of THF was added a solution of 29 g (0.18 mol) of 2,2-dimethyl-4(R),5(R)-(-dihydroxy-methyl)-1,3-dioxolane in 100 ml of THF over a 30 min. period. The reaction mixture was stirred for 1 hour, a solution of 68 g (0.36 mol) of benzylbromide in 50 ml of THF was added over a 15 min. period, and the resulting mixture was allowed to stir under nitrogen overnight.

The reaction mixture was refluxed for 2 hours, cooled to room temperature, diluted with 50 ml of water, and concentrated in vacuo. The residue was extracted with 500 ml of toluene, the organic layer was dried over sodium sulfate, and concentrated in vacuo. The residue was passed through 6 inch silica pad eluting with 10% methylene chloride in hexane followed by 15% ethyl acetate in hexane. The later fraction was concentrated to afford 42 g (68.6%) of 2,2-dimethyl-4-(R),5(R)-(-dibenzyloxy-methyl)-1,3-dioxolane.

(e)

To a solution of 42 g (0.122 mol) of 2,2-dimethyl-4(R),5(R)-(-dibenzyloxy-methyl)-1,3-dioxolane in 100 ml of methanol was added 10 ml of 0.5N HCl solution and the resulting mixture was heated to 75° C. distilling the acetone/methanol slowly over a period of 5 hours. The reaction mixture was cooled to room temperature, 5 ml of 0.5N HCl solution and 25 ml of methanol were added, and the mixture was concentrated in vacuo. The residue was basified with saturated sodium bicarbonate solution, extracted with 500 ml of benzene, and the organic layer dried, filtered, and concentrated in vacuo. The residue was purified by chromatography to afford 7.5 g (20.3%) of 1,4-dibenzyloxy-2(R),3(R)-(dihydroxy)butane.

(f)

A reaction mixture of 7.5 g (24.8 mmol) of 1,4-dibenzyloxy-2(R)3(R)-(dihydroxy)-butane and 4.1 g (20.8 mmol) of 1,1-dimethoxy 2-bromo-2-methylpropane in 250 ml of toluene and 0.5 g of PPTS was refluxed under nitrogen for 1 hour using a Dean-Stark trap, while azeotroping the methanol formed. The resulting reaction mixture was cooled to room temperature, washed successively with saturated sodium bicarbonate solution, water, and brine, dried and concentrated in vacuo. The residue was passed through 6 inch silica pad eluting with 1000 ml of hexane/ethyl acetate (7:2). The eluent was concentrated in vacuo to afford 8.9 g (82.4%) of 2[2'-bromo-2-methylpropyl]-4-(R),5(R)-(trans-dibenzyloxymethyl)1,3-dioxolane.

(g)

To a suspension of potassium tert-butoxide (0.8 g; 7.13 mmol) in 15 ml of THF was added a solution of 2.12 g (4.8 mmol) of 2-[2'-bromo-2-methylpropyl]-4(R),5(R)-(trans-dibenzyloxymethyl) 1,3-dioxolane in 5 ml of THF over a 15 min. period. The reaction mixture was stirred at room temperature under nitrogen for 2 hours, passed through a 3″ silica pad eluting with 300 ml of ether, the eluent was dried over sodium sulfate, and the solvent was concentrated in vacuo to afford 1.7 g (98.3%) of 2-propylidene-4(R),5(R)-(trans-dibenzyloxymethyl)1,3-dioxolane (Formula V: $R^3=R^4=CH_3$; and $R^5$ and $R^6$ together are (R,R)—O—CH(CH$_2$OCH$_2$Ph)CH (CH$_2$OCH$_2$—Ph)O—), as a viscous oil.

Preparation 3

(a)

A solution of 35.5 g (1.1 mol) of methanol in 400 ml of anhydrous ether cooled to −5° C. was saturated with HCl gas (until exothermic reaction subsides). To the above solution was added 69.1 g (1 mol) of isobutyronitrile, the resulting mixture was stoppered and stored in a refrigerator for 24 hours. The precipitated solid was filtered, washed with anhydrous ether (750 ml), and dried in a vacuum oven for 40 hours to afford 125 g (90.8%) of 1-imino-1-methoxyisobutane hydrochloride.

(b)

To 1-imino-1-methoxyisobutane hydrochloride (67 g, 0.487 mol) dissolved in 200 ml of dry methanol (dried over 3° A sieves) was added 900 ml of anhydrous ether, and the resulting reaction mixture was heated at 45° C. under nitrogen for 18 hours. The reaction mixture was cooled in an ice-bath, filtered, and the filtrate was basified (pH 8.6) by an addition of solid sodium methoxide. The solvent was removed on a steam-bath and the residue was distilled to afford 10 g of 1,1,1-trimethoxyisobutane which upon redistillation over NaH yielded 9 g (13%) of 1,1,1-trimethoxyisobutane, b.p. 134°–136° C.

(c)

To a mixture of 3.8 g (25.6 mmol) of 1,1,1-trimethoxyisobutane and 3 g (28.8 mmol) of 2(R),4(R)-dihydroxypentane in 100 ml of toluene was added 200 mg of PPTS and the resulting reaction mixture was allowed to reflux under nitrogen for 20 hours while azeotroping methanol formed using the Dean-Stark trap. The reaction mixture was cooled, washed successively with saturated sodium bicarbonate solution, water, and brine. The toluene layer was dried, the solvent was concentrated under nitrogen, and the residue was distilled to afford 2.1 g (52.5%) of 2-isopropylidene-4(R),6(R)-dimethyl-1,3-dioxane (Formula V: $R^3=R^4=CH_3$; $R^5$ and $R^6$ together are $(R,R)-O-CH(CH_3)CH_2CH(CH_3)O-$), b.p. 95°–100° C./10 mm.

(d)

A mixture of 15.6 g (0.105 mol) of 1,1,1-trimethoxyisobutane, 10 g (0.0962 mol) of 2(S),4(S)-dihydroxypentane, and 251 mg of PPTS in 150 ml of toluene (dried over 3° A sieves) was allowed to reflux under argon for 1 1/2 hours while azeotroping water formed using the Dean-Stark trap. The reaction mixture was cooled, 1.2 g of potassium tert. butoxide was added, and the solvent was distilled. Ether (100 ml) was added to the residue, passed through a supercel pad eluting with 300 ml of ether, and the combined solvent was distilled in vacuo (<40° C.). The residue was distilled to afford 14.3 g (79.4%) of 2-isopropyl-2-methoxy-4(R),6(R)-dimethyl-1,3-dioxane, b.p. 78°–82° C./15 mm.

(e)

To 3.8 g (20.2 mmol) of 2-isopropyl-2-methoxy-4(R),6(R)-dimethyl-1,3-dioxane was added 4.97 g (20.2 mmol) of aluminum tert. butoxide and the resulting mixture was heated to 180° C. under nitrogen (over a 30 min. period) and maintained at this temperature for one hour while distilling tert. butanol formed. The residue was cooled and distilled (directly from the reaction flask) to afford 2.05 g (65%) of 2-isopropylidene-4(R),6(R)-dimethyl-1,3-dioxane (Formula V: $R^3=R^4=CH_3$; $R^5$ and $R^6$ together are $(R,R)-O-CH(CH_3)CH_2CH(CH_3)O-$), b.p. 75°–78° C./aspirator vacuum.

Preparation 4

(a)

A solution of 138.2 g (2 mol) of isobutyronitrile in 101.2 g (2.2 mol) of ethanol cooled to 0° C. was saturated with anhydrous HCl gas (total vol. of HCl=1.5 L: 2.2 mol) at a rate of 1.5 L/min for 35 minutes. The resulting mixture was tightly capped and stored in a refrigerator (−5° C.) for 5 days and then stirred at room temperature for 18 hours. The solid formed was removed by filtration and the filtrate was poured into 2 L of anhydrous ether with stirring and the resulting reaction mixture was stirred at 0°–5° C. for 30 minutes. The precipitated solid was filtered, washed with anhydrous ether, and dried in a vacuum oven (over KOH) to afford 150 g (98.9%) of 1-imino-1-ethoxyisobutane hydrochloride.

(b)

A mixture of 1-imino-1-ethoxyisobutane hydrochloride (150 g, 0.989 mol) and 550 g of ethanol (11.9 mol) in anhydrous ether (3.5 L) was allowed to reflux (38°–39° C.) under argon for 72 hours. The reaction mixture was cooled to room temperature, allowed to stand at room temperature for 2 days, and filtered. The filtrate was washed with 10% sodium carbonate solution (2×1 L) followed by saturated sodium carbonate solution (1×1 L), the organic layer was dried (potassium carbonate), and the solvent was concentrated in vacuo (bath temp. <30° C.). The residue was dissolved in 300 ml of ether, filtered, and the filtrate was washed successively with 10% NaOH solution and water, and then dried (potassium carbonate).

The solvent was removed in vacuo (bath temp. <30° C.), the residual liquid was diluted with 250 ml of hexane, cooled in an ice-bath (1 hour), and filtered. The filtrate was concentrated in vacuo (<30° C.) and the residue was distilled to yield 55.2 g (28%) of 1,1,1-triethoxyisobutane, b.p. 70°–72° C./27 mm.

(c)

A reaction mixture of 55 g (0.289 mol) of 1,1,1-triethoxyisobutane and 60 g (0.244 mol) of aluminum tert-. butoxide placed in a reaction flask equipped with 12" Vigreux distilling column was heated to 170° C. over a 30 min. period and maintained at this temperature for 1 hour while distilling tert. butanol formed. When the distillation of t-butanol was complete, the Vigreux column was replaced with a short path distillation unit and the distillation was continued to afford 31g (74.5%) of 1,1-diethoxy-2: 2-dimethylethylene (Formula V: $R^3=R^4=CH_3$; $R^5=R^6=OC_2H_5$), b .p. 90°–120° C.

Preparation 5

(a)

To a solution of 50 g (0.326 mol) of m-methoxybenzyl alcohol in 1.1 L of anhydrous ether cooled to −20° C. was added in portions 76 ml (0.76 mol) of 10M n-butyllithium solution hexane at a rate to maintain an internal temperature below −10° C. The resulting mixture was warmed to room temperature and stirred for 2 hours.

The above reaction mixture was cooled to 0° C. and TMEDA (42 g; 0.362 mol) was added. The resulting reaction mixture was cooled to −30° C. and 58 g (0.542 mol) of pyridine-4-carboxaldehyde was added over a 5 min. period (−10° C.) and then the mixture was allowed to warm to 0° C. over a 30 min. period.

The reaction mixture was quenched by an addition of 500 ml of water with stirring for 30 minutes and the mixture was chilled in a refrigerator overnight. The precipitated diol was isolated by filtration, washed with ether, dried, and crystallized from ethanol to afford 30 g (33.8%) of 2-[1-hydroxy-(2'-methoxy-6'-hydroxymethyl)-benzyl]pyridine (Formula XIII: $R^1=R^7=H$; $R^2=2'-OCH_3$). The filtrate was concentrated and diluted with ether to afford an additional 13.1 g (14.7%) of the diol.

(b)

A mixture of 13.1 g (53.4 mmol) of 2-[1-hydroxy-(2'-methoxy-6'-hydroxymethyl)-benzyl]pyridine in 75 ml of 45% HBr in acetic acid was allowed to reflux for 20 hours and the reaction mixture was cooled to room temperature. After removing a portion of acetic acid by distillation, 25 ml of 45% HBr was added to the mixture and refluxed for an additional 4 hours. The reaction mixture was cooled to room temperature, poured into 700 ml of methylene chloride with stirring and the precipitated solid was isolated by filtration to afford 9 g (61.2%) of 10-hydroxybenzo[b]quinolizinium bromide (Formula IV: $R^1=R^7=H$; $R^2=10$—OH; $X^-=Br^-$).

The above filtrate was concentrated in vacuo to afford 4 g (25.8%) of 10-methoxybenzo[b]quinolizinium bromide (Formula IV: $R^1=R^7=H$; $R^2=10$—$OCH_3$; $X^-=Br^-$).

The above 10-hydroxybenzo[b]quinolizinium bromide, (9 g) was purified by dissolving in 600 ml of acetonitrile, refluxing the solution, and filtering the mixture while hot. The solid product was filtered and washed with ether to afford 5 g of 10-hydroxybenzo [b]quinolizinium bromide.

(c)

To a solution of 6.5 g (23.6 mmol) of 10-hydroxybenzo[b]quinolizinium bromide in 400 ml of methylene chloride/pyridine (1:1) was added 100 mg of DMAP and 50 ml of acetic anhydride and the resulting reaction mixture was stirred under argon at room temperature for 2 hours. The reaction mixture was concentrated in vacuo. The residue was suspended in 2:1 10% $NaClO_4/CH_2Cl_2$ (300 ml) and sonicated. The solid was collected by filtration to afford 4.3 g (55.9%) of 10-acetoxybenzo[b]quinolizinium perchlorate.

The above 10-acetoxybenzo[b]quinolizinium perchlorate (3.3 g) was dissolved in 500 ml of water, the solution was boiled, and filtered. To the filtrate was added 100 ml of 30% sodium perchlorate solution and the mixture was chilled. The precipitated solid was isolated by filtration and dried in vacuo to afford 1.9 g of 10-acetoxybenzo[b]quinolizinium perchlorate (Formula IV: $R^1=R^7=H$; $R^2=10$—OAc; $X^-=ClO_4$). The filtrate was extracted with methylene chloride (3×100 ml), the organic layer was dried and concentrated to yield an additional 0.32 g of the desired acetate perchlorate.

Preparation 6

(a)

A mixture of 9.4 g (60 mmol) of o-methoxybenzyl chloride and 2-(1,3-dioxolan-2-yl)pyridine in sulfolane (6 ml) was heated at 80° C. for 5 hours, cooled to room temperature, and was allowed to stand overnight. The mixture was poured into 100 ml of ethyl acetate and the reaction mixture was stirred for 30 minutes. A gummy precipitate was isolated by decanting ethyl acetate and triturated with ethyl acetate (2×). The gummy product was dissolved in 100 ml of water, filtered, and treated with 150 ml of hot aqueous potassium hexafluorophosphate solution. The solid salt was isolated by filtration, washed successively with hot water and ether, and dried to afford 7.4 g (29.6%) of 1-(o-methoxybenzyl) -2(1,3-dioxolan-2yl) pyridinium hexafluorophosphate (Formula X: $R^1=R^7=H$; $R^2=2'$—$OCH_3$; $X^-=PF_6^-$).

(b)

To 50 g of polyphosphoric acid heated to 95° C. in an oil-bath was added with stirring 5 g (12 mmol) of 1-(o-methoxybenzyl)-2(1,3-dioxolan-2-yl)pyridinium hexafluorophosphate and the resulting reaction mixture was heated at this temperature with stirring under nitrogen for 5 hours. The mixture was cooled to 40° C., and 125 ml of water was added followed by an additional 125 ml of water. The resulting mixture was cooled to room temperature, potassium hexafluorophosphate (5 g, 27 mmol) was added, the precipitated solid was isolated by filtration, and the desired salt was washed successively with water and ether and then dried to afford 3.2 g (74.9 g) of 7-methoxybenzo[b]quinolizinium hexafluorophosphate (Formula IV: $R^1=R^7=H$; $R^2=7$—$OCH_3$; $X^-=PF_6^-$).

Preparation 7

(a)

A mixture of 116 g (1 mol) of 2-ethylbutyric acid, 135 g (1.05 mol) of dimethyl sulfate, and 155 g (1.12 mol) of potassium carbonate in 500 ml of acetone was stirred at room temperature under nitrogen overnight, and then was allowed to reflux under nitrogen for 1 hour. The reaction mixture was cooled to room temperature, filtered, and the residual solid was washed with 500 ml of ether. The combined filtrate was concentrated in vacuo, the residue was redissolved in ether, the ether solution was washed successively with water and brine and then dried. The solvent was concentrated and the residual liquid was distilled to afford 70 g (53.8 %) of methyl 2-ethylbutyrate, b.p. 135°–137° C.

(b)

To a solution of 10.1 g (0.1 mol) diisopropylamine in 75 ml of THF cooled to 0° C. was added 10 ml (0.1 mol) of 10M solution of n-butyllithium in hexane and the mixture was stirred for 5 minutes. The reaction mixture was cooled to −78° C., and 13 g (0.1 mol) of methyl 2-ethylbutyrate in 15 ml of THF was added over a 10 min. period. The resulting mixture was stirred at −78° C. for 1.5 hours, and then 21.8 g (0.2 mol) of trimethylsilyl chloride (freshly distilled over quinoline) was added over a 10 min. period followed by an additional stirring at −78° C. for 15 minutes.

The reaction mixture was allowed to warm to room temperature, stirred for 30 minutes, the solvent was concentrated in vacuo, and the residue was redissolved in 100 ml of pentane and filtered. The filtrate was concentrated in vacuo and the residual liquid was distilled to afford 15.5 g (76.7%) of 2,2-diethyl-1-(trimethylsilyloxy)-1-methoxyethylene (Formula V: $R^3=R^4=C_2H_5$; $R^5=OSi(CH_3)_3$; $R^6=OCH_3$), b.p. 94°–97° C./55 mm.

Preparation 8

(a)

To a mixture of 9.3 g (69 mmol) of N-formylpyrrolidine hydrochloride in 25 ml of tetrachloroethane, chlorine gas was passed through until the mixture turned yellow. To the above mixture was added 50 g (0.693 mol) of isobutyraldehyde in portions at a rate to maintain an internal temperature at 55° C. while passing chlorine gas through slowly. After the addition of isobutyraldehyde, the mixture was stirred (55° C.) for 20 minutes and distilled at <50° C./25 mm (50 % of isobutyraldehyde was recovered).

Additional isobutyraldehyde was added to the mixture in portions (via syringe) over a 2 hr period and stirred at 55° C. for 1 hour. The product was distilled to afford 45 g (61.6%) of 2-chloro-2-methylpropanal, b.p. <40° C./25 mm.

(b)

To a mixture of 45 g (0.424 mol) of 2-chloro-2-methylpropanal, 99.6 ml (1.69 mol) of ethanol, 81.6 g (0.55 mol) of triethylorthoformate in 100 ml of methylene chloride was added 800 mg (4.2 mmol) of p-toluenesulfonic acid and the mixture was stirred at room temperature. After adding 2 g of potassium carbonate to the above mixture, the reaction mixture was stirred (2 min.), and filtered. The filtrate was concentrated (80° C.) to remove methylene chloride and the residue was distilled (2×) to afford 52 g (68.2%) of 2-chloro-2-methylpropanal diethyl acetal, b.p. 55°-65° C./25 mm.

(c)

To a mixture of 12 g ( 66.6 mol) of 2-chloro-2-methylpropanal diethyl acetal and 15 g (0.24 mol) of ethylene glycol in 200 ml of toluene was added 500 mg of PPTS and the resulting mixture was refluxed under nitrogen while azeotroping water formed with the Dean-Stark trap for a period of 16 hours. The desired dioxolane was isolated by cooling the mixture to room temperature, separating the organic layer, washing the organic layer with saturated sodium bicarbonate, water and then brine and then drying over $Na_2SO_4$ and removing the solvent in vacuo. The product was distilled to afford 7 g (69.7%) of 2-[2'-(2'-chloro)propyl]1,3-dioxolane, b.p. 55°-60° C./aspirator.

(d)

To a suspension of 7.15 g ( 63.7 mmol) of potassium t-butoxide in 100 ml of THF was added in portions 6.4 g (42.5 mmol) of 2-[2'-(2'-chloro)propyl]-1,3-dioxolane in 10 ml of THF over a 15 min. period. The exothermic reaction mixture was stirred for 15 minutes and the organic solvent was distilled. The residual liquid was 2-isopropylidene-1,3-dioxolane (Formula V: $R^3=R^4=CH_3$; $R^5$ and $R^6$ together are $-OCH_2CH_2O-$).

Preparation 9

(a)

To a mixture of 63.55 g (0.46 mol) of o-methoxybenzyl alcohol in 1.5 L of ether cooled to −40° C. was added in 2 portions (100 mL) of 10M n-butyllithium over a 30 min. period and the reaction mixture was slowly (removing a bath) warmed to room temperature and stirred for 30 minutes.

The above reaction mixture was cooled to −20° C., 69.7 g (0.651 mol) of 2-pyridinecarboxaldehyde was added to the mixture, and the resulting reaction mixture was allowed to warm to room temperature. After 1 hour, ammonium chloride solution was added to the mixture. The diol was extracted with ethyl acetate, dried over sodium sulfate, and the solvent was removed in vacuo. Recrystallization (2×) from ethyl acetate/ether afforded 68.5 g (60.7%) of 2-[1-hydroxy-(2'-methoxy-6'-hydroxymethyl)-benzyl]pyridine (Formula XIII: $R^1=R^7=H$; $R^2=2'=OCH_3$).

(b)

To 25 g (0.102 mol) of 2-[1-hydroxy-(2'-methoxy-6'-hydroxymethyl)benzyl]-pyridine was added rapidly with stirring 30 ml of $POCl_3$ and the resulting mixture was placed in an oil bath preheated to 110° C. The exothermic reaction mixture (with evolution of HCl gas) was cooled, 250 ml of methylene chloride was added, and the solvent was decanted to yield an oil. The oil was dissolved in water, treated with 5 g of sodium perchlorate, and the precipitated perchlorate was isolated by filtration.

The above decanted organic solvent was concentrated, the residual chloride was triturated with 100 ml of methylene chloride, and the precipitated solid was filtered and converted to the perchlorate by treating with sodium perchlorate solution.

The combined perchlorate salt was crystallized from methanol to afford 12.2 g (38.7%) of 10-methoxybenzo[b]quinolizinium perchlorate (Formula IV: $R^1=R^7=H$; $R^2=10-OCH_3$; $X^-=ClO_4^-$).

Preparation 10

(a)

A mixture of pyridine-2-carboxaldehyde ethylene acetal (20 g; 0.13 mol), 4-methoxybenzyl chloride (21.2 g; 0.13 mol), and sulfolane (5 ml) in a 250 ml reaction flask was heated under nitrogen to 95° C. with stirring for 4 hours and then the mixture was allowed to react at room temperature overnight. The organic solvent was decanted, the resulting gummy precipitate was triturated with ethyl acetate :hexane (2:8), refluxed with stirring, and cooled. The solvent was decanted to yield 1-(p-methoxybenzyl)pyridine-2-carboxaldehyde ethylene acetal chloride (Formula IX: $R^1=R^7=H$; $R^2=4'-OCH_3$; $Z^-=Cl^-$).

(b)

Polyphosphoric acid (100 g) and 10 ml of methane sulfonic acid was heated to 95° C. with stirring and 12 g (28 mmol) of 1-(p-methoxybenzyl)pyridine-2-carboxaldehyde ethylene acetal chloride was added in portions during a 10 min. period for 3 hours. The reaction mixture was allowed to stand at room temperature overnight.

The reaction mixture was poured onto ice-water, potassium hexafluorophosphate was added, and the precipitated salt was filtered. The solid product was recrystallized from acetonitrile/water to afford 9-methoxybenzo[b]quinolizinium hexafluorophosphate (Formula IV: $R^1=R^7=H$; $R^2=9-OCH_3$; $X^-=PF_6^-$).

Alternatively, 9-methoxybenzo[b]quinolizinium hexafluorophosphate was prepared as follows:

(c)

1-(p-methoxybenzyl)pyridine-2-carboxaldehyde ethylene acetal chloride (10.0 g) was dissolved in water (100 mL) and was treated with potassium hexafluorophosphate (10.0 g). The precipitate which formed was collected by filtration and dried at 60° C. in vacuo to afford 9 g of 1-(p-methoxybenzyl)pyridine-2-carboxaldehyde ethylene acetal hexafluorophosphate (Formula X: $R^1=R^7=H$; $R^2=4'-OCH_3$; $X^-=PF_6^-$).

(d)

A mixture of polyphosphoric acid ( 100 g) and methanesulfonic acid (10 mL) was heated to 95 ° C. and 1-(p-methoxybenzyl)pyridine-2-carboxaldehyde ethylene acetal hexafluorophosphate (5.0 g) was added in portions. The mixture was heated for 1 hour, then allowed to stand overnight. Water (200 mL) was added to the reaction mixture, followed by potassium hexafluorophosphate (5.0 g) and then the mixture was diluted with additional water (200 mL). The precipitate which formed was collected by filtration to afford 5.4 g of 9-methoxybenzo[b]quinolizinium hexafluorophosphate (Formula IV: $R^1=R^7=H$; $R^2=9-OCH_3$; $X^-=PF_6^-$).

Preparation 11

(a)

To a solution of 3-methoxybenzyl alcohol (50.0 g) in ether (1.1 L) at −20° C. was added n-BuLi (76.0 mL, 10.0M hexanes) at such a rate as to maintain the internal reaction temperature below −10° C. The reaction mixture was then warmed to room temperature, stirred for 2 hours, cooled to 0° C. and tetramethylethylene diamine (42.0 g) was added. The mixture was cooled to −30° C. and then 2-pyridinecarboxaldehyde (58.0 g) was added over 5 minutes. The reaction mixture was warmed to 0° C. quenched with water (500 mL) and then cooled overnight. A precipitate formed which was collected by filtration, washed with ether, and recrystallized from ethanol to afford 30.0 g of α-[2-(hydroxymethyl)-6-methoxyphenyl]-2-pyridinemethanol (Formula XIII: $R^1=R^7=H$; $R^2=$6—$OCH_3$).

(b)

A mixture of 2-[2-(hydroxymethyl)-6-methoxyphenyl]-2-pyridinemethanol (20.0 g) and 45% hydrobromic acid in acetic acid (100 mL) was heated at 100° C. for 9 hours and then allowed to stand at room temperature overnight. The reaction mixture was concentrated in vacuo, and the residue was treated with 25% $NaClO_4$ in water (400 mL) and stirred for 15 minutes. The mixture was extracted with dichloromethane (6×200 mL), the organic layers were combined, dried over $Na_2SO_4$ and concentrated in vacuo. Ether was added to the residue and the mixture was sonicated. The product was collected by filtration and washed with dichloromethane to afford 5.6 g of 10-methoxybenzo[b]quinolizinium perchlorate (Formula IV: $R^1=R^7=H$; $R^2=$10—$OCH_3$; $X^-=ClO_4^-$).

Preparation 12

To α-[2-(hydroxymethyl)-6-methoxyphenyl]-2-pyridinemethanol (1.6 g) in benzene (70 mL) at 90° C. was added trifluoromethanesulfonic anhydride (6.47 g). The mixture was stirred for 30 minutes and the solvent was concentrated in vacuo. The residue was purified by column chromatography on silica eluting with 9%-10% methanol/$CH_2Cl_2$ and the chromatography solvent was removed in vacuo. The residue was dissolved in water (30 mL) and treated with $NaClO_4$ (3.0 g). The precipitate which formed was collected by filtration to afford 0.86 g of 10-methoxybenzo[b]quinolizinium perchlorate (Formula IV: $R^1=R^7=H$; $R^3=$10—$OCH_3$; $X^-=ClO_4^-$).

Preparation 13

Benzo[b]quinolizinium bromide (508.5 g, 1.95 mol) (Bradsher and Parham, J. Org. Chem. 1963, 28, 83–85, Example VIIa) was dissolved in distilled water (5 L) with heating and potassium hexafluorophosphate (367.2 g, 1.95 mol) in water (1.1 L) was added in portions. After the addition was complete, the mixture was stirred at ambient temperature for 3 hours, then at 0° C. for 1 hour. The mixture was filtered and washed with cold water to afford 601 g (94.8%) of benzo[b]quinolizinium hexafluorophosphate (Formula IV: $R^1=R^2=R^7=H$; $X^-=PF_6^-$).

Preparation 14

(a)

Following a procedure similar to that described in preparations 18a–b it is contemplated that there can be prepared 9-trichloromethylbenzo[b]quinolizinium hexafluorophosphate from p-trichloromethylbenzyl bromide and 2-(1,3-dioxolan-2-yl)pyridine.

(b)

Following a procedure similar to that described in preparations 21a–b it is contemplated that there can be prepared 4-bromobenzo[b]quinolizinium perchlorate from o-bromobenzyl alcohol, and 6-bromo-2-pyridine carboxyaldehyde.

Preparation 15

(a)

To a solution of 38.6 g (0.206 mol) of o-bromobenzyl alcohol in 400 ml of THF at −78° C. was added in dropwise portions 42 ml (0.42 mol) of 10M n-butyllithium solution in hexane and the mixture was stirred at −78° C. for 60 min. 2-Acetylpyridine (25 g; 0.206 mol) in 50 ml of THF was added to the above mixture while maintaining an internal temperature below −50° C., and the reaction mixture was stirred at this temperature for 30 min and then the resulting mixture was allowed to warm to room temperature.

The reaction mixture was quenched by an addition of 400 ml of saturated ammonium chloride solution with stirring and concentrated in vacuo. The residue was extracted with chloroform (3×), dried over sodium sulfate, the remaining liquid filtered and concentrated in vacuo to yield 21.3 g of 2-[1-hydroxy-1-methyl-(2′-hydroxymethyl)-benzyl]pyridine (Formula XII: $R^1=R^2=H$; $R^7=CH_3$ as a white solid, m.p. 172°–174° C.

(b)

A mixture of 9.1 g (39 mmol) of 2-[1-hydroxy-1-methyl-(2′-hydroxymethyl)-benzyl]pyridine in 150 ml (1.6 mol) of $POCl_3$ was heated with vigorous stirring at 105° C. for 6 hours and the reaction mixture was cooled to room temperature. A heterogeneous solution was poured into ice-water (1000 ml) with vigorous stirring, and 50 g of sodium perchlorate was added with stirring (10 min). A solid product was filtered, washed with water, ether, ethyl acetate, and dried to afford 4.5 g (38.8%) of methylbenzo[b]quinolizinium perchlorate (Formula IV: $R^1=R^2=H$, $R^7=CH_3$; $X^-=ClO_4^-$).

Preparation 16

(a)

2-methoxy-2-isopropyl-1,3-dioxane was prepared from 1,1,1-trimethoxy-isopropane (21.7 g; 0.146 mol) and propane-1,3-diol (10.1 g; 0.132 mol) according to a procedure similar to that described in preparation 3(d). The product was purified by distillation to afford 17.1 g (81%) of 2-methoxy-2-isopropyl-1,3-dioxane, as an oil, b.p. 78°–80° C./30 mm.

(b)

2-isopropylidene-1,3-dioxane was prepared from 2-methoxy-2-isopropyl-1,3-dioxane (17.1 g; 0.106 mol) and aluminum tri-t-. butoxide (26.2 g; 0.106 mol) according to a procedure similar to that described in preparation 3(e). The product was purified by distillation to afford 6.5 g (47.4%) of 2-isopropylidene-1,3-dioxane, (Formula V: $R^3=R^4=CH_3$; $R^5$ and $R^6$ together-=—$O(CH_2)_3O$—) as an oil, b.p. 70°–72° C./30 mm.

Preparation 17

A mixture of 1,1,1-triethoxy-isopropane (32.2 g; 0.144 mol) and aluminum tri t-butoxide (35.6 g; 0.144 mol) was healed with stirring to 100° C. quickly and then continuously heated slowly to 170°-180° C. and held at 170°-180° until distillation of t-butanol was completed. The fractional distillation head was then removed and replaced with a short path distillation head and distilled to yield 11.67 g of 1,1-diethoxy-2,2-dimethylethylene (Formula V: $R^3=R^4=CH_3$; $R^5=R^6=OC_2H_5$) containing 10-20% of ethyl 2-methyl-propionate.

Preparation 18

(a)

A mixture of 4.8 g (0.02 mol) of p-trifluoromethylbenzyl bromide and 3 g (0.019 mol) of 2-(1,3-dioxolan-2-yl)pyridine was allowed to stir at room temperature and then filtered. The solid residue was washed with ether and dried in vacuo to afford 6 g (76.9%) of 1-(p-trifluoromethylbenzyl)-2-(1,3-dioxolane-2-yl)pyridinium bromide (Formula IX: $R^1=R^7=H$; $R^2=4-CF_3$; $Z^-=Br^-$).

(b)

A mixture of 1-(p-trifluoromethylbenzyl-2-(1,3-dioxolan-2-yl)-pyridinium bromide (5 g; 0.0128 mol), polyphosphoric acid (50 g), and 5 g (0.052 mol) of methanesulfonic acid was heated to 110° C. The mixture was cooled, diluted with water, and an aqueous solution of 6 g of potassium hexafluorophosphate was added to the reaction mixture. The resulting solid product was filtered and dried to afford 3.05 g (61%) of trifluoromethylbenzo[b]quinolizinium hexafluorophosphate (Formula IV: $R^1=R^7=H$; $R^2=9-CF_3$; $X^-=PF_6^-$).

Preparation 19

(a)

A mixture of 5 g (0.024 mol) of 3,5-difluorobenzyl bromide and 3.6 g (0.024 mol) of 2-(2'-pyridyl)-1,3-dioxolane was allowed to stir at room temperature for 48 hours and then filtered. The reaction mixture was partitioned between water and ether, an aqueous phase was separated and treated with a solution of potassium hexafluorophosphate in water. The solid residue was filtered and dried in vacuo to afford 9 g (76.9%) of 1-(3,5-difluorobenzyl)-2-(1:3-dioxolan-2-yl)-pyridinium hexafluorophosphate.

(b)

A mixture of 1-(3,5-difluorobenzyl-2-(1,3-dioxolan-2-yl)pyridinium hexafluorophosphate (9 g; 0.021 mol), polyphosphoric acid (90 g), and 9 ml of methanesulfonic acid was heated at 110° C. for 7 hours and then stirred at room temperature overnight. The reaction mixture was poured into 200 ml of water and a warm solution of 9 g of potassium hexafluorophosphate in water was added with stirring. The resulting pale yellow solid product was filtered and dried to afford 6.5 g (86%) of 8,10-difluorobenzo [b]quinolizinium hexafluorophosphate (Formula IV: $R^1=R^7=H$; $R^2=8,10-F_2$; $X^-=PF_6^-$).

Preparation 20

(a)

A mixture of 47.6 g (0.289 mol) of p-chlorobenzyl chloride and 45 g (0.298 mol) of 2-(1,3-dioxolan-2-yl)-pyridine in 30 ml of sulfolane was heated on a steam bath for 4 hr. After adding an additional 4 g of p-chlorobenzyl chloride, the reaction mixture was heated on a steam bath for 12 hr and poured into 300 ml of ethyl acetate. Ethyl acetate was decanted, and an additional 200 ml of ethyl acetate was added to the residue with stirring (20 min) and decanted to remove excess 2-(1,3-dioxolan-2-yl)-pyridine and p-chlorobenzyl chloride. The ethyl acetate wash was repeated and then the brown residue was washed with 300 ml of ether to afford 92 g of 1-(p-chlorobenzyl)-2-(1,3-dioxolan-2-yl)-pyridinium chloride (Formula IX: $R^1=R^7=H$; $R^2=4-Cl$; $Z^-=Cl^-$).

(b)

A mixture of 1-(p-chlorobenzyl-2-(1,3-dioxolan-2-yl)pyridinium chloride and 300 ml of 48% HBr was heated at 100° C. for 24 hr, cooled, concentrated in vacuo, and poured into 50 g of ice. The resulting tan solid was filtered to afford 7.9 g of 9-chlorobenzo[b]quinolizinium chloride (Formula IV: $R^1=R^7=H$; $R^2=9-Cl$; $X^-=Cl^-$).

The aqueous layer was treated with sodium perchlorate solution in water and the resulting solid was cooled and filtered to afford 7.9 g (9%) of 9-chlorobenzo[b]quinolizinium perchlorate (Formula IV: $R^1=R^7=H$; $R^2=9-Cl$; $X^-=ClO_4^-$).

Preparation 21

(a)

To a mixture of 28.3 g (0.15 mol) of o-bromobenzyl alcohol in 1 L of ether cooled to $-20°$ C. was added in portions 32.5 ml (0.32 mol) of n-butyllithium (10M) in hexane over a 20 min period and the reaction mixture was stirred for 1 hr. The above reaction mixture was cooled to $-20°$ C., 19.9 g (0.165 mol) of 6-methyl-2-pyridinecarboxaldehyde was added to the mixture, and the resulting reaction mixture was allowed to warm to room temperature. After 1 hour, ammonium chloride solution was added to the mixture. The diol was extracted with ethyl acetate, washed with brine, the ethyl acetate phase was dried over sodium sulfate, and the solvent was removed in vacuo to afford 21.9 g (70.5%) of 2-[1-hydroxy-(2'-hydroxymethyl)-benzyl]-6-methyl-pyridine (Formula XIII: $R^1=6-CH_3$; $R^2=R^7=H$).

(b)

To a mixture of 10.34 g (0.05 mol) of 2-[1-hydroxy-(2'-hydroxymethyl) -benzyl]-6-methyl-pyridine in 200 ml of benzene heated to 80° C. was added in one portion 50 g (0.176) of trifluoromethanesulfonic anhydride, and the reaction mixture was allowed to react at 60° C. for 10 min, and then allowed to cool to room temperature. The reaction mixture was concentrated in vacuo and the residue was purified by chromatography on silica eluting with 9% methanol/chloroform to yield a pale yellow solid. This solid was dissolved in water and reacted with excess sodium perchlorate. The solid product was filtered, washed with water, and dried to afford 5.54 g (combined yield 37%) of 4-methylbenzo[b]quinolizinium perchlorate (Formula IV: $R^1=4CH_3$; $R^2=R^7=H$; $X^-=ClO_4^-$), as a yellow solid, m.p. 160°-165° C.

Preparation 22

To a mixture of 89.3 g (0.796 mol) of potassium t-butoxide in 300 ml of THF at room temperature was added dropwise over a 30 min period 131 g (0. 664 mol) of 1-bromo-2,2-diethoxyethane and the reaction mixture was allowed to reflux for 1 hr and then cooled. The solvent was removed in vacuo and the product was distilled to afford 47.8 g (62%) of 1,1-diethoxyethylene (Formula V: $R^3=R^4=H$; $R^5=R^6=OC_2H_5$), as a colorless oil, b.p. 65°–75° C./100 mm.

Preparation 23

To 8.22 g (0.0316 mol) of benzo[b]quinolizinium bromide was added with cooling in an ice-bath 24.4 ml (0.474 mol) of bromine and the reaction mixture was allowed to stand at room temperature 24 hr. The reaction mixture was poured into ethyl acetate, refrigerated at −15° C. for 24 hr, and the resulting solid was filtered. The solid product was washed with ethyl acetate, dissolved in boiling methanol/acetone (1:1), refluxed for 15 min, and the solution was concentrated in vacuo to yield a white solid. The solid was stirred at room temperature with 400 ml of water and sodium acetate for 24 hr and filtered. The red filtrate was treated with sodium perchlorate (15 g) and a resulting yellow solid was filtered. The solid product was dissolved in methylene chloride/ethyl acetate (1:1) and the methylene chloride was distilled (⅓ of the original volume) in vacuo. The reaction mixture was cooled and the solid product was filtered to afford 3.6 g (32.3%) of 10-bromobenzo[b]quinolizinium perchlorate (Formula IV: $R^1=R^7=H$; $R^2=10$—Br; $X^-=ClO_4^-$), m.p. 112°–115° C.

Preparation 24

(a)

To a mixture of 15.0 g (0.098 mol) of 3,4-methylenedioxybenzyl alcohol in 250 ml of ether cooled to −20° C. was added in portions 21.1 ml (0.211 mol) of n-butyllithium (10M) in hexane over a 10 min period, and the reaction mixture was allowed to warm to room temperature and stirred 1 hr. The above reaction mixture was cooled to −20° C., 11.18 ml (0.117 mol) of 2-pyridinecarboxaldehyde was added to the mixture, and the resulting reaction mixture was allowed to warm to room temperature. Ammonium chloride solution (70 ml) was added to the mixture and the mixture was extracted with methylene chloride (3×150 ml). The organic layer was washed with brine, dried over sodium sulfate, and concentrated. The diol was purified by chromatography on silica eluting with ethyl acetate/hexane (9:1). The diol was triturated with ether and filtered to afford 8.8 g (34.7%) of 2-[1-hydroxy-(6'-hydroxymethyl-2',3'-methylenedioxy)benzyl]pyridine (Formula XIII: $R^1=R^7=H$; $R^2=2',3'$ (—OCH$_2$O—), as a white solid, m.p. 98°–101° C.

(b)

To a mixture of 2 g (0.0077 mol) of 2-[1-hydroxy-(6'-hydroxymethyl-2',3'-methylenedioxy)benzyl]pyridine in 80 ml of benzene heated to 50° C. was added in one portion 7.64 g (0.027 mol) of trifluoromethanesulfonic anhydride, and the mixture was allowed to cool to room temperature and stirred for 30 min. The reaction mixture was concentrated in vacuo and the residue was purified by chromatography on silica eluting with 10% methanol/methylene chloride to yield a red solid. This solid was dissolved in water and reacted with excess sodium perchlorate. The solid product was filtered, washed with water, and dried to afford 0.069 g (2.4%) of 9,10-methylenedioxybenzo[b]quinolizinium perchlorate (Formula IV: $R^1=R^7=H$; $R^2=2',3'$ (—OCH$_2$O—); $X^-=ClO_4^-$), as an orange solid, m.p. 220°–224° C.

Preparation 25

(a)

To a mixture of 5 g (0.0361 mol) of 3-methoxybenzyl alcohol in 150 ml of ether cooled to −20° C. was added in portions 7.7 ml (0.077 mol) of n-butyllithium (10M) in hexane over an 8 min period, and the reaction mixture was allowed to warm to room temperature and stirred 1 hr. The above reaction mixture was cooled to −20° C., 4.8 ml (0.043 mol) of 2-acetylpyridine was added to the mixture, and the resulting reaction mixture was allowed to warm to room temperature and stirred 1 hr. Ammonium chloride solution (50 ml) was added to the mixture and the mixture was extracted with ethyl acetate (3×100 ml). The organic layer was washed with brine, dried over sodium sulfate, and concentrated. The diol was purified by chromatography on silica gel eluting with ethyl acetate/hexane (8:2) to afford 3.2 g (34.4%) of 2-[1-hydroxy-1-methyl (6'-hydroxymethyl-2'-methoxy)benzyl]pyridine (Formula XIII: $R^1=H$; $R^2=2'$—OCH$_3$; $R^7=CH_3$), as a yellow oil.

(b)

To a mixture of 2 g (0.0077 mol) of 2-[1-hydroxy-1-methyl (6'-hydroxymethyl-2'-methoxy)benzyl]pyridine in 60 ml of benzene heated to 50° C. was added in one portion 4.89 g (0.027 mol) of trifluoromethanesulfonic arthydride, and the mixture allowed to cool to room temperature and stirred for 30 min. The reaction mixture was concentrated in vacuo and the residue was purified by chromatography on silica gel eluting with 5% methanol/methylene chloride and 10% methanol/methylene chloride. The second fraction was concentrated in vacuo, the residue was dissolved in water and heated to reflux, and reacted with excess sodium perchlorate. The solid product was filtered and dried to afford 0.1 g (6.3%) of 10-methoxy-11-methylbenzo[b]quinolizinium perchlorate (Formula IV: $R^1=1$; $R^2=10$—OCH$_3$; $R^7=CH_3$; $X^-=ClO_4^-$), as an orange solid, m.p. 208°–212° C.

Preparation 26

(a)

To a mixture of 3.59 g (0.019 mol) of o-bromobenzyl alcohol in 100 ml of ether cooled to −20° C. was added in portions 4.1 ml (0.0412 mol) of n-butyllithium (10M) in hexane over a 6 min period, and the reaction mixture was stirred 20 min. The above reaction mixture was cooled to −20° C., 3 g (0.021 mol) of 3-methoxy-pyridine-2-carboxaldehyde in 5 ml of THF was added in one portion to the mixture, and the resulting reaction mixture was allowed to warm to room temperature and stirred for 20 min. Ammonium chloride solution (30 ml) was added to the mixture and the mixture was extracted with ethyl acetate (3×50 ml). The organic layer was washed with brine, dried over sodium sulfate, and concentrated. The diol was triturated with 100 ml of ether, filtered, and purified by chromatography on silica gel eluting with 4% methanol/hexane. The solvent was concentrated in vacuo to afford 0.68 g (14.5%) of 2-[1-hydroxy-(2'-hydroxymethyl)benzyl]-3-methoxypyridine (Formula XIII: $R^1=3$—OCH$_3$; $R^2=R^7=H$), as a white solid, m.p. 138°–140° C.

(b)

To a mixture of 0.61 g (0.00248 mol) of 2-[1-hydroxy-(2'-hydroxymethyl)-benzyl]-3-methoxypyridine in 50 ml of benzene heated to 50° C. was added in one portion 2.11 g (0.0074 mol) of trifluoromethanesulfonic anhydride, and the mixture was allowed to cool to room temperature and stirred for 30 min. The reaction mixture was concentrated in vacuo and the residue was purified by chromatography on silica gel eluting with 5% methanol/methylene chloride and 10% methanol/methylene chloride. The second fraction was concentrated in vacuo, the residue was dissolved in hot water (20 ml), heated to reflux, and treated with the excess sodium perchlorate. The solid product was filtered, washed with water, and dried to afford 0.27 g (18.2%) of 1-methoxybenzo[b]quinolizinium perchlorate (Formula IV: $R^1=1-OCH_3$; $R^2=R^7=H$; $X^-=ClO_4^-$), as a yellow solid, m.p. 143°–145° C.

Preparation 27

(a)

To a mixture of 30 g (0.18 mol) of 3-isopropoxybenzyl alcohol in 600 ml of ether cooled to $-20°$ C. was added in portions 38.7 ml (0.387 mol) of n-butyllithium (10M) in hexane over a 20 min period, and the reaction mixture was allowed to warm to room temperature and stirred for 2 hr. The above reaction mixture was cooled to $-20°$ C., 23.1 g (0.216 mol) of pyridine-2-carboxaldehyde was added in one portion to the mixture, and the resulting reaction mixture was allowed to warm to room temperature and stirred for 1 hr. Ammonium chloride solution (200 ml) and 100 ml of ethyl acetate were added to the mixture. The resulting mixture was separated, the aqueous layer was extracted with methylene chloride (2×200 ml), the combined organic layer was washed with brine, dried over sodium sulfate, and concentrated. The diol was purified by chromatography on silica gel eluting with ethyl acetate/hexane (9:1; and 0.05% TEA). The solvent was concentrated in vacuo, the brown oil was dissolved in methylene chloride/hexane, and removal of methylene chloride in vacuo to ½ of its volume afforded 11.1 g (22.6%) of 2-[1-hydroxy-(6'-hydroxymethyl-2'-isopropoxy)-benzyl]-pyridine (Formula XIII: $R^1=R^7=H$; $R^2=2'-OCH(CH_3)_2$), as a tan solid.

(b)

To 11.1 g (0.0406 mol) of 2-[1-hydroxy-(6'-hydroxymethyl-2'-isopropoxy)-benzyl]pyridine was added 25 ml of POCl₃ in 1 min, the mixture was heated at 110° C. for 5 min and then cooled. The reaction mixture was concentrated in vacuo, 100 ml of toluene was added and concentrated to yield an oil which is insoluble in methylene chloride. Water and sodium perchlorate were added to the above oil, water was decanted, and the residue was dried under diminished pressure to yield a foam. The foam was dissolved in methanol/water, potassium hexaflurophosphate was added, and the mixture was heated on a steam-bath and then cooled. The aqueous mixture was concentrated in vacuo, the residue was dissolved in methylene chloride/methanol, cooled and filtered. Potassium perchlorate was removed by filtration, the filtrate was concentrated in vacuo to 10 ml of its volume, ethyl acetate was added and the mixture was cooled. The product was filtered to afford 5.32 g (34.3%) of 10-isopropoxybenzo[b]quinolizinium hexafluorophosphate (Formula IV: $R^1=R^7=H$; $R^2=10-OCH(CH_3)_2$; $X^-=PF_6^-$), as an orange solid.

Preparation 28

(a)

A mixture of 2-(1,3-dioxolan-2-yl)-pyridine (48.7 g; 0.322 mol) and p-bromobenzyl-bromide (80.52 g; 0.322 mol) in 60 ml of sulfolane was heated on a steam-bath (after 1 hr a red precipitate forms) for 3 hr. After cooling, 300 ml of ethyl acetate was added to the mixture, sonicated for 30 min, filtered, and the solid was dried to yield 110 g (85.2%) of bromobenzyl-2-(1:3-dioxolan-2-yl)pyridinium bromide (Formula IX: $R^1=R^7=H$; $R^2=4-Br$; $Z^-=Br^-$).

(b)

A mixture of 55 g (0.137 mol) of 1-(p-bromobenzyl)-2-(1,3-dioxolan-2-yl)pyridinium bromide and 300 g of 48 % HBr was heated to 100° C. for 24 hr and then cooled. The reaction mixture was poured into 250 g of ice and the resulting yellow precipitate was filtered and dried in vacuo (at 45 ° C.) to afford 32.85 g (70.8%) of 9-bromobenzo[b]quinolizinium bromide (Formula IV: $R^1=R^7=H$; $R^2=9-Br$; $X^-=Br^-$).

Preparation 29

To 500 ml of ammonia at $-40°$ C. was added 100 mg of ferric chloride hexahydrate, and 12.5 g (0.32 mol) of potassium (washed with hexane) in portions, and then 100 g (0.768 mol) of 2-propenyl-carboxyaldehyde-diethylacetal in 100 ml of ether was added dropwise and stirred at $-40°$ C. for 2.5 hr. The mixture was warmed, allowing ammonia to evaporate. Ether (100 ml) was added to the mixture, the mixture was filtered (the solid residue in hexane was quenched with isopropanol), the filtrate was concentrated and fractionally distilled to afford 46.05 g (42%) of 2-methyl-1,1-diethoxyethylene (Formula V: $R^3=CH_3$; $R^4=H$; $R^5=R^6=OC_2H_5$), as a clear liquid, 65°–68° C., at 55 mm.

Preparation 30

To 300 ml of ammonia at $-35°$ C. was added 3 g of potassium and 50 mg of ferric chloride hexahydrate, and then 15 g (0.087 mol) of isopropenyl-carboxyaldehyde-dipropylacetal in 75 ml of ether and stirred at $-35°$ C. for 120 hours. The dry-ice condenser and the bath were allowed to warm up (to 29° C.) gradually and ½ of the ammonia was allowed to evaporate. The reaction mixture was cooled to $-35°$ C., ether was added, the mixture was allowed to warm up to room temperature, and then stirred 1 hr. The mixture was filtered (the residue in hexane was quenched with isopropanol), the filtrate was concentrated and distilled to afford 11 g (73.3%) of 2,2-dimethyl-1,1-dipropoxyethylene (Formula V: $R^3=R^4=CH_3$; $R^5=R^6=OC^3H_7$), a clear liquid, b.p. 71°–85° C./26mm.

Preparation 31

To a solution of dichloroacetaldehyde diethylacetal (25 g; 0.1336 mol) in 150 ml of THF cooled to 0° C. was added 17.99 g (0.16 mol) of potassium t-butoxide in 50 ml of THF. The ice-bath was removed, and the reaction mixture was allowed to reflux for 16 hr and cooled. The reaction mixture was filtered (through celite) and a pale yellow solution was concentrated in vacuo at 30° C. The residue was distilled to afford 18.1 g (90%) of 2-chloro-1,1-diethoxyethylene (Formula V: $R^3=Cl$;

$R^4=H$; $R^5=R^6=OC_2H_5$), a colorless liquid, b.p. 70°–76° C./20–25 mm.

Preparation 32

(a)

To a solution of 2-(diphenylphosphinyl)-4R,6R-dimethyl-1,3-dioxane (3.15 g, 0.01 mol) in THF/ether (3/1, 200 mL) at −100° C. was added lithium diisopropylamide prepared from diisopropylamine (1.54 mL) and n-BuL: (5.5 mL, 2M in pentane), followed by acetone (0.734 mL, 0.01 mol). The mixture was stirred for 5 minutes, water (40 mL) was added and the mixture was warmed to room temperature. $K_2CO_3$ was added, the organic layer was separated, the aqueous layer was extracted with ether and the combined organic layers were washed with brine and dried over $Na_2SO_4$. The solvent was removed in vacuo and the residue was purified by column chromatography on silica gel eluting with ethyl acetate to afford 1.29 g of 2-(diphenylphosphinyl)-2-(1,1-dimethyl-1-hydroxymethyl)4R,6R-dimethyl-1,3-dioxane.

(b)

To a mixture of 1.28 g (0.0034 mol) of 2(diphenylphosphinyl) -2-(1,1-dimethyl-1-hydroxymethyl)-4R,6R-dimethyl-1,3-dioxane in 40 ml of THF at room temperature was added 410 mg (0.0037 mol) of potassium-t-butoxide in 10 ml of THF. The resulting pale yellow mixture was sonicated for 5 min and then stirred 1 hr. The reaction mixture was concentrated in vacuo, hexane was added to the residue, and the mixture was centrifuged. The solid residue was washed again with hexane and the mixture was centrifuged. The combined hexane solution was filtered (through celite) and concentrated to afford 0.45 g (84%) of (2-isopropylidene-4R,6R-dimethyl-1,3 dioxane (Formula V: $R^3=R^4=CH_3$; $R^5$ and $R^6$ together=(R,-R)—$OCH(CH_3)CH_2CH(CH_3)O-$), as a colorless liquid.

Preparation 33

(a)

A mixture of 2-(1,3-dioxolan-2-yl)pyridine (36.4 g, 0.24 mol), 4-nitrobenzytbromide (51.84 g, 0.24 mol) and sulfolane (50 mL) was heated on a steam bath for 10 hours. The mixture was cooled, ethyl acetate (300 mL) was added and the mixture was heated to 60° C. A precipitate formed which was collected by filtration to afford 1-(p-nitrobenzyl)-2-1,3-dioxolan-2-yl) pyridinium bromide (Formula IX: $R^1=R^7=H$; $R^2=4—NO_2$; $Z^-=Br^-$).

(b)

To a mixture of polyphosphoric acid (250 ml) and methanesulfonic acid (55 ml) heated to 100° C. with stirring was added 71 g (0.193 mol) of 1-(p-nitrobenzyl)-2-(2'-1',3'-dioxolane)pyridinium bromide and the resulting mixture was heated to 110° C. for 4 hr and cooled. The reaction mixture was poured into 500 g of ice, activated charcoal was added to the mixture, filtered, and sodium perchlorate solution added. The mixture was extracted with methylene chloride (2×500 ml), and the organic layer was concentrated to afford 5.2 g (8.3%) of 9-nitrobenzo[b]quinolizinium perchlorate (Formula IV: $R^1=R^7=H$; $R^2=9—NO_2$; $X^-=ClO_4^-$), as a brown solid.

Preparation 34

(a)

To a mixture of 12.49 g (0.0621 mol) of o-bromo-m-methylbenzyl alcohol in 400 ml of ether cooled to −20° C. was added in portions 13.3 ml (0.1335 mol) of n-butyllithium (10M) in hexane over a 20 min period, and the reaction mixture was allowed to warm to room temperature and stirred 1 hr. The above reaction mixture was cooled to −20° C., 14.63 g (0.136 mol) of pyridine-2-carboxaldehyde in 50 ml of ether was added to the mixture over an 1 hr period (the mixture turns purple), and the resulting reaction mixture was allowed to warm to room temperature and stirred for 1 hr. Ammonium chloride solution (100 ml) and 200 ml of ethyl acetate were added to the mixture with stirring, and the mixture was extracted with ethyl acetate (2×200 ml). The combined organic layer was washed with brine, dried over sodium sulfate, and concentrated. The diol was was triturated with 100 ml of ether, filtered, and the solid product was washed with hexane (yield: 6.6 g; 46%) to afford 2-[1-hydroxy-(2'-hydroxymethyl-6'-methyl)-benzyl]-pyridine (Formula XIII: $R^1=R^7=H$; $R^2=6'—CH_3$), as a pale yellow solid, m.p. 129°–132° C.

(b)

To a mixture of 3 g (0.013 mol) of 2-[1-hydroxy-(2'-hydroxymethyl-6'-methyl)-benzyl]-pyridine in 100 ml of benzene heated to 40° C. was added in one portion 12.96 g (0.0458 mol) of trifluoromethanesulfonic anhydride, and the mixture was allowed to cool to room temperature and stirred for 30 min. The reaction mixture was concentrated in vacuo and the residue (a red oil) was purified by chromatography on silica eluting with 9% methanol/methylene chloride. The eluent was concentrated in vacuo, the residue was dissolved in water (60 ml), heated to reflux, and reacted with 3 g of sodium perchlorate with stirring. The yellow solid product was filtered, washed with water,and dried to afford 0.926 g (24.4%) of 10-methylbenzo[b-]quinolizinium perchlorate (Formula IV: $R^1=R^7=H$; $R^2=10—CH_3$; $X^-=ClO_4^-$), as a pale yellow solid, mp 163°–166° C.

Preparation 35

A mixture of 40.27 g (0.275 mol) of 1,1-dimethyl-2,2-diethoxyethane and 0.2 g of 85% $H_3PO_4$ equipped with Vigreux distilling column was heated at 113°–150° C. maintaining the column head temperature of 72°–84° C. The distilled product was washed with 50 ml of 5% potassium carbonate solution (2×), dried over potassium carbonate, filtered, and distilled to afford 8.15 g (29.5%) of 2,2-dimethyl-1-ethoxyethylene (Formula V: $R^3=R^4=CH_3$; $R^5=OC_2H_5$; $R_6=H$), as a clear colorless liquid, b.p. 89°–95° C.

Preparation 36

(a)

To a mixture of 10 g (0.059 mol) of 2,5-dimethoxybenzyl alcohol in 250 ml of ether cooled to −20° C. was added in portions 12.75 ml (0.127 mol) of n-butyllithium (10M) in hexane over a 10 min period, and the reaction mixture was allowed to warm to room temperature and stirred 1 hr. The above reaction mixture was cooled to −20° C., 7.58 g (0.07 mol) of pyridine-2-carboxaldehyde was added to the mixture, and the resulting reaction mixture was allowed to warm to room temperature (a brown precipitate formed) and stirred for 1 hr. Ammonium chloride solution (60 ml) was added, the mixture was extracted with ethyl acetate, the combined organic layer was washed with brine, dried over sodium sulfate, and concentrated. The diol was purified by chromatography on silica eluting with ethyl acetate/hexane (9:1) to afford 1.7 g (10.5%) of 2-[(2',5'-dimethoxy-6'-hydroxymethyl)benzyl]pyridine (Formula XIII: $R^1=R^7=H$; $R^2=2',5'(OCH_3)_2$), as a white solid, m.p. 102°–104° C.

(b)

To a mixture of 1.25 g (0.045 mol) of 2-[(2',5'-dimethoxy-6'-hydroxymethyl)-benzyl]pyridine in 60 ml of benzene heated to 50° C. was added in one portion 4.5 g (0.0159 mol) of trifluoromethanesulfonic anhydride, and the mixture was allowed to cool to room temperature and stirred for 30 min. The reaction mixture was concentrated in vacuo and the residue (an oil) was purified by chromatography on silica gel eluting with 10% methanol/methylene chloride. The eluent was concentrated in vacuo, the residue was dissolved in water (30 ml), heated to reflux, and reacted with excess sodium perchlorate with stirring and then cooled (using ultrasound and ice). The orange solid product was filtered, washed with water (4 ml), and dried in vacuo to afford 0.42 g (27.6%) of 7,10-dimethoxybenzo[b]quinolizinium perchlorate (Formula IV: $R^1=R^7=H$; $R^2=7,10$—$(OCH_3)_2$; $X^-=ClO_4^-$), as an orange solid, m.p. 235°–240° C.

Preparation 37

(a)

To a mixture of 10.2 g (0.052 mol) of 1,1-dimethoxy-2-bromo-isobutane and 5 g (0.55 mol) of butane-2R,3R-diol was added 100 mg of PPTSA and toluene, and the mixture (equipped with Dean-Stark trap) was allowed to reflux 16 hr while distilling toluene (120 ml). The reaction mixture was cooled, 30 ml of 10% potassium carbonate solution was added to the mixture, and the mixture was extracted with ether (3×75 ml). The organic layer was washed with brine, dried over sodium sulfate, and filtered. The filtrate was concentrated and an oil distilled to afford 7.6 g (65%) of 2-[(2-bromoisopropyl)]-(4R,5R-dimethyl)-1,3-dioxolane, as a colorless liquid, b.p. 73°–77° C./14 mm.

(b)

To a solution of 1.5 g (0.0067 mol) of 2-[(2-bromoisopropyl) ]-(4R,5R-dimethyl)-1,3-dioxolane in 40 ml of THF at room temperature was added with stirring 1.35 g (0.0121 mol) of potassium t-butoxide and the mixture was stirred for 16 hr at room temperature. The mixture was filtered through celite with ether and the filtrate was concentrated in vacuo (<30° C.) and the resulting 2-isopropylidene-4R,5R-dimethyl-1,3-dioxolane (Formula V: $R^3=R^4=CH_3$; $R^5$ and $R^6$ together=(R,-R)—$OCH(CH_3)CH(CH_3)O-$) was used without additional purification.

Preparation 38

To a mixture of 250 ml of ether, 100 g of 3 A° molecular sieves, 50 g sodium sulfate, and 125.9 g (1.72 mol) of N,N-diethylamine cooled to −10° C. was added dropwise (under −5° C.) with stirring 50 g (0.86 mol) of propionaldehyde. The reaction mixture was allowed to stand in a freezer for 12 hr. The light tan solution was filtered, the filtrate was concentrated to remove ether, and the residue distilled through a Vigreux distillation column was heated to remove diethylamine and to collect liquid distilling at 40°–100° C./10–30 mm-aspirator. The liquid was redistilled to afford 46.1 g (47%) of 1-diethylamino propene (Formula V: $R^3=CH_3$; $R^4=H$; $R^5=N(C_2H_5)_2$; $R^6=H$), as a clear liquid, b.p. 40° C./25 mm.

Preparation 39

A mixture of 3-methoxybenzylchloride (5.0 g, 0.032 mol) and 2-(1,3-dioxolan-2-yl) pyridine (5.0 g, 0.032 mol) was stirred at room temperature for 5 days, then at reflux for 1 day. HCl (50 mL) was added and the mixture was heated for 3 more days. The mixture was cooled, the solvent was removed in vacuo and the residue was diluted with water and treated with $KPF_6$ (7.0 g) in water. A precipitate formed, which was collected by filtration. The solid product was purified by column chromatography on silica eluting with acetonitrile/$CH_2Cl_2$ (⅛), followed by slurrying the product in hot methanol and then collecting the product by filtration to afford 1.0 g of 8-methoxybenzo[b]quinolizinium hexafluorophosphate (Formula IV: $R^1=R^7=H$; $R^2=8$—$OCH_3$; $X^-=PF_6^-$).

Preparation 40

(a)

p-Toluenesulfonic acid (1.14 g, 0.006 mol) was added to a mixture of methacrolein (42.35 g, 0.06 mol), ethanol (141.9 mL), $CH_2Cl_2$ (120 mL) and triethylorthoformate (130.6 mL, 0.785 mol). The mixture was stirred at room temperature for 3 days and then $K_2CO_3$ (2 g) was added. The mixture was stirred for 10 minutes, filtered, and then the filtrate was concentrated in vacuo. The residue was purified by distillation through a Vigreaux column at 130° C. to afford 35 g of methacrolein diethylacetal.

(b)

To ammonia (500 mL) at −35° C. was added $FeCl_3 \cdot 6H_2O$ (0.1 g), then potassium metal (24.26 g), and then methacrolein diethylacetal (109 g, 0.756 mol) in ether (150 mL). The mixture was stirred at −35° C. for 3 days, then the ammonia was evaporated, additional ether (100 mL) was added and stirring was continued for another day. The mixture was filtered and the filtrate was distilled at 65° C. and 55 mm Hg to afford 46.05 g of 1,1-diethoxy-2,2-dimethylethylene (Formula V: $R^3=R^4=CH_3$; $R^5=R^6=OC_2H_5$).

Preparation 41

(a)

To triethyl orthoformate (162.1 mL, 0.974 mol) was added dropwise over 1.5 hours chlorodiphenylphosphine (175 mL, 0.974 mol) while maintaining the reaction temperature below 70° C. When the addition is complete, the temperature is allowed to increase to 110° C. and is maintained at that temperature for 3 hours. The mixture is cooled, hexane is added, the mixture is filtered and the filtrate is concentrated in vacuo. The residue is taken up in water, extracted with $CH_2Cl_2$ and dried over $MgSO_4$. The solvent is concentrated to 700 mL, the mixture is cooled, filtered and the filtrate is treated with hexane. The $CH_2Cl_2$ is removed and the hexane layer is cooled. A precipitate formed which was collected by filtration to afford 133 g of 1-(diphenylphosphinyl)-1,1-diethoxymethane.

(b)

To 1-(diphenylphosphinyl)-1,1-diethoxymethane (20 g) in THF (600 mL)/ether (200 mL) at −95° C. was added lithium diisopropylamide (prepared from diisopropylamine (11.5 mL) and nBuLi (7.8 mL, 0.0788 mol), followed by acetone (9.6 mL). The mixture was stirred for 30 minutes, water (100 mL) was added and then after warming the mixture to room temperature K$_2$CO$_3$ was added (4 g). The mixture was extracted with ethyl acetate (2×200 mL), the combined organic layers were washed with brine and dried over Na$_2$SO$_4$. The solvent was removed in vacuo and the residue was purified by column chromatography on silica gel eluting with ethyl acetate/0.5% triethylamine to afford 1-(diphenylphosphinyl)-1-(1,1-dimethyl-1-hydroxymethyl)-1,1-diethoxymethane.

(c)

To a solution of the compound of preparation 41(b) (2.3 g, 0.02 mol) in THF (50 mL) was added potassium t-butoxide (2.3 g, 0.02 mol). The mixture was stirred at room temperature for 1 hour, then hexane (20 mL) was added. The mixture was filtered through celite, the filtrate was concentrated in vacuo, and the residue was distilled at 50 mmHg to afford 2.1 g of 1,1-diethoxy-2,2-dimethylethylene (Formula V: $R^3=R^4=CH_3$; $R^5=R^6=OC_2H_5$).

Preparation 42

(a)

A mixture of 4-methyl-2-pyridine carboxaldehyde (1.0 g, 8.26 mmol), sulfolane (10 ml) and benzyl bromide (0.98 ml, 8.3 mmol) was stirred at room temperature for 16 hours, then was heated on a steam bath for 16 hours. Several portions of ethyl acetate were added to the reaction mixture and subsequently decanted to yield a residual gum. The gum was dissolved in water, washed with ether and evaporated to dryness to afford crude formyl-4-methyl pyridinium bromide.

(b)

A mixture of 1-benzyl-2-formyl-4-methyl pyridinium bromide, and 48% HBr (50 ml) was heated at 100° C. for 16 hours. The solvent was removed in vacuo, water (20 ml) was added and the mixture was poured into a solution of NaClO$_4$ (6.0 g) in water (100 ml). A precipitate formed, which was collected by filtration and purified by column chromatography on silica gel eluting with CH$_2$Cl$_2$/methanol (1:1) to afford 2-methylbenzo[b]quinolizinium perchlorate.

Preparation of Final Products

Example 1

(a)

A mixture of benzo[b]quinolizinium bromide (1.0 g, 3.8 mmol), 1,1-diethoxy-2,2-dimethylethylene (15.0 mL, as a 50% mixture with methacrolein diethylacetal) and acetonitrile (30 mL) was stirred at room temperature for 72 hours. The reaction mixture was filtered, and the solvent was removed in vacuo. The residue was taken up in acetonitrile, treated with charcoal, filtered and concentrated in vacuo. Water was added to the residue, followed by sodium perchlorate (0.3 g, 4.8 mmol). A precipitate formed which was collected by filtration and dried at 40° C. in high vacuum to afford 12,12-diethoxy-13,13-dimethyl-6,11-ethano-6,11-dihydrobenzo[b]quinolizinium perchlorate [Formula I: $R^1=R^2=R^7=H$, $R^3=R^3=CH_3$, $R^5=R^6=OC_2H_5$, and $X^-=ClO_4^-$], as a white solid, m.p. 67.0°–72.0° C.

(b)

Alternatively, the above reaction was also performed as described hereinbelow. A mixture of benzo[b]quinolizinium perchlorate (78 g, 0.279 mol), 1,1-diethoxy-2,2-dimethylethylene (93 g, 0.47 mol) and acetonitrile (780 mL) were refluxed for hours. After cooling the mixture to room temperature, the solvent was removed under reduced pressure and the residual material was dissolved in ethyl acetate (2 L) and treated with charcoal (150 g). The charcoal was removed by filtration, the filtrate was washed with water (1 L), and the organic solvent was dried over MgSO$_4$ and removed in vacuo. The crude product thus obtained (111 g, 93.9%) was recrystallized from hot-isopropano (800 mL) to afford 100 g (84.6%) of 12,12-diethoxy-13,13-dimethyl-6,11-ethano-6,11-dihydrobenzo[b]quinolizinium perchlorate [Formula I: $R^1=R^2=R^7=H$; $R^3=R^4=CH_3$; $R^5=R^6=OC_2H_5$; and $X^-=ClO_4^-$].

Example 2

A column of Dowex ® 1×2-200 ion-exchange resin was eluted with 0.5N HCl until the eluant was clear, and was then washed with distilled water until a pH of about 6.5–7.5 was obtained. 12,12-Diethoxy-13,13-dimethyl-6,11-ethano-6,11-dihydrobenzo[b]quinolizinium perchlorate (1.4 g, 3.3 mmol) was dissolved in ethyl acetate (60 mL) and loaded onto the ion-exchange column. The column was eluted with water (3 L) and the solvent was removed in vacuo to afford 12,12-diethoxy-13,13-dimethyl-6,11-ethano-6,11-dihydrobenzo[b]quinolizinium chloride-¼ H$_2$O [Formula I: $R^1=R^2=R^7=H$; $R^3=R^4=CH_3$; $R^5=R^6=OC_2H_5$; and $X^-=Cl^-$] as an off-white solid. Two additional ion-exchange resin columns on 4.44 g and 4.0 g, respectfully, afforded a total of 5.53 g of the desired product.

Example 3

A mixture of benzo[b]quinolizinium hexafluorophosphate (460 g, 1.4 mol) in acetonitrile (1.84 L) was heated on a steam bath until a solution resulted, and 1,1-diethoxy-2,2-dimethylethylene (46.2 g, 2.12 mol) was added. The mixture was heated to reflux for 4 hours, and then stirred at room temperature for 16 hours. The solvent was removed in vacuo, the residue was dissolved in ethyl acetate (14 L) and stirred with water (5 L). The solution was decolorized with charcoal, dried over MgSO$_4$ and concentrated in vacuo to afford an off-white solid. The solid was slurried with isopropanol (5.5 L), heated to reflux, and then stirred at room temperature for 16 hours. The solution was cooled in an ice-bath and the product was collected by filtration and dried in high vacuum to afford 627 g (94.5%) of 12,12-diethoxy-13,13-dimethyl-6,11-ethano-6,11-dihydrobenzo[b]quinolizinium hexafluorophosphate [Formula I: $R^1=R^2=R^7=H$; $R^3=R^4=CH_3$; $R^5=R^6=OC_2H_5$; and $X^-=PF_6^-$] as a white solid, m.p. 165°–167° C. when recrystallized from isopropanol.

Example 4

The potassium salt of (1S)-(−)-camphanic acid (1.11 g, 4.7 mmol) was dissolved in isopropanol (70 mL) with heating and a solution of 12,12-diethoxy-13, 13-dimethyl-6,11-ethano-6,11-dihydrobenzo[b]quinolizinium chloride (1.69 g, 4.7 mmol) in isopropanol (20 mL) was added over three minutes. The reaction mixture was stirred for 2 hours, the precipitate which formed was removed by filtration, and the filtrate was concentrated in vacuo to afford 2.5 g of crude 12,12-diethoxy-13,13-dimethyl-6,11-ethano-6,11-dihydrobenzo[b]quinolizinium camphanate [Formula I: $R^1=R^2=R^7=H$; $R^3=R^4=CH_3$; $R^5=R^6=OC_2H_5$; and $X^-=(1S)$-(−)-$C_{10}H_{13}O_4^-$]. The crude product was dissolved in $CH_2Cl_2$ (200 mL), washed with water, and the organic layer was concentrated in vacuo. The residue was recrystallized from isopropyl acetate (20 mL) to afford 0.67 g (27%) of purified product, as a white solid, m.p. 144°–145° C.

Example 5

The potassium salt of S-(+)-2-hydroxy-2-phenylpropionic acid (1.19 g, 5.64 mmol) was dissolved in isopropanol (50 mL) with heating and a solution of 12,12-diethoxy-13,13-dimethyl-6,11-ethano-6,11-dihydrobenzo[b]-quinolizinium chloride (1.8 g, 5 mmol) in isopropanol (20 mL) was added over three minutes. The mixture was stirred at room temperature for 2 hours, the inorganic salts were removed by filtration and the filtrate was concentrated in vacuo. The residue was dissolved in $CH_2Cl_2$ (100 mL), washed with water and the organic layer was concentrated in vacuo. The residue was recrystallized from isopropyl acetate, then isopropyl acetate/ isopropanol to afford 1.46 g (60 %) of 12,12-diethoxy-13,13-dimethyl-6,11-ethano-6,11-dihydrobenzo[b]quinolizinium (S)-(+)-$CH_3C(Ph)(OH)$-$CO_2^-$ [Formula I: $R^1=R^2=R^7=H$; $R^3=R^4=CH_3$; $R^5=R^6=OC_2H_5$; and $X^-=(S)$-(+)-$CH_3C(Ph)(OH)$-$CO_2^-$] as a white solid, m.p. 115°–116 ° C.

Example 6

(a)

(+)-Dibenzoyl-D-tartaric acid [(+)-DBT] (143 g, 0.399 mol) was dissolved in methanol (500 mL) and an aqueous solution of $KHCO_3$ (40.04 g, 0.40 mol) in water (150 mL) was slowly added. When the addition was complete, additional methanol (275 mL) and water (300 mL) were added and the mixture was stirred for 4 hours. A white precipitate formed, which was collected by filtration and washed with methanol (3×50 mL) to afford 130 g (82%) of the monopotassium salt of (+)-dibenzoyl-D-tartaric acid.

(b)

A mixture of the monopotassium salt of (+)-dibenzoyl-D-tartaric acid (33.63 g, 0.086 mol) and methanol (300 mL) was heated to reflux and water (300 mL) was slowly added. The hot solution was then added to a solution of 12,12-diethoxy-13,13-dimethyl-6,11-ethano-6,11-dihydrobenzo[b]quinolizinium chloride (30.03 g, 0.0835 mol) in methanol (500 mL). The reaction mixture was stirred at room temperature for 16 hours and any solids which formed were removed by filtration. The filtrate was extracted with $CH_2Cl_2$ (1×1000 mL, and 2×500 mL), and the organic layers were combined and concentrated in vacuo. The residue was azeotroped (2×) with methanol to remove any residual water, the solvent was removed in vacuo, and the residue was dissolved in $CH_2Cl_2$ (200 mL) and filtered. The filtrate was concentrated in vacuo, the residue was redissolved in methanol (300 mL) and reconcentrated to afford 51.1 g (90%) of 12,12-diethoxy-13,13-dimethyl-6,11-ethano-6,11-dihydrobenzo[b]quinolizinium−(+)-DBT] [Formula I: $R^1=R^2=R^7=H$; $R^3=R^4=CH_3$; $R^5=R^6=OC_2H_5$; and $X^-=-[(+)$-DBT]; as a 1:1 mixture of diastereomers] as an off-white solid, $[\alpha]D^{25}=+58.8°$, 1% MeOH.

(c)

12,12-Diethoxy-13,13-dimethyl-6,11-ethano-6,11-dihydrobenzo[b]-quinolizinium-[(+)-DBT] (49.24 g, 0.072 mol) was dissolved in acetonitrile (500 mL) with heating and then the solution was allowed to cool slightly. t-Butyl methyl ether (725 mL) was then added and the mixture was warmed for 4 minutes, and then allowed to cool to room temperature. The reaction mixture was stirred for 6.5 hours and the product which precipitated was collected by filtration, washed with tert-butyl methyl ether (2×500 mL) and dried at 45° C. under vacuum to afford 31.2 g (63%) of 12,12-diethoxy-13,13-dimethyl-6,11-ethano-6,11-dihydrobenzo[b]quinolizinium -[(+)-DBT] [Formula I: $R^1=R^2=R^7=H$; $R^3=R^4=CH_3$; $R^5=R^6=OC_2H_5$; and $X^-=-[(+)$-DBT], as approximately a 2:1 mixture of diastereomers, $[\alpha]D^{25}=+53.6°$, 1% MeOH. An additional 52.6 g of product was obtained from three other similar experimental runs, for a total of 83.8 g.

(d)

To a 2:1 mixture of the diastereomers of Example 6C (83.8 g, 0. 123 mol) was added 1,2-dichloroethane (500 mL) and the mixture was heated to reflux until all of the material had dissolved. The solution was filtered through Solka Floc ® and the filtrate was warmed on a steam bath for 5 minutes, and then gradually cooled to room temperature. The solution was seeded and crystals were allowed to form for 6 hours. The crystals were then collected by filtration, washed with cold dichloroethane (2×40 mL) and dried at 45° C. under reduced pressure to afford 37.4 g (45%) of 12,12-diethoxy-13,13-dimethyl-6,11-ethano-6,11-dihydrobenzo [b]quinolizinium −[(+)-DBT] [Formula I: $R^1=R^2=R^7=H$; $R^3=R^4=CH_3$; $R^5=R^6=OC_2H_5$; and $X^-=-[(+)$-DBT]; as a single diastereomer (>99.8% pure by HPLC)], $[\alpha]D^{25}=+32.9°$ C., 1% MeOH.

(e)

A solution of the single diastereomer of Example 6 (D) (10.02 g, 0.0147 mol) in warm methanol (50 mL) was added rapidly to a stirred aqueous solution of sodium perchlorate (11.94 g, 0.0976 mol), $NaHCO_3$ (3.55 g, 0.0423 mol) and water (1 L). The reaction mixture was stirred at room temperature for 16 hours and the white solid which precipitated was isolated by filtration and washed with water (20 mL). The solid was dried at 45° C. under reduced pressure to afford 5.21 g (84%) of (−)-12,12-diethoxy-13,13-dimethyl-6,11-ethano-6,11-dihydrobenzo[b]quinolizinium perchlorate; [Formula I: $R^1=R^2=R^7=H$; $R^3=R^4=CH_3$; $R^5=R^6=OC_2H_5$; and $X^-=ClO_4^-$, (−)-isomer], $[\alpha]D^{25}=-46.0°$, 1% methanol.

(f)

Following a procedure substantially similar to that described in Example 2, but dissolving the perchlorate in methanol rather than ethyl acetate, there was obtained 19.2 g of crude (−)-12,12-diethoxy-13,13-dimethyl-6,11-ethano-6,11-dihydrobenzo[b]quinolizinium chloride, [Formula I: $R^1=R^2=R^7=H$; $R^3=R^4=CH_3$; $R^5=R^6=OC_2H_5$; and $X^-=Cl^-$, (−)-isomer] from (−)-12,12-diethoxy-13,13-dimethyl-6,11-ethano-6,11-dihydrobenzo[b]quinolizinium perchlorate (21.6 g, 0.051 mol) and Dowex® ion-exchange resin (1650 g). The product was purified by column chromatography on silica eluting with 10% methanol/$CH_2Cl_2$ to afford 11.38 g (59%) of the (−)-isomer (100% enantiomerically pure by HPLC), $[\alpha]_D^{25}=-47.3°$, 1% methanol.

Example 7

(a)

The monopotassium salt of (−)-dibenzoyl-L-tartaric acid (99.1 g, 0.25 mol, prepared from (−)-dibenzoyl-L-tartaric acid [(−)-DBT] by a procedure substantially similar to that described in Example 6(a)) was dissolved in isopropanol (4.8 L) and water (2.4 L) with heating on a steam bath. A solution of 12,12-diethoxy-13,13-dimethyl-6,11-ethano-6,11-dihydrobenzo[b]quinolizinium chloride (60.0 g, 0.167 reel) in isopropanol (600 mL) was then added and the reaction mixture was cooled to room temperature and stirred for 16 hours. The reaction was warmed on a steam bath, and then the solvent was removed in vacuo. Dichloromethane (6L) was added to the residue and 16 hours later the solution was filtered to remove any inorganic salts. The filtrate was washed with water (3L), dried over $MgSO_4$ and concentrated in vacuo to afford 105.9 g (93.2%) of 12,12-diethoxy-13,13-dimethyl-6,11-ethano-6,11-dihydrobenzo[b]quinolizinium--[(−)-DBT] [Formula I: $R^1=R^2=R^7=H$; $R^3=R^4=CH_3$; $R^5=R^6=OC_2H_5$; and $X^-=-[(−)-DBT]$], as a 1:1 mixture of diastereomers.

(b)

12,12-Diethoxy-13,13-dimethyl-6,11-ethano-6,11-dihydrobenzo[b]-quinolizinium--[(−)-DBT] (105.9 g) was dissolved in 1,2-dichloroethane (1060 mL) with gentle heating on a steam bath. The mixture was cooled to room temperature and allowed to stand for 40 hours. A white solid precipitated from the solution which was collected by filtration and washed with 1,2-dichloroethane (2×25 mL) to afford 29.62 g (28%) of 12,12-diethoxy-13,13-dimethyl-6,11-ethano-6,11-dihydrobenzo[b]quinolizinium--[(−)-DBT] Formula I: $R^1=R^2=R^7=H$; $R^3=R^4=CH_3$; $R^5=R^6=OC_2H_5$; and $X^-=-$ [(−)-DBT]], as a single diastereomer, $[\alpha]_D^{25}=32.5$, 1% methanol. The product was isolated as a white solid and had a m.p.=124°-125° C.

(c)

A column of Dowex® 1×2-200 ion-exchange resin was eluted with 0.5N HCl until the eluant was clear and then was washed with distilled water until a pH of about 4.2 was obtained. 12,12-diethoxy-13,13-dimethyl-6,11-ethano-6,11-dihydrobenzo[b]quinolizinium--[(−)-DBT] (34.18 g, 50.1 mmol) in methanol (75 mL) was loaded onto the column and eluted with methanol (20 mL), water/methanol (1:1, 20 mL) and then water. The product fractions were pooled, neutralized with sat. $KHCO_3$ (6 mL) and the solvent was removed in vacuo.

Dichloromethane (1.5 L) was added to the residue and the pH of the solution was adjusted to 7 by the addition of 6N HCL (17 drops). The solution was dried over $MgSO_4$, and the solvent was removed in vacuo to afford 18.2 g of crude product. A similar experimental run on a 2.21 g (3.24 mmol) scale produced an additional 1.17 g of crude product for a total of 18.2 g. The combined product fractions were dissolved in methanol (40 mL) and passed through a second column of Dowex® 1×2-200 ion-exchange resin as described hereinabove to afford 19 g of crude product. The crude product was purified by column 5 chromatography eluting with 10% methanol/$CH_2Cl_2$ to afford 12.41 g of (+)-12,12-diethoxy-13,13-dimethyl-6,11-ethano-6,11-dihydrobenzo[b]quinolizinium chloride·½ hydrate [Formula I: $R^1=R^2=R^7=H$; $R^3=R^4=CH_3$; $R^5=R^6=OC_2H_5$; and $X^-=Cl^-$; as (+)-isomer], $[\alpha]_D^{25}=51.5$, 1% methanol, m.p.=100°-110° C. when dried in high vacuum for 5 days.

Example 8

A mixture of benzo[b]quinolizinium bromide (1.8 g, 6.9 mmol), tetraethoxyethylene (15 mL, 69 mmol) and acetonitrile (25 mL) was stirred at room temperature for 16 hours. The mixture was concentrated down to a small volume and diluted with ether and water. The aqueous layer was separated and treated with an aqueous solution of sodium perchlorate. A precipitate formed, which was collected by filtration and dried at 60° C. and 0.1 mm Hg for 20 hours to afford 2.6 g (97.7%) of 12,12,13,13,-tetraethoxy-6,11-ethane-6,11-dihydrobenzo[b]quinolizinium perchlorate [Formula I: $R^1=R^2=R^7=H$; $R^3=R^4=R^5=R^6=OC_2H_5$; and $X^-=ClO_4^-$] as an off-white solid, m.p. 202°-203° C.

Example 9

A mixture of benzo[b]quinolizinium perchlorate (0.09 g, 0.32 mmol), 2-isopropylidene-4R,5R-(dibenzyloxymethyl-1,3-dioxolane [Formula V: $R^3=R^4=CH_3$; $R^5$ and $R^6$ together=(R,R)-OCH(CH$_2$OCH$_2$Ph)CH(CH$_2$OCH$_2$Ph)—O—] 0.52 g, 1.46 mmol) and acetonitrile (10 mL) was stirred at room temperature under $N_2$ for 1 hour. The solvent was removed in vacuo and the residue was purified by column chromatography on silica gel eluting with ether (100%) to 10% methanol/$CH_2Cl_2$ to afford 0.16 g (78%) of 12,12-(1R,2R-dibenzyloxymethyl-ethanediol ketal)-13,13-dimethyl-6,11-ethano-6,11-dihydrobenzo[b]quinolizinium perchlorate [Formula I: $R^1=R^2=R^7=H$; $R^3=R^4=CH_3$; $R^5=R^6$ together=(R,R)—O—CH(CH$_2$OCH$_2$Ph)CH(CH$_2$OCH$_2$Ph)—O—; and $X^-=ClO_4^-$], as a white solid.

Example 10 a, b and c

A mixture of benzo[b]quinolizinium perchlorate (0.88 g, 3.15 mmol), 2-isopropylidene-4R,6R-dimethyl-1,3-dioxane [Formula V: $R^3=R^4=CH_3$; $R^5$ and $R^6$ together=(R,R)—O—CH(CH$_3$)CH$_2$CH(CH$_3$)—O—] (0.7 g, 4.48 mmol) and acetonitrile (10 mL) was stirred at room temperature under $N_2$ for 30 minutes. The solvent was removed in vacuo, the residue was triturated with ether, and the product was collected by filtration to afford 1.05 g (78%) of 12,12-(2R,4R-pentanediol ketal)-13,13-dimethyl-6,11-ethano-6,11-dihydrobenzo[b]quinolizinium perchlorate. [Formula I: $R^1=R^2=R^7=H$; $R^3=R^4=CH_3$; $R^5$ and $R^6$ together=(R,R)—O—CH(CH$_3$)CH$_2$CH(CH$_3$)—O—; and X$^-$=ClO$_4$$^-$] as a mixture of diastereomers (Example 10 (a)). The 1.05 g from the present experimental run was combined with 11.95 g of product obtained from two similar experimental runs, and the combined total of 13.0 g was separated into its constituent diastereomers by high performance liquid chromatography using two delta-pak C-18 columns and eluting with 0.05N ammonium acetate/methanol. The appropriate chromatography fractions were pooled, concentrated in vacuo, taken up in water and treated with 10% aqueous sodium perchlorate. A solid formed, which was collected by filtration and washed successively with water, hexane and then ether to afford 1.9 g of 12,12-(2R,4R-pentanediol ketal),13,13-dimethyl-6,11-ethano-6,11-dihydrobenzo[b]quinolizinium perchlorate [Formula I: R$^1$=R$^2$=R$^7$=H; R$^3$=R$^4$=CH$_3$; R$^5$ and R$^6$together=(R,R)—O—CH(CH$_3$)CH$_2$CH—(CH$_3$)—O—; and X$^-$=ClO$_4$$^-$], as one diastereomer, hereinbelow referred to as Example 10 (b); and 0.7 g of 12,12-(2R,4R-pentanediol ketal)-13,13-dimethyl-6,11-ethano-6,11-dihydrobenzo[b]quinolizinium perchlorate [Formula I: R$^1$=R$^2$=R$^7$=H; R$^3$=R$^4$=CH$_3$; R$^5$ and R$^6$ together=(R,R)—O—CH(CH$_3$)CH$_2$CH(CH$_3$)—O—; and X$^-$=ClO$_4$$^-$], as the other diastereomer, hereinbelow referred to as Example 10(c). A 0.1 g fraction of the diastereomer of Example 10(b) was recrystallized from ethanol to afford 0.064 g of purified product, as a white solid, m.p.=191°-192° C., [α]D$^{25}$+3.5 (C=0.25, CHCl$_3$). A 0.06 g fraction of the diastereomer of Example 10(c) was recrystallized from ethanol to afford 0.028 g of purified product as a white solid, m.p.=192°-193° C., [α]D$^{25}$−78° (C=0.25, CHCl$_3$).

Example 11

A solution of 12,12-(2R,4R-pentanediol ketal)-13,13-dimethyl-6,11-ethano-6,11-dihydrobenzo[b]quinolizinum perchlorate of Example 10 (a) (2.0 g, 4.59 mmol) in acetonitrile (20 mL) was loaded onto a Dowex® 1×2-200 ion-exchange resin column (100 g, purified as described hereinabove in Example 2) and eluted with water. The pooled product fractions were concentrated in vacuo and dried in high vacuum for 16 hours to afford 1.2 g (70.6%) of 12,12-(2R,4R-pentanediol ketal)-13,13-dimethyl-6,11-ethano-6,11-dihydrobenzo[b]-quinolizinium chloride-½ hydrate [Formula I: R$^1$=R$^2$=R$^7$=H; R$^3$=R$^4$=CH$_3$; R$^5$ and R$^6$ together=(R,R)—O—CH(CH$_3$)CH$_2$CH (CH$_3$)—O—; and X$^-$=Cl$^-$]as a mixture of diastereomers.

Example 12

(a)

A mixture of 12,12-(2R,4R-pentanediol ketal)-13,13-dimethyl-6,11-ethano-6,11-dihydrobenzo[b]quinolizinium perchlorate of Example 10 (c) (0.46 g, 1.05 mmol) in concentrated hydrochloric acid (10 mL) was heated at 80° C. for 1.5 hours. The mixture was cooled to room temperature, diluted with water and treated with 10% sodium perchlorate in water. The mixture was cooled and the solid which formed was collected by filtration and washed with water, hexane, then ether. The compound was dried to afford 0.33 g (89%) of (−)12-oxo-13,13-dimethyl-6,11-ethano-6,11-dihydrobenzo[b]quinolinium perchlorate [Formula I: R$^1$=R$^2$=R$^7$=H; R$^3$=R$^4$=CH$_3$; R$^5$ and R$^6$ together=O; and X$^-$=ClO$_4$$^-$, as (−)-isomer] as white crystals, m.p.=282°-284° C. (dec.), [α]D$^{25}$=−1.36°, 1% methanol.

(b)

To a solution of (−)-12-oxo-13,13-dimethyl-6,11-ethano-6,11-dihydrobenzo[b]quinolizinium perchlorate of Example 12 (a) (0.3 g, 0.86 mmol) in tetraethoxysilane (1.65 g, 8.6 mmol), nitromethane (4 mL) and ethanol (0.5 mL, 8.6 mmol) was added chloroform (about 95 mL). The reaction mixture was heated to reflux and most of the chloroform was removed via a Dean-Stark apparatus. The reaction mixture was cooled to room temperature, and triflic acid (0.13 g, 0.07 mL, 0.86 mmol) was added. The 0 reaction mixture was then placed in a 10 mL plastic syringe, which was placed in a high pressure apparatus at 10 kbar for 24 hours. The reaction mixture was poured into CH$_2$Cl$_2$ (20 mL) containing pyridine (1.0 mL) at 0° C. The reaction mixture was evaporated in vacuo and the residue was triturated with hexane and the hexane was decanted to afford 0.8 g of crude (−)-12,12-diethoxy-13,13-dimethyl-6,11-ethano-6,11dihydrobenzo[b]quinolizinium perchlorate [Formula I: R$^1$=R$^2$=R$^7$=H; R$^3$=R$^4$=CH$_3$; R$^5$=R$^6$=OC$_2$H$_5$; and X$^-$=ClO$_4$$^-$; as (−)-isomer].

(c)

The crude (−)-isomer of Example 12(b) was dissolved in methanol/ethylacetate (2 mL, 1/1) and loaded onto a Dowex® 1×2-200 ion-exchange resin column, which was purified as described in Example 2, and eluted with water. The product fractions were pooled, concentrated in vacuo, and the residue was purified by column chromatography on silica eluting with CH$_2$Cl$_2$/methanol (9/1) to afford 0.22 g (71%) of (−)-12,12-diethoxy-13,13-dimethyl-6,11-ethano-6,11-dihydrobenzo[b]quinolizinium chloride. ½-7/4 hydrate [Formula I: R$^1$=R$^2$=R$^7$=H; R$^3$=R$^4$=CH$_3$; R$^5$=R$^6$=OC$_2$H$_5$; and X$^-$=Cl$^-$; as (−)isomer]. The product was recrystallized from CH$_2$Cl$_2$/ether/hexane to afford 0.17 g (55%) of the product as a white powder, [α]D$^{25}$=−42.3°, 1% CHCl$_3$.

Example 13

(a)

Following a procedure substantially similar to that described in Example 12, part a, there was obtained 0.52 g (93%) of (+)-12-oxo-13,13-dimethyl-6,11-ethano-6,11-dihydrobenzo[b]quinolizinium perchlorate [Formula I: R$^1$=R$^2$=R$^7$=H; R$^3$=R$^4$=CH$_3$; R$^5$ and R$^6$ together=O; and X$^-$=ClO$_4$$^-$, as (+)-isomer], m.p.=281°-283° C., [α]D$^{25}$=+1.1, 1% CH$_3$CN; from 12,12-(2R,4R-pentanediol ketal)-13,13-dimethyl-6,11-ethano-6,11-dihydrobenzo[b]quinolizinium perchlorate of Example 10(b) (0.7 g, 1.6 mmol) and concentrated hydrochloric acid (15 mL).

(b)

Following a procedure substantially similar to that described in Example 12(b), there was obtained 0.51 g of crude (+)-12,12-diethoxy-13,13-dimethyl-6,11-ethano-6,11-dihydrobenzo[b]quinolizinium perchlorate [Formula I: R$^1$=R$^2$=R$^7$=H; R$^3$=R$^4$=CH$_3$; R$^5$=R$^6$=OC$_2$H$_5$; and X$^-$=ClO$_4$$^-$, as (+)-isomer], from (+)-12-oxo-13,13-dimethyl-6,11-ethano-6,11-dihydrobenzo[b]-quinolizinium perchlorate (0.349 g, 1 mmol), tetraethoxysilane (2.1 mL, 10 mmol), ethanol (0.6 mL, 10 mmol), nitromethane (4 mL) and triflic acid (0.1 mL, 1 mmol).

(c)

Following a procedure substantially similar to that described in Example 12(c), there was obtained 0.23 g of 12,12-diethoxy-13,13-dimethyl-6,11-ethano-6,11-dihydrobenzo[b]quinolizinium chloride-½-¾ hydrate [Formula I: $R^1=R^2=R^7=H$; $R^3=R^4=CH_3$; $R^5=R^6=OC_2H_5$; and $X^-=Cl^-$; as (+)-isomer], m.p.=120°-121° C., $[\alpha]589^{25}=+43.8°$, 1% $CHCl_3$; from (+)-12,12-diethoxy-13,13-dimethyl-6,11-ethano-6,11-dihydrobenzo[b]quinolizinium perchlorate (0.71 g), and Dowex® 1×2-200 ion-exchange resin, after purification of the product by column chromatography on silica eluting with $CH_2Cl_2$/ether (4:1) to $CH_2Cl_2$/ether/methanol (8/1/1) and recrystallization from $CH_2Cl_2$/ether/hexane.

Example 15

(a)

A mixture of 10-acetoxybenzo[b]quinolizinium perchlorate (1.9 g, 5.6 mmol), 1,1-diethoxy-2,2-dimethylethylene (2.8 g, 11.6 mmol of 60% pure material) in acetonitrile (35 mL) was heated at 60 ° C. under argon for 8 hours and then was stirred at room temperature for 16 hours. The solvent was removed in vacuo, the residue was treated with ether and the mixture was sonicated. A solid formed, which was collected by filtration, washed successively with water, hexanes, then ether and dried to afford 2.6 g of crude product. The crude product was recrystallized from isopropanol and dried at 40° C. under high vacuum to afford 1.9 g (70%) of 10-acetoxy-12,12-diethoxy-13,13-dimethyl-6,11-ethano-6,11-dihydrobenzo[b]quinolizinium perchlorate [Formula I: $R^1=R^7=H$; $R^2=10—OAc$; $R^3=R^4=CH_3$; $R^5=R^6=OC_2H_5$; and $X^-=ClO_4^-$] as an off-white powder; m.p. 135°-137° C.

(b)

To a solution of 10-acetoxy-12,12-diethoxy-13,13-dimethyl-6,11-ethano-6,11-dihydrobenzo[b]quinolizinium perchlorate (0.5 g, 1 mmol) in methanol (25 mL) at room temperature, was added NaOH (0.12 g, 3 equivalents). The solution was stirred for 15 minutes, acetic acid in methanol (2.25 mL, 1.5M solution) was added and the mixture was stirred for 5 minutes. The solvent was removed in vacuo and a 10% solution of sodium perchlorate in water (15 mL) was added. The mixture was extracted with $CH_2Cl_2$ (2×50 mL), the organic phases were combined, dried and concentrated in vacuo. The solid residue was recrystallized from water to afford 0.24 g (52%) of 10-hydroxy-12,12-diethoxy-13,13-dimethyl-6,11-ethano-6,11-dihydrobenzo[b]quinolizinium perchlorate [Formula I: $R^1=R^7=H$; $R^2=10—OH$; $R^3=R^4=CH_3$; $R^5=R^6=OC_2H_5$; $X^-=ClO_4^-$] as a white solid.

(c)

A Dowex® 1×2-200 ion-exchange resin column (100 g of resin) was eluted with 0.5N HCl (1.5 L) until a clear solution was obtained and then was washed with water (4 L) until a pH of about 6.0 was obtained. A solution of 10-hydroxy-12,12-diethoxy-13,13-dimethyl-6,11-ethano-6,11-dihydrobenz[b]-quinolizinium perchlorate (1.4 g, 3.2 mmol) in acetonitrile was then loaded onto the resin column and eluted with water. The product fractions were pooled, and concentrated in vacuo to afford 0.85 g (70.8%) of 10-hydroxy-12,12-diethoxy-13,13-dimethyl-6,11-ethano-6,11-dihydrobenzo[b]quinolizinium chloride [Formula I: $R^1=R^7=H$; $R^2$-10=OH; $R^3=R^4=CH_3$; $R^5=R^6=OC_2H_5$; and $X^-=Cl^-$], as a white solid, m.p. 151° C. (dec.).

Example 16

A mixture of 7-methoxybenzo[b]quinolizinium hexafluorophosphate (0.66 g, 1.85 mmol), 1,1-diethoxy-2,2-dimethylethylene (2.05 g, 60% pure material) in acetonitrile (25 mL) was heated to 75° C. under argon for 12 hours. The solvent was removed in vacuo and the residue was purified by column chromatography on silica eluting with dichloromethane/methanol (9/1) to afford a foamy solid. The solid was taken up in water and sonicated, and the solids thus obtained were collected by filtration and air dried to afford 0.36 g (39%) of 7-methoxy-12,12-diethoxy-13,13-dimethyl-6,11-ethano-6,11-dihydrobenzo[b]quinolizinium hexafluorophosphate [Formula I: $R^1=R^7=H$; $R^2=7—OCH_3$; $R^3=R^4=CH_3$; $R^5=R^6=OC_2H_5$; $R^7=H$; and $X^-=PF_6^-$] as a brown solid.

Example 17

(a)

A mixture of benzo[b]quinolizinium perchlorate (3.8 g, 13.6 mmol), a compound of Formula V ($R^3=OCH_3$; $R^4=OSi(CH_3)_3$; $R^5=R^6=C_2H_5$) (6.3 g, 0.031 mol) and acetonitrile (100 mL) was stirred at room temperature under $N_2$ for 18 hours. The solvent was removed in vacuo, the residue was taken up in ether and the solids thus obtained were collected by filtration to afford 6.3 g (97%) of 12-methoxy-12-trimethylsilyloxy-13,13-diethyl-6,11-ethano-6,11-dihydrobenzo[b]quinolizinium perchlorate [Formula I: $R^1=R^2=R^7=H$; $R^3=R^4=Et$; $R^5=OCH_3$; $R^6=OSi(CH_3)_3$; and $X^-=ClO_4^-$].

(b)

A mixture of 12-methoxy-12-trimethylsilyloxy-13,13-diethyl-6,11-ethano-6,11-dihydrobenzo[b]quinolizinium perchlorate (4.8 g, 0.01 mol) and concentrated HCl (80 mL) was heated at 80° C. under $N_2$ for 1 hour. The mixture was cooled to room temperature, diluted with water (300 mL) and treated with a 10% aqueous solution of sodium perchlorate (200 mL). The mixture was cooled and the solid which precipitated was collected by filtration, and washed successively with water, ether and then hexanes to afford 3.72 g (99%) of 12-oxo-13,13-diethyl-6,11-ethano-6,11-dihydrobenzo[b]quinolizinium perchlorate [Formula I: $R^1=R^2=R^7=H$; $R^3=R^4=$-Et; $R^5$ and $R^6$ together==O; and $X^-=ClO_4^-$].

(c)

To a solution of 12-oxo-13,13-diethyl-6,11-ethano-6,11-dihydrobenzo[b]quinolizinium perchlorate (1.0 g, 2.6 mmol) in nitromethane (8 mL), tetraethoxysilane (5.52 g, 26.5 mmol) and ethanol (1.2 g, 26.5 mmol) was added chloroform (150 mL). The reaction mixture was refluxed and most of the chloroform was removed by a Dean-Stark apparatus. The react ion mixture was cooled to room temperature and triflic acid (0.39 g, 2.6 mmol) was added. The reaction mixture was taken up into a 20 mL plastic syringe and placed in a high pressure apparatus at 150,000 psi for 2½ days. The reaction mixture was poured into ice-water containing saturated $NaHCO_3$, extracted with $CH_2Cl_2$ (2×100 mL) and the combined organic layers were dried over Na$_2$SO$_4$ and concentrated in vacuo. The residue was taken up in hexane (50 mL), sonicated and a solid was collected by filtration and washed with hexane. The solid was taken up in ethyl acetate (10 mL), treated with CH$_2$Cl$_2$ (0.5 mL) and allowed to stand. A solid formed which was collected by filtration and washed with ethyl acetate to afford 0.5 g of recovered starting material. The filtrate was placed on a silica gel column and eluted with ethyl acetate/PAW (6/4; wherein PAW=pyridine/acetic acid/water (55/25/20) to afford 0.21 g (17.5%) of crude 12,12-diethoxy-13,13-diethyl-6,11-ethano-6,11-dihydrobenzo[b]quinolizinium perchlorate [Formula I: R$^1$=R$^2$=R$^7$=H; R$^3$=R$^4$=Et; R$^5$=R$^6$=OC$_2$H$_5$; and X$^-$=ClO$_4^-$]. The crude product was passed through a Dowex® 1×2-200 ion-exchange resin (30 g, resin was purified as described hereinabove in Example 15C) eluting with water and the pooled product fractions were concentrated in vacuo. The residue was taken up in water (5 mL) and treated with an aqueous solution of 10% sodium perchlorate and the solid which precipitated was collected by filtration, and washed with water and air dried to afford 0.11 g of purified product as the perchlorate, isolated as a white solid, m.p. 121° C. (dec).

Example 18

A mixture of benzo[b]quinolizinium perchlorate (2.55 g, 1.96 mmol), 1,1-diethoxy-2,2-dimethylethylene (2.0 g of 15% solution in THF/t-BuOH) and acetonitrile was heated at 50° C. for 6 hours. The mixture was cooled to room temperature, the solvent was removed in vacuo, and the residue was taken up in CHCl$_3$ and filtered. The solvent was removed in vacuo and the residue was purified by column chromatography on silica eluting with CH$_2$Cl$_2$/ethyl acetate/methanol (5/4/1) to afford 0.12 g (15.6%) of 12,..12-(1; 2-ethanediol ketal)-13,13-dimethyl-6,11-ethano-6,11-dihydrobenzo[b-]quinolizinium perchlorate [Formula I: R$^1$=R$^2$=R$^7$=H; R$^3$=R$^4$=CH$_3$; R$^5$ and R$^6$ together are —O(CH$_2$)$_2$O—; and X$^-$=ClO$_4^-$] as a white solid, m.p. 240°-242° C. (dec.).

Example 19

(a)

A mixture of 10-methoxybenzo[b]quinolizinium perchlorate (8.0 g, 25.8 mmol), 1,1-diethoxy-2,2-dimethylethylene (12.5 g, 5 60% pure material) and acetonitrile (75 mL) were heated at 60° C. under argon for 16 hours. The reaction mixture was cooled and the solvent was removed in vacuo. The residue was taken up in a 10% aqueous solution of sodium perchlorate (200 mL) and the mixture was extracted with CH$_2$Cl$_2$ (2×250 mL). The combined organics were dried over Na$_2$SO$_4$ and concentrated in vacuo. The residue was purified by column chromatography on silica eluting with methanol/CH$_2$Cl$_2$ (5/95) to afford a gummy residue. The residue was taken up in isopropanol (200 mL), treated with charcoal (5.0 g), boiled and filtered. The filtrate was concentrated in vacuo to afford 5.0 g (43.9%) of crude 10-methoxy-12,12-diethoxy-13,13-dimethyl-6,11-ethano-6,11-dihydrobenzo[b]quinolizinium perchlorate [Formula I: R$^1$=H; R$^2$=10—OCH$_3$; R$^7$=H; R$^3$=R$^4$=CH$_3$; R$^5$=R$^6$=OC$_2$H$_5$; and X$^-$=ClO$_4^-$], as a yellow foam.

(b)

Alternatively, the above reaction was also performed as described hereinbelow. To acetonitrile (5.0 mL) was added 10-methoxybenzo[b]quinolizinium perchlorate (0.08 g, 0.2 mmol), followed by 1,1-diethoxy-2,2-dimethylethylene (0.081 g, 0.38 mmol, 68% pure material with impurity being ethyl isobutyrate). The mixture was stirred at room temperature for 1 hour, then was heated to 60° C. for 10 hours. The solvent was removed in vacuo, toluene was added to the residue and the solvent was removed in vacuo. The residue was taken up in water/methanol (4/1) and sodium perchlorate (0.5 g) was added. The methanol was removed in vacuo and the mixture was filtered to afford 0.021 g (23%) of 10-methoxy-12,12-diethoxy-13-13-dimethyl-6,11-ethano-6,11-dihydrobenzo[b]quinolizinium perchlorate, as an orange-brown solid, m.p. 85°-95° C.

(c)

10-Methoxy-12,12-diethoxy-13,13-dimethyl-6,11-ethano-6,11-dihydrobenzo[b]quinolizinium perchlorate of Example 19 (a) (5.0 g, 11.2 mmol) was dissolved in methanol/ethyl acetate (1:1, 20 mL) and loaded onto a Dowex® 1×2-200 ion-exchange resin column (150 g, resin was purified in a manner similar to that described hereinabove in Example 15C until a pH of about 5 was obtained for water eluant). The column was eluted with water, and the product fractions were pooled, and concentrated in vacuo. The residue was dissolved in warm water (200 mL) and potassium hexafluorophosphate (2.3 g) in hot water (100 mL) was added. The mixture was stirred for 10 minutes and the precipitate which formed was collected by filtration and washed with warm water to afford 5.5 g (98%) of 10-methoxy-12,12-diethoxy-13,13-dimethyl-6,11-ethano-6,11-dihydrobenzo[b]quinolizinium hexafluorophosphate [Formula I: R$^1$=H; R$^2$=10—OCH$_3$; R$^7$=H; R$^3$=R$^4$=CH$_3$; R$^5$=R$^6$=OC$_2$H$_5$; and X$^-$=PF$_6^-$], as a pale yellow solid.

(d)

Following a procedure similar to that described in Example 15C, but loading the compound in methanol/CH$_3$CN (9/1) rather than acetonitrile, there was obtained 2 7g (64%) of 10-methoxy-12,12-diethoxy-13,13-dimethyl-6,11-ethano-6,11-dihydrobenzo[b-]quinolizinium chloride·3/2 hydrate. [Formula I: R$^1$=H; R$^2$=10—OCH$_3$; R$^7$=H; R$^3$=R$^4$=CH$_3$; R$^5$=R$^6$=OC$_2$H$_5$; and X$^-$=Cl$^-$], as a yellow solid; from the hexafluorophosphate of Example 19 (C) (5.1g) and Dowex® 1×2-200 ion-exchange resin (150 g).

Example 20

(a)

To a mixture of 9-methoxybenzo[b]quinolizinium perchlorate/hexafluorophosphate (1.33 g, 0.004 mol, 4.8/1 ratio of perchlorate to hexafluorophosphate) and acetonitrile was added 1,1-diethoxy-2,2-dimethylethylene (1.17 g, 0.081 mol). The mixture was heated to 60° C. for 12 hours, additional 1,1-diethoxy-2,2-dimethylethylene was added (1.0 g), and the mixture was heated at reflux for 18 hours. The mixture was cooled, the solvent was removed in vacuo and the residue was taken up in 8% ethanol/0.5% triethylamine/CH$_2$Cl$_2$. The mixture was filtered and the filtrate was purified by column chromatography on silica eluting with 8% ethanol/0.5% triethylamine/CH$_2$Cl$_2$. The product fractions were pooled, concentrated in vacuo, and the residue was taken up in methanol (0.5 mL) and added to a hot solution (60° C.) of potassium hexafluorophosphate (1.47 g) in water (50 mL). The methanol was removed by filtration, the water was decanted, and the residue was taken up in methanol and treated with water. Removal of the methanol, and decantation of water afford 0.62 g (31.2%) of 9-methoxy-12,12-diethoxy-13,13-dimethyl-6,11-ethano-6,11-dihydrobenzo[b]quinolizinium hexafluorophosphate [Formula I: $R^1$=H; $R^2$=9—$OCH_3$; $R^7$=H; $R^3$=$R^4$=$CH_3$; $R^5$=$R^6$=$OC_2H_5$; and $X^-$=$PF_6^-$] as a tan powder, m.p. 76°–81° C., when dried at 40° C. in high vacuum.

(b)

Following a procedure substantially similar to that described above in Example 20 (a), but starting with 9-methoxybenzo[b]quinolizinium hexafluorophosphate, there was obtained directly 9-methoxy-12,12-diethoxy-13,13-dimethyl-6,11-ethano-6,11-dihydrobenzo[b]quinolizinium hexafluorophosphate; from 9-methoxybenzo[b]quinolizinium hexafluorophosphate (4.5 g, 0.013 mol), acetonitrile (50 mL), and 1,1-diethoxy-2,2-dimethylethylene (4.75 g, 0.033 mol).

(c)

Following a procedure substantially similar to that described in Example 15C, there was obtained 3.5 g of crude 9-methoxy-12,12-diethoxy-13,13-dimethyl-6,11-ethano-6,11-dihydrobenzo[b]quinolizinium chloride [Formula I: $R^1$=H; $R^2$=9—$OCH_3$; $R^7$=H; $R^3$=$R^4$=$CH_3$; $R^5$=$R^6$=$OC_2H_5$; and $X^-$=$Cl^-$], from 9-methoxy-12,12-diethoxy-13,13-dimethyl-6,11-ethano-6,11-dihydrobenzo[b]quinolizinium hexafluorophosphate of Example 20(b), Dowex® 1×2-200 ion-exchange resin (150 g) and acetonitrile (20 mL). The crude product was treated with an aqueous solution of sodium perchlorate and the resulting precipitate was collected by filtration and purified by column chromatography on silica eluting with acetonitrile/$CH_2Cl_2$ (⅓) to afford the product as the perchlorate anion. The perchlorate was loaded onto a Dowex® 1×2-200 ion-exchange column as described hereinabove, eluted with water and the product fractions were concentrated in vacuo to afford purified 9-methoxy-12,12-diethoxy-13,13-dimethyl-6,11-ethano-6,11-dihydrobenzo[b]quinolizinium chloride, as a tan solid.

Example 21

(a)

A reaction mixture of 2 g (6.8 mmol) of 11-methylbenzo[b]quinolizinium perchlorate and 3.2 g of 1,1-dimethyl-2,2-diethoxyethylene in 100 ml of acetonitrile was heated under nitrogen at 80° C. for 16 hours. Additional 2,2-dimethyl-1,1-diethoxyethylene (1.0 g) was added to the mixture and the reaction mixture was heated at 80° C. for one hour and cooled to room temperature. The reaction mixture was concentrated in vacuo, the residue was triturated with ether, and the solid was isolated by filtration and dried. The solid product was recrystallized from isopropanol (with activated charcoal) to afford 1.98 g (66%) of 6,11-ethano-12,12-diethoxy-13,13-dimethyl-11-methyl-6,11-dihydrobenzo[b]quinolizinium perchlorate. (Formula I: $R^1$=$R^2$=H; $R^3$=$R^4$=$CH_3$; $R^5$=$R^6$=$OC_2H_5$; $R^7$=$CH_3$; $X^-$=$ClO_4^-$).

(b)

The above purified perchlorate was converted to the corresponding chloride salt by passing the perchlorate through 75 g of Dowex® 1×2-200 pretreated with 0.5N HCl to afford 0.52 g (51%) of 6,11-ethano-12,12-diethoxy-13,13-dimethyl-11-methyl-6,11-dihydrobenzo[b]quinolizinium chloride (Formula I: $R^1$=$R^2$=H; $R^3$=$R^4$=$CH_3$; $R^5$=$R^6$=$OC_2H_5$; $R^7$=$CH_3$; $X^-$=$Cl^-$).

Example 22

(a)

Following a procedure similar to that described in Example 21, a reaction mixture of 6.5 g (23.3 mmol) of benzo[b]quinolizinium perchlorate and 6.5 g (50.7 mmol) of 2-isopropylidene-1,3-dioxane in 100 ml of acetonitrile was stirred under nitrogen at room temperature for 2 hours. The mixture was concentrated in vacuo, the residue triturated with ether, and the solid product was filtered and dried to afford 9.2 g (97%) of 6,11-ethano-12,12-(1,3-propanediol ketal)-13,13-dimethyl-6,11-dihydrobenzo[b]quinolizinium perchlorate (Formula I: $R^1$=$R^2$=$R^7$=H; $R^3$=$R^4$=$CH_3$; $R^5$ and $R^6$ together=—O($CH_2$)$_3$O—; $X^-$=$ClO_4^-$).

(b)

The perchlorate of Example 22(a) (9.2 g) in a minimum amount of acetonitrile was converted to the corresponding chloride salt by passing the perchlorate through 280 g of Dowex® 1×2-200 eluting with water to afford 7.2 g (85.7%) of 6,11-ethano-12,12-(1,3-propanediol ketal)-13,13-dimethyl-6,11-dihydrobenzo[b]quinolizinium chloride (Formula I: $R^1$=$R^2$=$R^7$=H; $R^3$=$R^4$=$CH_3$; $R^5$ and $R^6$ together=—O($CH_2$)$_3$O—; $X^-$=$Cl^-$).

Example 23

(a)

Following a procedure similar to that described in Example 21, a reaction mixture of 1 g (2.5 mmol) of 9-trifluoromethyl benzo[b]quinolizinium hexafluorophosphate and 1.08 g (7.5 mmol) of 1,1-diethoxy-2,2-dimethylethylene in 10 ml of acetonitrile was refluxed under nitrogen for 10 days. The mixture was cooled, filtered through silica using 150 ml of acetonitrile, the filtrate was concentrated in vacuo, and the residue triturated with water and filtered to yield as a solid 6,11-ethano-12,12-diethoxy-13,13-dimethyl-9-trifluoromethyl-6,11-dihydrobenzo[b]quinolizinium hexafluorophosphate. (Formula I: $R^1$=$R^7$=H; $R^2$=9—$CF_3$; $R^3$=$R^4$=$CH_3$; $R^5$=$R^6$=$OC_2H_5$; $X^-$=$PF_6^-$).

(b)

The above hexafluorophosphate in 10 ml of acetonitrile was converted to the corresponding chloride salt by passing the hexafluorophosphate through 60 g of Dowex® 1×2-200 pretreated with 0.5N HCl and eluting with water. The eluent was treated with 1 g of activated charcoal, and filtered. The filtrate was extracted with ether (2×240 ml), and the aqueous layer was concentrated in vacuo to afford 0.48 g (48%) of 6,11-ethano-12,12-diethoxy-13,13-dimethyl-9-trifluoromethyl-6,11-dihydrobenzo[b]quinolizinium chloride (Formula I: $R^1$=$R^7$=H; $R^2$=9—$CF_3$; $R^3$=$R^4$=$CH_3$; $R^5$=$R^6$=$OC_2H_5$; $X^-$=$Cl^-$), as a foam.

Example 24

(a)

Following a procedure similar to that described in Example 21, a reaction mixture of 2 g (5.5 mmol) of 8,10-difluorobenzo[b]quinolizinium hexafluorophosphate and 2.4 g (7.5 mmol) of 1,1-diethoxy-2,2-dimethylethylene in 20 ml of acetonitrile was refluxed under nitrogen with stirring for 3 days. The mixture was cooled, filtered through silica using 150 ml of acetonitrile, the filtrate was concentrated in vacuo, and the residue triturated with water and filtered to yield a solid hexafluorophosphate as a glass. The salt was purified by chromatography on silica eluting with acetonitrile/methylene chloride (1:3).

(b)

The above hexafluorophosphate in a minimum amount of acetonitrile was converted to the corresponding chloride salt by passing the salt through Dowex® 1×2-200 pretreated with 0.5N HCl and eluting with water. The aqueous layer was concentrated in vacuo to afford 1.10 g (51%) of 6,11-ethano-12,12-diethoxy-13,13-dimethyl-8,10-difluoro-6,11-dihydrobenzo[b]quinolizinium chloride (Formula I: $R^1=R^7=H$; $R^2=8, 10—F_2$; $R^3=R^4=CH_3$; $R^5=R^6=OC_2H_5$; $X^-=Cl^-$).

Example 25

(a)

Following a procedure similar to that described in Example 21, a reaction mixture of 0.5 g (1.4 mmol) of 8-methoxybenzo[b]quinolizinium hexafluorophosphate and 0.43 g (3.0 mmol) of 1,1-diethoxy-2,2-dimethylethylene in 15 ml of acetonitrile was heated at 65° C. for 20 hours. Additional 1,1-diethoxy-2,2-dimethylethylene (0.43 g) was added, and the reaction mixture was heated 12 hours and then allowed to stand at room temperature for 14 days. The mixture was filtered through silica using 200 ml of acetonitrile, the filtrate was concentrated in vacuo, the residue was purified by flash chromatography eluting with methylene chloride/acetonitrile (9:1), and the product was isolated by concentrating the eluent in vacuo to yield as a solid 6,11-ethano-12,12-diethoxy-13,13 dimethyl-8-methoxy-6,11-dihydrobenzo[b]quinolizinium hexafluorophosphate (Formula I: $R^1=R^7=H$; $R^2=8—OCH_3$; $R^3=R^4=CH_3$; $R^5=R^6=OC_2H_5$; $X^-=PF_6^-$).

(b)

The above hexafluorophosphate in 3 ml of acetonitrile was converted to the corresponding chloride salt by passing the salt through Dowex® 1×2-200 pretreated with 0.5N HCl and eluting with water. The aqueous layer was concentrated in vacuo and dried to afford 237 mg (48.8 %) of 6,11-ethano-12,12-diethoxy-13,13-dimethyl-8-methoxy-6,11-dihydrobenzo[b]quinolizinium chloride (Formula I: $R^1=R^7=H$; $R^2=8—OCH_3$; $R^3=R^4=CH_3$; $R^5=R^6=OC_2H_5$; $X^-=Cl^-$), as an amorphous solid.

Example 26

Following a procedure similar to that described in Example 21, a reaction mixture of 2.87 g (9.7 mmol) of 9-chlorobenzo[b]quinolizinium chloride and 2.1 g (<14.6 mmol) of 1,1-diethoxy-2,2-dimethylethylene in 30 ml of acetonitrile was allowed to react at room temperature for 4 hours and then heated at 50° C. for 24 hours. An additional 2,2-diethoxy-1,1-dimethylethylene (1 g) was added and the reaction mixture was heated at 50° C. for 24 hours and then at 70° C. for 24 hours. The mixture was cooled, filtered through silica using 200 ml of acetonitrile, the filtrate was concentrated in vacuo, and the residue was purified by chromatography on silica eluting with 9% methanol in methylene chloride (0.5% TEA). The residue from the eluent was dissolved in water/methanol, treated with an aqueous sodium perchlorate solution, methanol was distilled in vacuo, and the mixture was cooled; and filtered.

The product isolated was dissolved in ethyl acetate, diluted with ether, cooled, filtered and isolated. The desired salt was dissolved in ethyl acetate/methanol, treated with activated charcoal, filtered, and concentrated to afford 0.137 g (3%) of 6,11-ethano-12,12-diethoxy-13,13-dimethyl-9-chloro-6,11-dihydrobenzo[b]quinolizinium perchlorate, as a tan powder.

Example 27

(a)

Following a procedure similar to that described in Example 21, a reaction mixture of 2.28 g (7.8 mmol) of 4-methylbenzo[b]quinolizinium perchlorate and 1.68 g (11.6 mmol) of 1,1-diethoxy-2,2-dimethylethylene in 25 ml of acetonitrile was stirred at room temperature for 4 hours, and then heated at 50° C. for 12 hours. Additional 1,1-diethoxy-2,2-dimethylethylene (1 g) was added and the reaction mixture was heated at 50° C. for 36 hours and cooled. The reaction mixture was filtered, the filtrate was concentrated in vacuo, and the residue purified by chromatography on silica eluting with 9% methanol/methylene chloride (0.5% TEA). The eluent was concentrated in vacuo to afford 2.6 g (76.6%) of 6,11-ethano-12,12-diethoxy-13,13-dimethyl-4-methyl-6,11-dihydrobenzo[b]quinolizinium perchlorate (Formula I: $R^1=4=CH_3$; $R^2=R^7=H$; $R^3=R^4=CH_3$; $R^5=R^6=OC_2H_5$; $X^-=ClO_4^-$), as a tan foam.

(b)

The above perchlorate in 3 ml of acetonitrile was converted to the corresponding chloride salt by passing the salt through Dowex® 1×2-200 pretreated with 0.5N HCl and eluting with water. The aqueous layer was concentrated in vacuo, the residue was triturated with 100 ml of toluene, and the organic solvent was concentrated in vacuo to afford 1.77 g (80.4 %) of 6,11-ethano-12,12-diethoxy-13,13-dimethyl-4-methyl-6,11-dihydrobenzo[b]quinolizinium chloride (Formula I: $R^1=4=CH_3$; $R^2=R^7=H$; $R^3=R^4=CH_3$; $R^5=R^6=OC_2H_5$; $X^-=Cl^-$), as a tan powder, m.p. 60°–65° C.

Example 28

(a)

Following a procedure similar to that described in Example 21, a reaction mixture of 17 g (52 benzo[b]quinolizinium hexafluorophosphate and 12.1 g (0.104 mol) of 1,1-diethoxyethylene in 250 ml of acetonitrile was stirred at room temperature for 12 hours. The reaction mixture was concentrated in vacuo, and the residue was crystallized from hot ethanol to afford 21.6 g (91.5%) of 6,11-ethano-12,12-diethoxy-6,11-dihydrobenzo[b]quinolizinium hexafluorophosphate (Formula I: $R^1=R^2=R^7=R^3=R^4=H$; $R^5=R^6=OC_2H_5$; $X^-=PF_6^-$).

(b)

The above hexafluorophosphate in a minimum amount of acetonitrile was converted to the corresponding chloride salt by passing the salt through Dowex ® 1×2-200 pretreated with 0.5N HCl and eluting with water. The aqueous layer was concentrated in vacuo (from 400 ml to 50 ml), the residual mixture was diluted with toluene, and the resulting mixture was concentrated in vacuo (<60° C.). A white solid was crystallized from methylene chloride/ethyl acetate to afford 8.49 g (52.7 %) of 6,11-ethano-12,12-diethoxy-6,11-dihydrobenzo[b]quinolizinium chloride (Formula I: $R^1=R^2=R^7=R^3=R^4=H$; $R^5=R^6=OC_2H_5 X^-=Cl^-$), as a white powder, m.p. 124°–126.5° C.

Example 29

Following a procedure similar to that described in Example 21, a reaction mixture of 0.26 g (1 mmol) of 10-bromobenzo[b]quinolizinium perchlorate and 0.28 g (2 mmol) of 1,1-diethoxy-2,2-dimethylethylene in 70 ml of acetonitrile was stirred at room temperature for 48 hours. The reaction mixture was filtered, the filtrate was concentrated in vacuo, the residue was purified by column chromatography on silica eluting with 9% methanol/methylene chloride/0.05% triethylamine. The eluent was concentrated in vacuo; to the residue was added methanol (5 mL), water (5mL), and 1 g of sodium perchlorate. The solid product was filtered, the solid residue was washed with cold water and dried (vac) to afford 0.201 g (39%) of 6,11-ethano-12,12-diethoxy-13,13-dimethyl-10-bromo-6,11-dihydrobenzo[]-quinolizinium perchlorate (Formula I: $R^1=R^7=H$; $R^2=10-Br$; $R^3=R^4=CH_3$; $R^5=R^6=OC_2H_5$; $X^-=ClO_4^-$), as a white solid, m.p. 188°–194° C.

Example 30

The perchlorate of Example 29 in a minimum amount of acetonitrile was converted to the corresponding chloride salt by passing the salt through Dowex ® 1×2-200 pretreated with 0.5N HCl and eluting with water. The aqueous layer was concentrated in vacuo, the residue was diluted with toluene, and the organic solvent was concentrated in vacuo. A solid residue was triturated with ether and filtered to afford 1.68 g (93.8%) of 6,11-ethano-12,12-diethoxy-13,13-dimethyl-10-bromo-6,11-dihydrobenzo[b]quinolizinium chloride (Formula I: $R^1=R^7=H$; $R^2=10-Br$; $R^3=R^4=CH_3$; $R^5=R^6=OC_2H_5$; $X^-=Cl^-$), m.p. 82°–88° C.

Example 31

Following a procedure similar to that described in Example 21, a reaction mixture of 15.7 mg (0.048 mmol) of 9,10-methylenedioxybenzo [b]quinolizinium perchlorate and 13.9 mg (0.09 mmol) of 1,1-diethoxy-2,2-dimethylethylene in 10 ml of acetonitrile was stirred at room temperature for 48 hours. The reaction mixture was concentrated in vacuo, and the residue purified by chromatography on silica eluting with 9% methanol/methylene chloride (0.05% TEA). The eluent was concentrated in vacuo, methanol (15 ml), water (5 ml) and 1 g of sodium perchlorate were added to the residue. A solid product was filtered, washed with water and dried to afford 4 mg (18.1%) of 6,11-ethano-12,12-diethoxy-13,13-dimethyl-9,10-methylenedioxy-6,11-dihydrobenzo[b]quinolizinium perchlorate (Formula I: $R^1=R^7=H$; $R^2=2',3'$ $(-OCH_2O-)$; $R^3=R^4=CH_3 R^5=R^6=OC_2H_5$; $X^-=ClO_4^-$).

Example 32

Following a procedure similar to that described in Example 21, a reaction mixture of 55 mg (0.15 mmol) of 10-methoxy-11-methylbenzo[b]quinolizinium perchlorate and 44 mg (0.3 mmol) of 1,1-diethoxy-2,2-dimethylethylene in 10 ml of acetonitrile was refluxed for 4 hours and then stirred at room temperature for 48 hours. Additional 1,1-diethoxy-2,2-dimethylethylene (50 mg) was added and the reaction mixture was refluxed for 12 hours and cooled. The reaction mixture was concentrated in vacuo, and the residue purified by chromatography on silica eluting with 9% methanol/methylene chloride (0.05% TEA). The eluent was concentrated in vacuo and methanol (5 ml), water (5 ml), and 1 g of sodium perchlorate were added to the residue. The solid product was filtered, washed with water and dried to afford 12.4 mg (17.4%) of 6,11-ethano-12,12-diethoxy-13,13-dimethyl-10-methoxy-11-methyl-6,11-dihydrobenzo[b]quinolizinium perchlorate (Formula I: $R^1=H$; $R^2=10-OCH_3$; $R^7=CH_3$; $R^3=R^4=CH_3$; $R^5=R^6=OC_2H_5$; $X^-=ClO_4^-$), as a white powder, mp 189°–193° C.

Example 33

Following a procedure similar to that described in Example 21, a reaction mixture of 0.1 g (0.32 mmol) of 1-methoxybenzo[b]quinolizinium perchlorate and 0.6 mg (0.6 mmol) of 1,1-diethoxy-2,2-dimethylethylene in 10 ml of acetonitrile was stirred at room temperature for 48 hours and then was refluxed for 4 hours. The reaction mixture was concentrated in vacuo, and the residue purified by chromatography on silica eluting with 9% methanol/methylene chloride (0.05% TEA). The eluent was concentrated in vacuo, the residue was dissolved in 0.5 ml of methanol and 10 ml of water, and 1 g of sodium perchlorate was added. Methanol was removed in vacuo, the aqueous solution was cooled and the perchlorate salt was filtered and then dried to afford 0.053 g (36%) of 6,11-ethano-12,12-diethoxy-13,13-dimethyl-1-methoxy-6,11-dihydrobenzo-[b]quinolizinium perchlorate (Formula I: $R^1=1-OCH_3$; $R^2=R^7=H$; $R^3=R^4=CH_3$; $R^5=R^6=OC_2H_5$; $X^-=ClO_4^-$), as a white solid, m.p.172°–174° C.

Example 34

(a)

Following a procedure similar to that described in Example 21, a reaction mixture of 3 g (7.8 mmol) of 10-isopropoxybenzo [b]quinolizinium hexafluorophosphate and 1.69 g (11.7 mmol ) of 1,1-diethoxy-2,2-dimethylethylene in 50 ml of acetonitrile was heated at 80° C. for 18 hours. The reaction mixture was cooled, filtered, and the filtrate was concentrated in vacuo to afford 4.1 g (91.3%) of 6,11-ethano-12,12-diethoxy-13,13-dimethyl-10-isopropoxy-6,11-dihydrobenzo-[b]quinolizinium hexafluorophosphate (Formula I: $R^1=R^7=H$; $R^2=10-OCH(CH_3)_2$; $R^3=R^4=CH_3$; $R^5=R^6=OC_2H_5$; $X^-=PF_6^-$), as a yellow foam.

(b)

The hexafluorophosphate of Example 34(a) (4 g; 6.9 mmol) in a minimum amount of acetonitrile was converted to the corresponding chloride salt by passing the salt through Dowex ® 1×2-200 pretreated with 0.5N HCl and eluting with water. The aqueous layer was concentrated in vacuo to afford 1.4g (47.8%) of 6,11-ethano-12,12-diethoxy-13,13-dimethyl-10-isopropoxy-6,11-dihydrobenzo[b]quinolizinium chloride (Formula I: $R^1=R^7=H$; $R^2=10$—OCH $(CH_3)_2$; $R^3=R^4=CH_3$; $R^5=R^6=OC_2H_5$; $X^-=Cl^-$), as a yellow powder, m.p. 74°-80° C.

Example 35

Following a procedure similar to that described in Example 21, a reaction mixture of 4 g (! 1.7 mmol) of 9-bromobenzo[b]quinolizinium bromide and 1.24 g (17.6 mmol) of 1,1-diethoxy-2,2-dimethylethylene in 50 ml of acetonitrile was stirred at room temperature for 1 hour and then heated at 55° C. for 3 hours. Additional 1,1-diethoxy-2,2-dimethylethylene (1 g) was added and the reaction mixture was heated at 55° C. for 26 hours and cooled. The reaction mixture was concentrated in vacuo, and the residue was triturated with ether and the organic layer was decanted.

The above residue was dissolved in nitromethane, the solution was cooled, filtered, and the filtrate was concentrated in vacuo. The residual product was purified by chromatography on silica eluting with 10% ethanol/methylene chloride and the eluent was concentrated. Water (200 ml), 10 ml methanol, and sodium perchlorate were added to the residual solid, the solution was cooled, and a white solid was filtered and triturated successively with methanol (5 ml) and warm water. The white solid was filtered and dried to afford 1.91 g (31.7%) of 6,11-ethano-12,12-diethoxy-13,13-dimethyl-9-bromo-6,11-dihydrobenzo[b]quinolizinium perchlorate (Formula I: $R^1=R^7=H$; $R^2=9$—Br; $R^3=R^4=CH_3$; $R^5=R^6=OC_2H_5$; $X^-=ClO_4^-$), m.p. 163°-165° C.

Example 36

Following procedures similar to those described hereinabove, the following known compound was prepared: 6,11-ethano-12,12-diethoxy-13-bromo-6,11-dihydrobenzo[b]quinolizinium perchlorate (Formula I: $R^1=R^2=R^7=H$; $R^3=Br$; $R^4=H$; $R^5=R^6=OC_2H_5$; $X^-=ClO_4^-$), m.p. 191°-194° C.

Examples 37 & 38

Following a procedure similar to that described in Example 21, a solution of 1,1-diethoxy-2-methylethylene (10.9 g; 0.084 mol) in 100 ml of acetonitrile was added dropwise under nitrogen to a mixture of 17.35 g (0.07 mol) of benzo[b]quinolizinium bromide and the reaction mixture was stirred at room temperature for 12 hours and then filtered. The filtrate was concentrated in vacuo, and the residue was dissolved in 300 ml of methylene chloride, heated to 30° C. and then cooled to 0° C. The solid benzo[b]quinolizinium was removed by filtration, the filtrate was concentrated to afford 22 g (87.8%) of 6,11-ethano-12,12-diethoxy-13-methyl-6,11-dihydrobenzo[b]quinolizinium bromide (as a mixture of geometric isomers), as a foam.

The above bromide (mixture) was purified by chromatography on silica eluting with pyridine/acetic acid/water (55/20/25)/ethylacetate (1.5/1), and the fraction 1 and fraction 2 were obtained. Each fraction was concentrated in vacuo, water (20 ml) and sodium perchlorate were added to the residue, and each salt was filtered.

Each residual solid isolated was dissolved in hot water/methanol, filtered, and the precipitated solid was isolated and recrystallized from water to afford 6,11-ethano-12,12-diethoxy-13-methyl-6,11-dihydrobenzo[b]quinolizinium (Formula I: $R^1=R^2=R^7=H$; $R^3=CH_3$; $R^4=H$; $R^5=R^6=OC_2H_5$; $X^-=ClO_4^-$) (Example 37), as a white solid, m.p. 159°-162° C., and 6,11-ethano-12,12-diethoxy-13-methyl-6,11-dihydrobenzo[b]quinolizinium perchlorate (Formula I: $R^1=R^2=R^7=H$; $R^3=H$; $R^4=CH_3$; $R^5=R^6=OC_2H_5$; $X^-=ClO_4^-$) (Example 38), as a white solid, m.p. 177°-180° C.

Example 39

Following a procedure similar to that described in Example 21,1,1-dipropoxy-2,2-dimethylethylene (3.69 g; 0.0214 mol) was added to a mixture of 2 g (0. 0716 mol) of benzo[b]quinolizinium perchlorate in 25 ml of acetonitrile and the reaction mixture was heated at 50° C. for 2 hours. The reaction mixture was concentrated in vacuo, and the residue was dissolved in ethyl acetate, cooled, and filtered. The filtrate was diluted with ethyl acetate, treated with activated charcoal, filtered through supercel ®, and the filtrate was concentrated in vacuo and 5 a white powder was dried (40° C.; in vacuo) to afford 1.77 g (54.8%) of 6,11-ethano-12,12-dipropoxy-13,13-dimethyl-6,11-dihydrobenzo[b]quinolizinium perchlorate (Formula I: $R^1=R^2=R^7=H$; $R^3=R^4=CH_3$; $R^5=R^6=OC_3H_7$; $X^-=ClO_4^-$), as a white powder, m.p. 150°-155° C.

Example 40

Following a procedure similar to that described in Example 21,1-methoxy-1-trimethylsilyloxy-2,2-dimethylethylene (1.24 g; 7.1 mmol) was added to a mixture of 1 g (3.58 mmol) of benzo[b]quinolizinium perchlorate in 20 ml of acetonitrile and the reaction mixture was stirred at room temperature for 2 hours. The reaction mixture was concentrated (60° C.) in vacuo, the residue (an orange foam) was dissolved in 20 ml of water and 1 ml of methanol, and the solution was briefly heated to 50° C.

The above solution was cooled and filtered to afford 1.42 g (87.7%) of 6,11-ethano-12-methoxy-12-trimethylsilyloxy-13,13-dimethyl-6,11-dihydrobenzo[b]quinolizinium perchlorate (Formula I: $R^1=R^2=R^7=H$; $R^3=R^4=CH_3$; $R^5=OCH_3$; $R^6=O-Si(CH_3)_3$; $X^-=ClO_4^-$), as a tan solid, m.p.158°-164° C.

Examples 41 & 42

Following a procedure similar to that described in Example 21, 1,1-diethoxy-2-chloroethylene (3.6 g; 24 mmol) was added to a mixture of 4 g (16.1 mmol) of benzo[b]quinolizinium bromide in 40 ml of acetonitrile and the reaction mixture was stirred at room temperature for 14 hours and then heated at 45° C. for 2 days while adding 2,2-diethoxy-1-chloroethylene (2×1 g). The reaction mixture was cooled and filtered to yield 4.1 g (59.4%) of 6,11-ethano-12,12-diethoxy-13-chloro-6,11-dihydrobenzo[b]quinolizinium bromide (Formula I: $R^1=R^2=R^7=H$; $R^3=Cl$; $R^4=H$; $R^5=R^6=OC_2H_5$; $X^-=Br^-$) (Example 41), m.p.220°-30° C. The above filtrate was concentrated in vacuo and the residue was purified by chromatography on silica (E/PAW (1:1) ) yielding fraction A and fraction B.

The fraction A was concentrated to afford an additional 40 mg of 6,11-ethano-12,12-diethoxy-13-chloro-6,11-dihydrobenzo[b]quinolizinium bromide (Example 41, isomer A). upon concentration of the fraction B, 800 mg (11.6%) of 6,11-ethano-12,12-diethoxy-13-chloro-6,11-dihydrobenzo[b]quinolizinium bromide (isomer B) was isolated. The above isomer S (bromide) was dissolved in 20 ml of water, sodium perchlorate was added to the bromide solution, and the precipitated white solid was filtered, washed with water, and dried (40° C. in vacuo for 12 hours) to afford 6,11-ethano-12,12-diethoxy-13 -chloroquinolizinium perchlorate (Formula I: $R^1=R^2=R^7=H$; $R^3=H$; $R^4=Cl$; $R^5=R^6=OC_2H_5$; $X^-=ClO_4^-$), (Example 42, isomer B), as a white solid, m.p. 184°–188° C.

Example 44

Following a procedure similar to that described in Example 21,1-(diethyl)-amino-2,2-dimethylethylene (4 g; 31 mmol) in 20 ml of acetonitrile was added at 0° C. dropwise over a 20 min. period to a mixture of 6 g (24 mmol) of acridizinium bromide in 100 ml of acetonitrile. The reaction mixture was allowed to warm to room temperature with stirring. The reaction mixture was concentrated in vacuo, the residue was dissolved in water, and $HClO_4$ was added to the aqueous solution. The white solid precipitate was filtered, washed with water and THF to afford 6.2 g (51%) of 6,11-ethano-12-(diethyl) amino-13,13-dimethyl-6,11-dihydrobenzo[b]quinolizinium diperchlorate (Formula I: $R^1=R^2=R^7=H$; $R^3=R^4=CH_3$; $R^5=N(C_2H_5)_2$; $R^6=H$; $X^-=ClO_4^-$), as a white solid, m.p. 143°–146° C.

Example 45

Following a procedure similar to that described in Example 21, a reaction mixture of 804 mg (2.5 mmol) of benzo[b]quinolizinium perchlorate and 450 mg (2.88 mmol) of 2-isopropylidene-4 (R), 6 (R)-(dimethyl)-1,3-dioxane in 50 ml of acetonitrile was stirred at room temperature for 4 hours. The mixture was filtered and the white solid was purified by chromatography on silica eluting with 9% methanol/methylene chloride. The solvent was concentrated in vacuo to afford 770 mg (63.6%) of 6,11-ethano-12,12-(2R,4R-pentanediol ketal)-13,13-dimethyl-6,11-dihydrobenzo[b]quinolizinium perchlorate (Formula I: $R^1=R^2=R^7=H$; $R^3=R^4=CH_3$; $R^5$ and $R^6$ together=(R,R)—$OCH(CH_3)CH_2CH(CH_3)O$—; $X^-=ClO_4^-$), as a white solid, m.p. 193°–196° C.

Example 46

Following a procedure similar to that described in Example 21, 1,1-diethoxy-2,2-dimethylethylene (1.29 q; 18.4 mmol) was added to a mixture of 4 g (12.3 mmol) of 9-nitrobenzo[b]quinolizinium perchlorate in 50 ml of acetonitrile and the reaction mixture was stirred at room temperature for 1 hour and then heated at 45° C. for 3 hours. After an addition of 1,1-diethoxy-2,2-dimethylethylene (1 g), the reaction mixture was heated at 55° C. for 23 hours. The reaction mixture was cooled, concentrated in vacuo, and ethyl acetate was added to the residue. The white solid precipitated was filtered and dried (40° C./vac) to afford 6,11-ethano-12,12-diethoxy-13,13-dimethyl-9-nitro-6,11-dihydrobenzo[b]quinolizinium perchlorate (Formula I: $R^1=R^7=H$; $R^2=9$—$NO_2$; $R^3=R^4=CH_3$; $R^5=R^6=OC_2H_5$; $X^-=ClO_4^-$), as a white solid, m.p. 193°–195° C.

Example 47

Following a procedure similar to that described in Example 21, 1,1-diethoxy-2,2-dimethylethylene (107 mg; 0.5 mmol) was added to a mixture of 100 mg (0.34 mmol) of 10-methylbenzo[b]quinolizinium perchlorate in 5 ml of acetonitrile and the reaction mixture was stirred at room temperature for 12 hours and then heated at 60° C. for 10 hours. After allowing the reaction mixture to stand at room temperature for 20 hours, the mixture was concentrated, a yellow residual solid was triturated with toluene, and the solvent was concentrated in vacuo. The resulting oil was treated with water/methanol (4:1), sodium perchlorate (500 mg), and methanol was removed in vacuo. The resulting tan solid was filtered and dried to afford 58 mg (39%) of 6,11-ethano-12,12-diethoxy-13,13-dimethyl-10-methyl-6,11-dihydrobenzo[b]quinolizinium perchlorate (Formula I: $R^1=R^7=H$; $R^2=10$—$CH_3$; $R^3=R^4=CH_3$; $R^5=R^6=OC_2H_5$; $X^-=ClO_4^-$), as a tan solid, m.p. 82°–91° C.

Examples 48 & 49

Following a procedure similar to that described in Example 21,1-ethoxy-2,2-dimethylethylene (1.69 g; 16 mmol) was added to a mixture of 3 g (10.7 mmol) of benzo[b]quinolizinium perchlorate in 35 ml of acetonitrile and the reaction mixture was heated at 60° C. for 12 hours. After cooling, the brown solution was purified by chromatography on silica eluting with 9% methanol/methylene chloride (0.5% TEA). The eluent was concentrated in vacuo and the residue was rechromatographed on silica (E/PAW (1.5:1) followed by E/PAW(2:i)) to afford 600 mg of 6,11-ethano-12-ethoxy-13,13-dimethyl-6,11-dihydrobenzo[b]quinolizinium perchlorate (Formula I: $R^1=R^2=R^7=H$; $R^3=R^4=CH_3$; $R^5=H$; $R^6=OC_2H_5$; $X^-=ClO_4^-$) (Example 48), as a white solid, m.p. 158°–164° C., and 40 mg of 6,11-ethano-12-ethoxy-13,13-dimethyl-6,11-dihydrorbenzo[b]quinolizinium perchlorate (Formula I: $R^1=R^2=R^7=H$; $R^3=R^4=CH_3$; $R^5=OC_2H_5$; $R^6=H$; $X^-=ClO_4^-$) (Example 49), as a white solid, m.p. 106°–108° C., respectively. Each isomer was further purified by dissolving the solid product in methylene chloride/methanol, filtering, concentrating the solvent in vacuo, and triturating with ether followed by isolation.

Example 50

Following a procedure similar to that described in Example 21,1, 1-diethoxy-2,2-dimethylethylene (77 mg; 0.53 mmol) was added to a mixture of 150 mg (0.487 mmol) of 7,10-dimethylbenzo[b]quinolizinium perchlorate in 5 ml of acetonitrile and the reaction mixture was heated with stirring at 50° C. for 8 hours and then at 65° C. for 4 hours while adding an additional 1,1-diethoxy-2,2-dimethylethylene (77 mg; 0.53 mmol). The reaction mixture was concentrated and the residual solid was crystallized from ethyl acetate/ether to afford 90 mg (41%) of 6,11-ethano-12,12-diethoxy-13,13-dimethyl-7,10-dimethyl-6,11-dihydrobenzo[b]quinolizinium perchlorate (Formula I: $R^1=R^7=H$; $R^2=7,10$—$(CH_3)_2$; $R^3=R^4=CH_3$; $R^5=R^6=OC_2H_5$; $X^-=ClO_4^-$), as an amorphous foam, m.p. 82°–90° C.

Example 51

Following a procedure similar to that described in Example 21, 1,1-diethoxy-2,2-dimethylethylene (81 mg; 0.56 mmol) was added to a mixture of 150 mg (0.51 mmol) of 11-methylbenzo[b]quinolizinium perchlorate (Bradsher and Parham J. Org. Chem. 1963, 28, 83°–85) in 5 ml of acetonitrile and the reaction mixture was heated at 50° C. for 8 hours and then at 65° C. for 12 hours while adding an additional 1,1-diethoxy-2,2-dimethylethylene (81 mg; 0.56 mmol). The reaction mixture was cooled, concentrated, and the residual oil was purified by chromatography on silica eluting with 9% methanol/methylene chloride. The eluent was concentrated and the tan residual powder was crystallized from ethyl acetate/ether to afford 180 mg (81%) of 6,11-ethano-12,12-diethoxy-13,13-dimethyl-11-methyl-6,11-dihydrobenzo[b]quinolizinium perchlorate (Formula I: $R^1=R^2=H$; $R^7=CH_3$; $R^3=R^4=CH_3$; $R^5=R^6=OC_2H_5$; $X^-=ClO_4^-$), as a tan powder, m.p. 144°–146° C.

Example 52

Following a procedure similar to that described in Example 21, 1,1-diethoxy-2,2-dimethylethylene (93 mg; 0.64 mmol) was added to a mixture of 110 mg (0.32 mmol) of 7,10-dimethoxybenzo[b]quinolizinium perchlorate in 10 ml of acetonitrile and the reaction mixture was stirred at room temperature for 48 hours and then refluxed for 4 hours. After adding an additional 1,1-diethoxy-2,2-dimethylethylene (100 mg), the mixture was refluxed for 24 hours. The mixture was concentrated and the residue was purified by chromatography on silica eluting with 9% methanol/methylene chloride (0.05% TEA). The eluent was concentrated in vacuo and 5 ml of water, 0.5 ml of methanol, and 1 g of sodium perchlorate were added to the residue. Methanol was removed in vacuo and the brown solid was filtered, washed with cold water, and dried (40° C./vac) to afford 80.9 mg (51%) of 6,11-ethano-12,12-diethoxy-13,13-dimethyl-7,10-dimethoxy-6,11-dihydrobenzo[b]quinolizinium perchlorate (Formula I: $R^1=R^7=H$; $R^2=7,10-(OCH_3)_2$; $R^3=R^4=CH_3$; $R^5=R^6=OC_2H_5$; brown solid, m.p. 212°–220° C.

Example 54

Following a procedure similar to than described in Example 21, a reaction mixture of 730 mg (2.4 mmol) of 7-methylbenzo[b]quinolizinium perchlorate and 536 mg (3.7 mmol) of 1,1-diethoxy-2,2-dimethylethylene in 10 ml of acetonitrile was stirred at room temperature for 4 hours and then heated at 50° C. for 12 hours. After adding an additional 1,1-diethoxy-2,2-dimethylethylene (1 g), the reaction mixture was heated at 50° C. for 30 hours.

The mixture was cooled, filtered, and the filtrate was concentrated in vacuo. The residue was purified by chromatography on silica eluting with 9% methanol/methylene chloride (0.5% triethylamine (TEA)). The solvent was concentrated in vacuo to afford 783 mg (75.8%) of 6,11-ethano-12,12-diethoxy-13,13-dimethyl-7-methyl-6,11-dihydrobenzo[b]quinolizinium perchlorate (Formula I: $R^1=R^7=H$; $R^2=7—CH_3$; $R^3=R^4=CH_3$; $R^5=R^6=OC_2H_5$; $X^-=ClO_4^-$).

Example 55

The perchlorate of Example 54 in 10 ml of acetonitrile was converted to the corresponding chloride salt by passing the perchlorate through 50 g of Dowex® 1×2-200 pretreated with 0.5N HCl and eluting with water. The eluent was concentrated in vacuo and the brown residual solid was triturated with toluene to afford 0.351 g of 6,11-ethano-12,12-diethoxy-13,13-dimethyl-7-methyl-6,11-dihydrobenzo[b]quinolizinium chloride (Formula I: $R^1=R^7=H$; $R^2=7—CH_3$; $R^3=R^4=CH_3$; $R^5=R^6=OC_2H_5$; $X^-=Cl^-$), as a brown glass, m.p. 49°–56° C.

Example 56

Following a procedure similar to that described in Example 21, 2-isopropylidene-4(R),5(R)-dimethyl-1,3-dioxolane (950 mg) was added to a mixture of 300 mg (0.76 mmol) of 7-acetoxy-10-t-butyl-benzo[b]quinolizinium perchlorate in 10 ml of acetonitrile and the reaction mixture was stirred at room temperature for 12 hours. The reaction mixture was concentrated in vacuo and the tan residue was washed with ether. The above tan residue was purified by chromatography on silica eluting with 8.5% ethanol/methylene chloride (0.5% TEA). The eluent was concentrated in vacuo to afford 6,11-ethano-12,12-(2R,3R-butanediol ketal)-13,13-dimethyl-7-acetoxy-10-t-butyl-6,11-dihydrobenzo[b]quinolizinium perchlorate, as a tan solid.

The ether layer was also purified by chromatography on silica eluting with 5% ethanol/methylene chloride (0.5% TEA). The eluent was concentrated in vacuo to afford 6,11-ethano-12,12-(2R,3R-butanediol ketal)-13,13-dimethyl-7-acetoxy-10-t-butyl-6,11-dihydrobenzo[b]quinolizinium perchlorate, as a tan solid. The chromatographic purifications afforded 195 mg (48%) of 6,11-ethane-12,12-(2R, 3R-butanediol ketal)-13,13-dimethyl-7-acetoxy-10-t-butyl-6,11-dihydrobenzo[b]quinolizinium perchlorate, (Formula I: $R^1=R^7=H$; $R^2=7—OAc$; 10-t-Bu; $R^3=R^4=CH_3$; $R^5$ and $R^6$ together=(R,R)—OCH(CH_3)CH(CH_3)O—; $X^-=ClO_4^-$) as a tan solid, m.p. 183°–188° C.

Example 57

Following a procedure similar to that described in Example 21, 2-isopropylidene-4R,6R-dimethyl-1,3-dioxane (150 mg; 0.96 mmol) was added to a mixture of 377 mg (0.96 mmol) of 7-acetoxy-10-t-butyl-acridizinium perchlorate in 10 ml of acetonitrile and the reaction mixture was stirred at room temperature for 4 hours and then heated at 60° C. for 3 hours. The reaction mixture was cooled, concentrated in vacuo, and the tan residue was washed with ether, and filtered to yield a tan solid.

The above tan residue was purified by chromatography on silica eluting with 8.5% ethanol/methylene chloride (0.5% TEA). The eluent was concentrated in vacuo to afford 320 mg (60%) of 6,11-ethano-12,12-(2R,4R-pentanediol ketal)-13,13-dimethyl-7-acetoxy-10-t-butyl-6,11-dihydrobenzo[b]quinolizinium perchlorate (Formula I: $R^1=R^7=H$; $R^2=7—OAc$; 10-t-Bu; $R^3=R^4=CH_3$; $R^5$ and $R^6$ together=(R,R)—OCH(CH_3)CH_2CH(CH_3)O—; $X^-=ClO_4^-$), as a tan solid, m.p. 118°–123° C.

Example 58

Following a procedure similar to that described in Example 21, 1,1-diethoxy-2,2-dimethylethylene (536 mg; 3.7 mmol) in 15 ml of acetonitrile was added to 300 mg (0.76 mmol) of 7-acetoxy-10-t-butyl-benzo[b]quinolizinium perchlorate and the reaction mixture was heated at 50° C. for 8 hours and cooled. The reaction mixture was concentrated in vacuo and the residue was purified by chromatography on silica eluting with 8% methanol/methylene chloride (0.05% TEA). The organic solvent was concentrated in vacuo and 278 mg (68.1%) of 6,11-ethano-12,12-diethoxy-13,13-dimethyl-7-acetoxy-10-t-butyl-6,11-dihydrobenzo[b]quinolizinium perchlorate (Formula I: $R^1=R^7=H$;

$R^2=7$—OAc, 10-tBu; $R^3=R^4=CH_3$; $R^5=R^6=OC_2H_5$; $X^-=ClO_4^-$), as a tan foam, m.p. 86°–95° C.

Example 59

A reaction mixture of 6,11-ethano-12,12-diethoxy-13,13-dimethyl-7-acetoxy-10-t-butyl-6,11-dihydrobenzo[b]quinolizinium perchlorate (197 mg; 0.37 mmol), 4 ml of saturated sodium bicarbonate solution, 4 ml of ethanol, and 2 ml of THF was stirred at room temperature for 4½ hours. Methylene chloride (100 ml) was added to the above reaction mixture, the resulting mixture was poured into 20 ml of 1N HCl solution (ice cold), and the acidic (pH 6) mixture was extracted with additional methylene chloride. The organic layer was dried (sodium sulfate), concentrated in vacuo, and the residue was purified by chromatography on silica eluting with 11% ethanol/methylene chloride to afford 72 mg (39.7%) of 6,11-ethano-12,12-diethoxy-13,13-dimethyl-7-hydroxy-10-t-butyl-6,11-dihydrobenzo[b]quinolizinium perchlorate (Formula I: $R^1=R^7=H$; $R^2=7$—OH; 10-t-Bu; $R^3=R^4=CH_3$; $R^5=R^6=OC_2H_5$; $X^-=ClO_4^-$), as a brown solid, m.p. 210°–215° C.

Examples 60 & 61

Following a procedure similar to that described in Example 21, 1-diethylamino propene (3.56 g; 31 mmol) in 20 ml of acetonitrile was added dropwise at 0° C. to a mixture of 6 g (24.2 mmol) of benzo[b]quinolizinium bromide in 100 ml of acetonitrile over a 20 min. period. The mixture was allowed to warm to room temperature, filtered, and concentrated in vacuo (also removed enamine). The tan residual oil was purified by chromatography on silica eluting with pyridine/acetic acid/water(55/20/25)(PAW)/ethyl acetate (1.5:1) yielding fraction A and fraction B. Each fraction was concentrated in vacuo (<50° C.), the residue was dissolved in water, sodium perchlorate and HClO$_4$ were added to the aqueous solution, and the resulting solid was isolated by filtration to afford 6,11-ethano-12-(diethyl)amino-13-methyl-6,11-dihydrobenzo[b]quinolizinium diperchlorate (Formula I: $R^1=R^2=R^7=H$; $R^3=H$; $R^4=CH_3$; $R^5=N(C_2H_5)_2$; $R^6=H$; $X^-=ClO_4^-$) (Example 60; isomer A), as an off-white solid, m.p. 175°–180° C., and 6,11-ethano-12-(diethyl) amino-13-methyl-6,11-dihydrobenzo[b]quinolizinium diperchlorate (Formula I: $R^1=R^2=R^7=H$; $R^3=CH_3$; $R^4=H$; $R^5=N(C_2H_5)_2$; $R^6=H$; $X^-=ClO_4^-$) (Example 61; isomer B), respectively.

Example 62

Following a procedure similar to that described in Example 21,1-diethylaminopropene (3.56 g; 31 mmol) in 20 ml of acetonitrile was added dropwise at 0° C. to a mixture of 6 g (24.2 mmol) of benzo[b]quinolizium bromide in 100 ml of acetonitrile over a 20 min. period. The mixture was allowed to warm to room temperature and stirred for 1 hour. The reaction mixture was filtered and the filtrate was concentrated in vacuo (<40° C.) yielding an orange foam.

The orange residual foam was dissolved in 60 ml of water and 10 g of sodium perchlorate was added. The brown gum formed was separated by decantation of the aqueous layer, and 40 ml of water and 4 ml of HClO$_4$ were added to the residue. The white solid precipitated was filtered, dissolved in 100 ml of THF, and the THF solution was refluxed briefly and cooled. The white solid product was filtered and dried to afford 3.3 g of 6,11-ethano-12-(diethyl) amino-13-methyl-6,11-dihydrobenzo[b]quinolizinium perchlorate (Formula I: $R^1=R^2=R^7=H$; $R^3=H$; $R^4=CH_3$; $R^5=N(C_2H_5)_2$; $R^6=H$; $X^-=ClO_4^-$; as a mixture of geometric isomers), as a white solid, m.p. 147°–149° C.

Example 63

Following procedures similar to those described hereinabove, or by utilizing procedures which are known in the art, the following known compounds (Examples 63 (a)–63 (m)) were prepared and, unexpectedly, they were found to bind to the PCP receptor and are thus useful in the treatment or prevention of neurodegenerative disorders or neurotoxic injuries.

(a)

12,12-Diethoxy-6,11-ethano-6,11-dihydrobenzo[b]quinolizinium bromide.

(b)

12,12-Diethoxy-13-bromo-6,11-ethano-6,11-dihydrobenzo[b]quinolizinium perchlorate.

(c)

11-Methyl-12,12-diethoxy-6,11-ethano-6,11-dihydrobenzo[b]quinolizinium perchlorate.

(d)

12,12-Diethoxy-13-methyl-6,11-ethano-6,11-dihydrobenzo[b]quinolizinium perchlorate as a mixture of geometric isomers.

(e)

7,10-Dimethyl-12,12-diethoxy-13-methyl-6,11-ethano-6,11-dihydrobenzo[b]quinolizinium perchlorate.

(f)

7-Methyl-12,12-diethoxy-6,11-ethano-6,11-dihydrobenzo[b]quinolizinium perchlorate.

(g)

9-Methyl-12,12-diethoxy-6,11-ethano-6,11-dihydrobenzo[b]quinolizinium perchlorate.

(h)

7,10-Dimethyl-12,12-diethoxy-6,11-ethano-6,11-dihydrobenzo[b]quinolizinium perchlorate.

(i)

8,9-Dimethyl-12,12-diethoxy-6,11-ethano-6,11-dihydrobenzo[b]quinolizinium perchlorate.

(j)

12,12-Diethylamino-13-phenyl-6,11-ethano-6,11-dihydrobenzo[b]quinolizinium perchlorate.

(k)

7-Methyl-12,12-diethoxy-13-methyl-6,11-ethano-6,11-dihydrobenzo[b]quinolizinium perchlorate.

(l)

11-Methyl-12,12-diethoxy-13-methyl-6,11-ethano-6,11-dihydrobenzo[b]quinolizinium perchlorate.

(m)

12,12-dimethoxy-13,13-dimethyl-6,11-ethano-6,11-dihydrobenzo[b]quinolizinium perchlorate.

Example 64

Following a procedure similar to that described in Example 1 (a), but substituting an appropriately substituted benzo[b]quinolizinium salt of Formula IV for benzo[b]quinolizinium bromide, it is contemplated that there can be prepared the following compounds of Formula I:

(a)

9-Trichloromethyl-12,12-diethoxy-13,13-dimethyl-6,11-ethano-6,11-dihydrobenzo[b]quinolizinium hexafluorophosphate.

(b)

4-Bromo-12,12-diethoxy-13,13-dimethyl-6,11-ethano-6,11-dihydrobenzo [b]quinolizinium perchlorate.

(c)

2-Methyl-12,12-diethoxy-13,13-dimethyl-6,11-ethano-6,11-dihydrobenzo [b]quinolizinium perchlorate.

BIOLOGICAL TEST RESULTS

Representative examples of the compounds of the invention have been found to possess valuable pharmacological properties. In particular, they have been found to bind to the PCP receptor and are thus non-competitive blockers (antagonists) of the effects which excitatory amino acids, such as glutamate, have upon the NMDA receptor. The compounds of the invention are thus useful in the treatment or prevention of neurodegenerative disorders such as Huntington's disease, Alzheimer's disease, amyotrophic lateral sclerosis, Down's Syndrome, senile dementia, glutaric acidaemia type I, multi-infarct dementia, Parkinson's disease, viral encephalopathies (which include, but are not limited thereto, dementia associated with HIV infections) and neuronal damage associated with uncontrolled seizures, as well as in the treatment or prevention of neurotoxic injuries associated with ischemic, hypoxic; or hypoglycemic conditions. Representative examples of such ischemic, hypoxic, or hypoglycemic conditions include strokes or cerebrovascular accidents, carbon monoxide poisoning, hyperinsulinemia, cardiac arrest, drownings, suffocation, spinal or head trauma, neonatal anoxic trauma, coronary artery bypass graft, and perinatal asphyxia.

The compounds of the invention are particularly useful in the treatment or prevention of neurotoxic injuries associated with ischemic, hypoxic; or hypoglycemic conditions, and especially ischemic, hypoxic, or hypoglycemic conditions which are associated with stroke.

The pharmacological properties of representative examples of the compounds of the invention was demonstrated by conventional in vitro and in vivo biological test procedures such as the following:

[$^3$H]TCP Radioreceptor Assay (internal screen)

[$^3$H]TCP binding to PCP recognition sites was performed as described by Vignon et al. Brain Research 1983, 280, 194°197. Male Sprague-Dawley rats were sacrificed by decapitation, and whole brains were homogenized in 10 volumes (wt/vol) of cold Tris-HCl buffer (50 mM, pH 7.7) using a Brinkmann Polytron (setting 6, 30 sec). The homogenate was centrifuged at 40,000×g for 10 min at 4° C. The supernatant was decanted, and the homogenization and centrifugation steps were repeated twice as described above. Following this, the pellet was resuspended in Tris-HCl (5 mM, pH 7.7) at a tissue concentration of 0.5°0.75 g/ml, and one ml aliquots were frozen at −70° C. until use. The binding characteristics for PCP recognition sites were not altered by the freezing of membrane suspensions.

On the day of the assay, membrane aliquots were thawed, resuspended in fresh 5 mM Tris-HCl buffer at a tissue concentration of 1 mg/ml, and stored on ice until use. Each assay tube contained 100 μl of [$^3$H]TCP at a final concentration of approximately 1 nM, 100 μl of various concentrations of the compounds of interest, 500 μl of the tissue suspension and 300 of buffer to a final assay volume of 1 ml and a final protein concentration of 0.5 mg/tube. Non-specific binding was defined by addition of a final concentration of 100 μM PCP to blank tubes. All tubes were incubated at room temperature for 25 min before termination of the reaction by rapid filtration over Whatman GF/B glass fiber filters that had been presoaked in a solution of 0.5% polyethylenimine for at least 1 hr prior to use. Filters were washed with three 4 ml volumes of cold Tris buffer. Following addition of scintillation cocktail, the amount of bound radioactivity was determined by liquid scintillation spectrometry using a Beckman LS 5000TA liquid scintillation counter with an efficiency for tritium of approximately 55%. Inhibition constants (Ki values) were calculated using the EBDA/LIGAND program (McPherson, J. Pharmacol. Meth. 1985, 14, 213–228), purchased from Elsevier/Biosoft, Inc. Results are reported as Ki values or as a percent (%) inhibition of binding at 10

Representative compounds of the invention were also tested in an external [$^3$H]TCP radioreceptor assay using the following protocol:

[$^3$H]TCP Radioreceptor Assay (external screen)

A procedure similar to that described above for the [$^3$H]TCP radioreceptor assay (internal screen) was utilized except that the whole rat forebrain membranes were incubated at 25° C. for 60 minutes rather than at room temperature for 25 minutes, before termination of the reaction. The results are reported as a percent (%) inhibition of binding at 10 μM.

Antagonism of NMDA-induced Neurotoxicity in Cultured Neurons

Preparation of Cultured Cortical Neurons

Pregnant, Swiss-Webster mice were obtained from Taconic Farms (Germantown, New York) and sacrificed 16 days post conception. Fetuses were removed and placed in a sterile dish containing Hank's balanced salt solution (HBSS), pH 7.4. Brain cortices were dissected, meninges were removed, the tissue was minced and placed into a solution of HBSS containing 0.25% (w/v) trypsin at 37° C. for 15 minutes. Tissue was then triturated with a sterile pasteur pipet, diluted with minimal essential media (Gibco 330-1430), pH 7.4, supplemented with 10% horse serum, 10% fetal calf serum, 2 mM l-glutamine, 21 mM d-glucose, 2.2 g/L sodium bicarbonate, 1000 u/ml penicillin, and 1,000 μg/ml streptomycin. Cells were plated onto Falcon primaria 96 well plates at a final density of 50,000 cells/well and incubated at 37° C. in the presence of 5% (v/v) carbon dioxide. After 5 days, plating media was replaced with maintenance media containing minimal essential media (Gibco 330-1430), pH 7.4, supplemented with 10% horse serum, 10% 1-glutamine, 21 mM d-glucose, 2.2 g/l sodium bicarbonate, 1,000 U/ml penicillin, 1,000 µg/ml streptomycin, and 10 µM cytosine arabinoside. On days 7 and 10, media was replaced with maintenance media as above lacking the cytosine arabinoside. Experiments were conducted on day 13.

Neuroprotection Assessment

Day 13 cultured cortical neurons were washed twice with minimal essential media, pH 7.4 and then exposed for 30 minutes to 500 µM N-methyl-D-aspartic acid (NMDA) with or without varying concentrations of test agents. Dizocilpine (MK-801) at a final concentration of 10 µM MK-801 was routinely included as a positive control. MK-801 and test agents were prepared in minimal essential media supplemented with 21 mM d-glucose and 2.2 g/L sodium bicarbonate (MEM). After 30 minutes, media was replaced with MEM alone. Exposure of neurons to test agents was limited to the NMDA treatment period. Twenty-four hours after removal of NMDA, an aliquot of media from each well was removed for assessment of cell injury by determining lactate dehydrogenase (LDH) activity by. the method of Wroblewski and LaDue Proc. Soc. Exp. Biol. Med. 1955, 90, 210–213. The results are expressed as an $IC_{50}$ (in nM) value (concentration causing 50% inhibition) for the antagonism of NMDA—induced neurotoxicity.

Table 1 summarizes the results obtained from the testing of representative compounds of the invention in the [$^3$H] TCP radioreceptor assay (internal screen and external screen) as well as in the antagonism of NMDA-induced neurotoxicity in cultured neurons.

TABLE 1

| Example Number | [$^3$H]TCP (internal screen) $K_i$(nM) or Percent inhibition @ 10µ M | [$^3$H]TCP (external screen) Percent inhibition @ 10µ M | Antagonism of NMDA-induced neurotoxicity ($IC_{50}$ in nM) |
|---|---|---|---|
| 1(a) | 8.40 | — | 17 |
| 2 | 5.30 | — | 30–50 |
| 3 | 5.56 | — | — |
| 4 | 5.66 | — | — |
| 5 | 5.25 | — | — |
| 7(b) | 14.1 | — | — |
| 8 | 5181 | — | — |
| 9 | 11% | — | — |
| 10(b) | 614 | — | — |
| 10(c) | 365 | — | — |
| 11 | 497 | — | — |
| 12(c) | 4.03 | — | 26 |
| 13(c) | 11.0 | — | 50 |
| 15(a) | 26.4 | — | — |
| 15(b) | 7.87 | — | — |
| 15(c) | 6.90 | — | — |
| 16 | 1873 | — | — |
| 17(c) | 10.6 | — | — |
| 18 | 4000 | — | — |
| 19(b) | 13.2 | — | — |
| 19(d) | 10.4 | — | 21.8 |
| 20(a) | 3.52 | — | 157 |
| 20(c) | 7.05 | — | — |
| 22(b) | 3298 | — | — |
| 23(b) | 407 | — | — |
| 24(b) | 272 | — | — |
| 25(b) | 147 | — | — |
| 26 | 12.4 | — | — |
| 27(b) | 314 | — | — |
| 28(b) | 4269 | — | 95500 |
| 29 | 132 | — | 1040 |
| 30 | 107 | — | — |
| 31 | 7.42 | — | — |
| 32 | 63.7 | — | — |
| 33 | 25.8 | — | — |
| 34(b) | 47.5 | — | — |
| 35 | 61.5 | — | 173 |
| 36 | 20.4 | — | — |
| 37 | 115 | — | 810 |
| 38 | 33.8 | — | 1160 |
| 39 | 11.5 | — | 85 |
| 40 | 1595 | — | — |
| 41 | 67 | — | 445 |
| 42 | 319 | — | — |
| 44 | 501 | — | — |
| 45 | 517 | — | — |
| 46 | 2764 | — | 15270 |
| 47 | 45.5 | — | — |
| 48 | 2149 | — | — |
| 49 | 515 | — | — |
| 51 | 11.3 | — | 32.4 |
| 52 | 33% | — | — |
| 55 | 455 | — | — |
| 56 | 24% | — | — |
| 57 | 18% | — | — |
| 58 | 12% | — | — |
| 61 | 5415 | — | — |
| 62 | 12203 | — | — |
| 63(a) | 3592 | — | — |
| 63(b) | 20.4 | — | — |
| 63(c) | 9298 | 0 | — |
| 63(d) | 49.3 | — | — |
| 63(e) | 255 | 65 | — |
| 63(f) | 7433 | 34 | — |
| 63(g) | 68% | 0 | — |
| 63(h) | 65% | 52 | — |
| 63(i) | 2265 | 35 | — |
| 63(j) | 14389 | — | — |
| 63(k) | 2456 | — | — |
| 63(l) | 39.3 | — | — |
| 63(m) | 111 | — | — |

Middle Cerebral Artery Occlusion (MCAO) Model with Reperfusion

A 3-vessel rat ischemia model similar to those that have been extensively described in the literature (e.g. Stroke 17, 738–743 (1986), Stroke 20, 513–518 (1989)) was utilized. Under isoflurane anesthesia the right middle cerebral artery (via an approach through the temporalis muscle) and both common carotid arteries were reversibly occluded for varying durations between 60 minutes and 120 minutes. Both male Long Evans hooded rats and male Sprague-Dawley rats weighing between 300 and 420 grams were used. The animals' temperature was maintained throughout the study with heat lamps. A femoral vein and the ipsilateral femoral artery were cannulated for intravenous infusion and arterial blood pressure measurements and blood samples. Infusions of the test compounds were initiated 30 minutes prior to occlusion at a rate of 40 microliters per minute. After reinitiation of blood flow the animals were allowed to regain consciousness. Six hours post-initiation of ischemia the animals were sacrificed and the extent of neuronal damage was quantified with TTC staining. The results are expressed as a percent inhibition (±SEM) of infarct and penumbra region.

Table 2 summarizes the results obtained from the testing of representative compounds of the invention in the MCAO model.

TABLE 2

| Example Number | Dose (mg Test Compound/ kg/min) | % Inhibition (+/− SEM) |
|---|---|---|
| 2 | 0.03 | 36 +/− 10 |
|  | 0.10 | 64 +/− 6 |
|  | 0.01 | 0 +/− 12 |
|  | 0.03 | 13 +/− 10 |
|  | 0.03 | 24 +/− 12 |
| 12c | 0.03 | 42 +/− 6 |
|  | 0.10 | 52 +/− 8 |
|  | 0.01 | 18 +/− 24 |
|  | 0.03 | 16 +/− 15 |
|  | 0.10 | 60 +/− 13 |
|  | 0.10 | 66 +/− 20 |
|  | 0.03 | 44 +/− 15 |
|  | 0.10 | 64 +/− 14 |
|  | 0.03 | 61 +/− 11 |
|  | 0.10 | 79 +/− 9 |

The compounds of the invention can be prepared for pharmaceutical use by conventional pharmaceutical procedures that are well known in the art; that is, by formulating a pharmaceutical composition which comprises compounds of the invention or their pharmaceutically acceptable salts together with one or more physiologically acceptable carriers, adjuvants, diluents or vehicles, for oral administration in solid or liquid form, parenteral administration, topical administration or aerosol inhalation administration, and the like.

Solid compositions for oral administration include compressed tablets, pills, powders and granules. In such solid compositions, the active compound is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilizing, preserving, wetting, emulsifying and dispersing agents.

Preparations according to the invention for topical administration or aerosol inhalation administration include dissolving or suspending a compound of the invention in a pharmaceutically acceptable vehicle such as water, aqueous alcohol, glycol, oil solution or oil-water emulsion, and the like.

If desired, the compounds of the invention can further be incorporated into slow release or targeted delivery systems such as polymer matrices, liposomes, and microspheres.

The percentage of active component in such compositions may be varied so that a suitable dosage is obtained. The dosage administered to a particular patient is variable depending upon the clinician's judgment using as criteria: The route of administration, the duration of treatment, the size and physical condition of the patient, the potency of the active component and the patient's response thereto. An effective dosage amount of the active component can thus readily be determined by the clinician after a consideration of all criteria and using his best judgment on the patient's behalf.

We claim:

1. A compound of the formula:

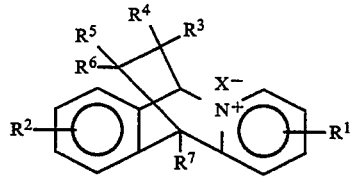

wherein:
$R^1$ is hydrogen, or from one to four, the same or different, substituents in any of the 1-, 2-, 3-, or 4-positions selected from the group consisting of lower-alkoxy, lower-alkyl, and halogen;
$R^2$ is hydrogen, or from one to four, the same or different, substituents in any of the 7-, 8-, 9-, or 10-positions selected from the group consisting of lower-alkyl, lower-alkanoyloxy, halogen, nitro, hydroxy, lower-alkoxy, methylenedioxy, polyfluorolower-alkyl and polychlorolower-alkyl;
$R^3$ and $R^4$ are the same or different lower-alkyl;
$R^5$ and $R^6$ are independently selected from the group consisting of hydrogen, lower-alkoxy, trilower-alkylsilyloxy and dilower-alkylamino; or $R^5$ and $R^6$ together represent —O—CHR$^8$—(CH$_2$)$_n$CH-R$^9$—O— wherein n is zero or one and $R^8$ and $R^9$ are independently hydrogen, lower-alkyl, or phenyl-lower-alkoxy-lower-alkyl;
$R^7$ is hydrogen, or lower-alkyl; and
$X^-$ is an anion;
or a pharmaceutically acceptable acid-addition salt of basic members thereof; or a hydrate thereof; or a stereoisomer thereof; with the proviso that when $R^1$ $R^2$ and $R^7$ are hydrogen, $R^3$ and $R^4$ are methyl and $X^-$ is $ClO_4^-$, $R^5$ and $R^6$ together cannot be —O—CH(CH$_3$)CH(CH$_3$)—O—; further provided that $R^5$ and $R^6$ cannot both simultaneously be hydrogen; still further provided that when $R^1$, $R^2$ and $R^7$ are hydrogen, $R^3$ and $R^4$ are methyl, and $X^-$ is $ClO_4^-$, $R^5$ and $R^6$ cannot simultaneously be methoxy.

2. A compound according to claim 1 wherein:
$R^1$ is hydrogen, or one substituent in any of the 1-, 2-, 3- or 4-positions selected from the group consisting of lower-alkoxy, lower-alkyl and halogen; and
$R^2$ is hydrogen, or from one to two, the same or different, substituents in any of the 7-, 8-, 9-, or 10-positions selected from the group consisting of lower-alkyl, lower-alkanoyloxy, halogen, nitro, hydroxy, lower-alkoxy, methylenedioxy, polyfluorolower-alkyl, and polychlorolower-alkyl.

3. A compound according to claim 2 wherein:
$R^1$ is hydrogen, or one substituent in any of the 1-, 2-, 3- or 4-positions selected from the group consisting of lower-alkoxy, and lower-alkyl;

$R^2$ is hydrogen, or from one to two, the same or different, substituents in any of the 7-, 8-, 9- or 10-positions selected from the group consisting of lower-alkyl, lower-alkanoyloxy, halogen, nitro, hydroxy, lower-alkoxy, methylenedioxy, and polyfluorolower-alkyl; and $R^3$ and $R^4$ are the same lower-alkyl.

4. A compound according to claim 3 wherein:

$R^1$ is hydrogen, 1-lower-alkoxy, or 4-lower-alkyl; and $R^2$ is hydrogen, or from one to two, the same or different, substituents in any of the 7-, 8-, 9- or 10-positions selected from the group consisting of lower-alkyl, acetoxy, halogen, nitro, hydroxy, lower-alkoxy, methylenedioxy and trifluoromethyl.

5. A compound according to claim 4 wherein $R^1$ is hydrogen, 1-methoxy or 4-methyl; and $R^2$ is hydrogen, or from one to two, the same or different, substituents in any of the 7-, 8-, 9- or 10-positions selected from the group consisting of methyl, tertbutyl, acetoxy, bromine, chlorine, fluorine, nitro, hydroxy, methoxy, isopropoxy, methylenedioxy and trifluoromethyl.

6. A compound according to claim 5 wherein $R^3$ and $R^4$ are both methyl or ethyl; and $R^7$ is hydrogen or methyl.

7. A compound according to claim 6 wherein $R^5$ and $R^6$ are independently selected from the group consisting of hydrogen, lower-alkoxy, trimethylsilyloxy and diethylamino; or $R^5$ and $R^6$ together represent $-OCHR^8(CH_2)_nCHR^9-O-$ wherein n is zero or one and $R^8$ and $R^9$ are simultaneously hydrogen, lower-alkyl or phenyl-lower-alkoxy-lower-alkyl.

8. A compound according to claim 7 wherein $R^5$ and $R^6$ are independently selected from the group consisting of hydrogen, methoxy, ethoxy, propoxy, trimethylsilyloxy, and diethylamino; or $R^5$ and $R^6$ together represent $-OCHR^8 (CH_2)_nCHR^9-O-$ wherein n is zero or one and $R^8$ and $R^9$ are simultaneously hydrogen, methyl, or phenylmethoxymethyl.

9. A compound according to claim 8 selected from the group consisting of:

12,12-dipropoxy-13,13-dimethyl-6,11-ethano-6,11-dihydrobenzo[b]quinolizinium $X^-$;

11-methyl-12,12-diethoxy-13,13-dimethyl- 6,11-ethano- 6,11-dihydrobenzo[b]quinolizinium $X^-$;

9-methoxy-12,12 -diethoxy-13,13-dimethyl-6,11-ethano-6,11-dihydrobenzo[b]quinolizinium $X^-$;

10-methoxy-12,12 -diethoxy-13,13 -dimethyl -6,11-ethano-6,11-dihydrobenzo[b]quinolizinium $X^-$;

12,12-diethoxy-13,13-diethyl-6,11-ethano-6,11-dihydrobenzo[b]quinolizinium $X^-$; and 12,12-diethoxy-13,13-dimethyl-6,11-ethano-6,11-dihydrobenzo[b]quinolizinium $X^-$.

10. A compound according to claim 9 selected from the group consisting of:

12,12-dipropoxy-13,13-dimethyl-6,11-ethano-6,11-dihydrobenzo[b]quinolizinium perchlorate;

11-methyl-12,12-diethoxy-13,13-dimethyl-6,11-ethano-6,11-dihydrobenzo[b]quinolizinium perchlorate;

11-methyl-12,12-diethoxy-13,13-dimethyl-6,11-ethano-6,11-dihydrobenzo[b]quinolizinium chloride;

9-methoxy-12,12-diethoxy-13,13-dimethyl-6,11-ethano-6,11-dihydrobenzo[b]quinolizinium·$PF_6^-$;

9-methoxy-12,12-diethoxy-13,13-dimethyl-6,11-ethano-6,11-dihydrobenzo[b]quinolizinium chloride;

10-methoxy-12,12-diethoxy-13,13-dimethyl-6,11-ethano-6,11-dihydrobenzo[b]quinolizinium perchlorate;

10-methoxy-12,12-diethoxy-13,13-dimethyl-6,11-ethano-6,11-dihydrobenzo[b]quinolizinium chloride;

12,12-diethoxy-13,13-diethyl-6,11-ethano-6,11-dihydrobenzo[b]quinolizinium perchlorate; and 12,12-diethoxy-13,13-dimethyl-6,11-ethano-6,11-dihydrobenzo[b]quinolizinium $X^-$, wherein $X^-$ is $ClO_4^-$, $Cl^-$, $PF_6^-$, $[(-)-DBT]^-$, $[(+)-DBT]^-$, (S)-(+)—$CH_3C(Ph)(OH)CO_2^-$, or (1S)-(−)-$C_{10}H_{13}O_4^-$.

11. 9-Methoxy-12,12-diethoxy-13,13-dimethyl-6,11-ethano-6,11-dihydrobenzo[b]quinolizinium-$PF_6^-$ according to claim 10.

12. 10-Methoxy-12,12-diethoxy-13,13-dimethyl-6,11-ethano-6,11-dihydrobenzo[b]quinolizinium chloride according to claim 10.

13. (−)-12,12-diethoxy-13,13-dimethyl-6,11-ethano-6,11-dihydrobenzo[b]quinolizinium chloride according to claim 10.

14. A compound of the formula:

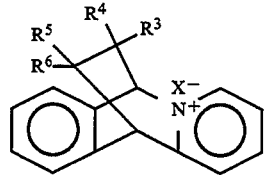

wherein:

$R^3$ and $R^4$ are independently hydrogen, lower-alkoxy, or chlorine;

$R^5$ and $R^6$ are the same or different lower-alkoxy; and $X^-$ is an anion;

or a stereoisomer thereof; with the proviso that $R^3$ and $R^4$ cannot both simultaneously be hydrogen.

15. A compound according to claim 14 wherein $R^3$ and $R^4$ are independently hydrogen, ethoxy, or chlorine; and $R^5$ and $R^6$ are the same lower-alkoxy.

16. A compound according to claim 15 wherein $R^5$ and $R^6$ are ethoxy.

17. A compound according to claim 16 wherein $R^3$ is chlorine, $R^4$ is hydrogen, $R^5$ and $R^6$ are ethoxy and $X^-$ is $Br^-$; or $R^3$ is hydrogen, $R^4$ is chlorine, $R^5$ and $R^6$ are ethoxy and $X^-$ is $ClO_4^-$.

18. 12,12,13,13-tetraethoxy-6,11-ethano-6,11-dihydrobenzo[b]quinolizinium perchlorate according to claim 16.

19. A compound of the formula:

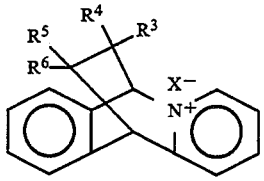

wherein:

$R^3$ and $R^4$ are independently hydrogen, or lower-alkyl;

$R^5$ and $R^6$ are independently hydrogen, or dilower-alkylamino; and $X^-$ is an anion;

or a pharmaceutically acceptable acid-addition salt of basic members thereof; or a stereoisomer thereof; with the proviso that $R^3$ and $R^4$ cannot simultaneously be lower-alkyl; further provided that $R^5$ and $R^6$ cannot simultaneously be hydrogen.

20. A compound according to claim 19 wherein $R^3$ and $R^4$ are independently hydrogen, or methyl; and $R^5$ and $R^6$ are independently hydrogen, or diethylamino.

21. 12-diethylamino-13-methyl-6,11-ethano-6,11-dihydrobenzo[b]quinolizinium perchlorate according to claim 20.

22. A pharmaceutical composition which comprises an effective amount of a compound of the formula:

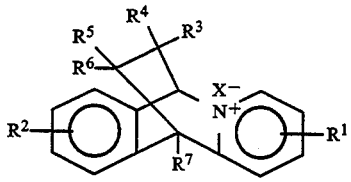

wherein:
$R^1$ is hydrogen, or from one to four, the same or different, substituents in any of the 1-, 2-, 3-, or 4-positions selected from the group consisting of lower-alkoxy, lower-alkyl and halogen;

$R^2$ is hydrogen, or from one to four, the same or different, substituents in any of the 7-, 8-, 9-, or 10-positions selected from the group consisting of lower-alkyl, lower-alkanoyloxy, halogen, nitro, hydroxy, lower-alkoxy, methylenedioxy, polyfluorolower-alkyl, and polychlorolower-alkyl;

$R^3$ and $R^4$ are independently selected from the group consisting of hydrogen, lower-alkoxy, halogen, lower-alkyl, and phenyl;

$R^5$ and $R^6$ are independently selected from the group consisting of hydrogen, lower-alkoxy, trilower-alkylsilyloxy and dilower-alkylamino; or $R^5$ and $R^6$ together represent —O—CHR$^8$(CH$_2$)$_n$CHR$^9$—O— wherein n is zero or one and $R^8$ and $R^9$ are independently hydrogen, lower-alkyl, or phenyl-lower-alkoxy-lower-alkyl;

$R^7$ is hydrogen, or lower-alkyl; and $X^-$ is an anion;

or a pharmaceutically acceptable acid-addition salt of basic members thereof; or a hydrate thereof; or a stereoisomer thereof; together with a pharmaceutically acceptable carrier, adjuvant, diluent or vehicle; with the proviso that when $R^1$, $R^3$ $R^4$ and $R^7$ are hydrogen, $R^5$ and $R^6$ are ethoxy and $X^-$ is $ClO_4^-$, $R^2$ cannot be 7,10-diacetoxy or 7-acetoxy-10-tert-butyl; further provided that when $R^1$ $R^2$ and $R^7$ are hydrogen, $R^1$, $R^3$ and $R^4$ are methyl and $X^-$ is $ClO_4^-$, $R^5$ and $R^6$ together cannot be —O—CH(CH$_3$)CH(CH$_3$)—O—; still further provided that when $R^1$, $R^4$, $R^5$ and $R^7$ are hydrogen, $R^3$ and $R^6$ are ethoxy and $X^-$ is $ClO_4^-$, $R^2$ cannot be 7—NO$_2$; still further provided that $R^5$ and $R^6$ cannot both simultaneously be hydrogen.

23. A pharmaceutical composition according to claim 22 wherein:

$R^1$ is hydrogen, or one substituent in any of the 1-, 2-, 3-, or 4-positions selected from the group consisting of lower-alkoxy, and lower-alkyl; and $R^2$ is hydrogen, or from one to two, the same or different, substituents in any of the 7-, 8-, 9-, or 10-positions selected from the group consisting of lower-alkyl, lower-alkanoyloxy, halogen, nitro, hydroxy, lower-alkoxy, methylenedioxy, and polyfluorolower-alkyl.

24. A pharmaceutical composition according to claim 23 wherein:

$R^1$ is hydrogen, 1-lower-alkoxy, or 4-lower-alkyl; and $R^2$ is hydrogen, or from one to two, the same or different, substituents in any of the 7-, 8-, 9-, or 10-positions selected from the group consisting of lower-alkyl, acetoxy, halogen, nitro, hydroxy, lower-alkoxy, methylenedioxy, and trifluoromethyl.

25. A pharmaceutical composition according to claim 24 wherein:

$R^1$ is hydrogen, 1-methoxy, or 4-methyl; and $R^2$ is hydrogen, or from one to two, the same or different, substituents in any of the 7-, 8-, 9-, or 10-positions selected from the group consisting of methyl, tert-butyl, acetoxy, bromine, chlorine, fluorine, nitro, hydroxy, methoxy, isopropoxy, methylenedioxy and trifluoromethyl.

26. A pharmaceutical composition according to claim 25 wherein $R^3$ and $R^4$ are independently selected from the group consisting of hydrogen, ethoxy, bromine, chlorine, methyl, ethyl and phenyl; and $R^7$ is hydrogen or methyl.

27. A pharmaceutical composition according to claim 26 wherein $R^5$ and $R^6$ are independently selected from the group consisting of hydrogen, methoxy, ethoxy, propoxy, trimethylsilyloxy, and diethylamino; or $R^5$ and $R^6$ together represent —OCHR$^8$(CH$_2$)$_n$CHR$^9$O— wherein n is zero or one and $R^8$ and $R^9$ are simultaneously hydrogen, methyl, or phenylmethoxymethyl.

28. A pharmaceutical composition according to claim 25 wherein $R^3$ and $R^4$ are the same lower-alkyl.

29. A pharmaceutical composition according to claim 28 wherein $R^3$ and $R^4$ are both methyl, or ethyl, and $R^7$ is hydrogen, or methyl.

30. A pharmaceutical composition according to claim 29 wherein:

$R^5$ and $R^6$ are independently selected from the group consisting of hydrogen, methoxy, ethoxy, propoxy, trimethylsilyloxy, and diethylamino; or $R^5$ and $R^6$ together represent —OCHR$^8$(CH$_2$)$_n$CHR$^9$—O— wherein n is zero or one and $R^8$ and $R^9$ are simultaneously hydrogen, methyl, or phenylmethoxymethyl.

31. A pharmaceutical composition according to claim 30 wherein the compound is 9-methoxy-12,12-diethoxy-13,13-dimethyl-6,11-ethano-6,11-dihydrobenzo[b]quinolizinium-PF$_6^-$.

32. A pharmaceutical composition according to claim 30 wherein the compound is 10-methoxy-12,12-diethoxy-13,13-dimethyl-6,11-ethano-6,11-dihydrobenzo[b]quinolizinium chloride.

33. A pharmaceutical composition according to claim 30 wherein the compound is (—)-12,12-diethoxy-13,13-dimethyl-6,11-ethano-6,11-dihydrobenzo[b]quinolizinium chloride.

34. A method for the treatment or prevention of neurodegenerative disorders or neurotoxic injuries which comprises administering to a patient in need of such treatment an effective amount of a compound of the formula:

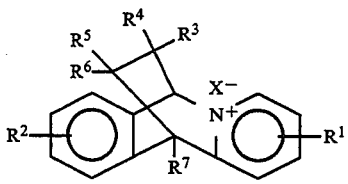

wherein:

R$^1$ is hydrogen, or from one to four, the same or different, substituents in any of the 1-, 2-, 3-, or 4-positions selected from the group consisting of lower-alkoxy, lower-alkyl and halogen;

R$^2$ is hydrogen, or from one to four, the same or different, substituents in any of the 7-, 8-, 9-, or 10-positions selected from the group consisting of lower-alkyl, lower-alkanoyloxy, halogen, nitro, hydroxy, lower-alkoxy, methylenedioxy, polyfluorolower-alkyl, and polychlorolower-alkyl;

R$^3$ and R$^4$ are independently selected from the group consisting of hydrogen, lower-alkoxy, halogen, lower-alkyl, and phenyl;

R$^5$ and R$^6$ are independently selected from the group consisting of hydrogen, lower-alkoxy, trilower-alkylsilyloxy and dilower-alkylamino; or R$^5$ and R$^6$ together represent —O—CHR$^8$(CH$_2$)$_n$CHR$^9$—O— wherein n is zero or one and R$^8$ and R$^9$ are independently hydrogen, lower-alkyl, or phenyl-lower-alkoxy-lower-alkyl;

R$^7$ is hydrogen, or lower-alkyl; and

X$^-$ is an anion;

or a pharmaceutically acceptable acid-addition salt of basic members thereof; or a hydrate thereof; or a stereoisomer thereof; with the proviso that when R$^1$, R$^3$, R$^4$ and R$^7$ are hydrogen, R$^5$ and R$^6$ are ethoxy and X$^-$ is ClO$_4^-$, R$^2$ cannot be 7,10-diacetoxy or 7-acetoxy-10-tert-butyl; further provided that when R$^1$, R$^2$ and R$^7$ R$^3$ and R$^4$ are methyl and X$^-$ is ClO$_4^-$, R$^5$ and R$^6$ are hydrogen, together cannot be —O—CH(CH$_3$)CH(CH$_3$)—O—; still further provided that when R$^1$, R$^4$, R$^5$ and R$^7$ are hydrogen, R$^3$ and R$^6$ are ethoxy and X$^-$ is ClO$_4^-$, R$^2$ cannot be 7—NO$_2$; still further provided that R$^5$ and R$^6$ cannot both simultaneously be hydrogen.

35. A method according to claim 34 wherein:

R$^1$ is hydrogen, or one substituent in any of the 1-, 2-, 3-, or 4-positions selected from the group consisting of lower-alkoxy, and lower-alkyl; and R$^2$ is hydrogen, or from one to two, the same or different, substituents in any of the 7-, 8-, 9-, or 10-positions selected from the group consisting of lower-alkyl, lower-alkanoyloxy, halogen, nitro, hydroxy, lower-alkoxy, methylenedioxy, and polyfluorolower-alkyl.

36. A method according to claim 35 wherein:

R$^1$ is hydrogen, 1-lower-alkoxy, or 4-lower-alkyl; and

R$^2$ is hydrogen, or from one to two, the same or different, substituents in any of the 7-, 8-, 9-, or 10-positions selected from the group consisting of lower-alkyl, acetoxy, halogen, nitro, hydroxy, lower-alkoxy, methylenedioxy, and trifluoromethyl.

37. A method according to claim 36 wherein:

R$^1$ is hydrogen, 1-methoxy, or 4-methyl; and

R$^2$ is hydrogen, or from one to two, the same or different, substituents in any of the 7-, 8-, 9-, or 10-positions selected from the group consisting of methyl, tert-butyl, acetoxy, bromine, chlorine, fluorine, nitro, hydroxy, methoxy, isopropoxy, methylenedioxy and trifluoromethyl.

38. A method according to claim 37 wherein R$^3$ and R$^4$ are independently selected from the group consisting of hydrogen, ethoxy, bromine, chlorine, methyl, ethyl and phenyl; and R$^7$ is hydrogen or methyl.

39. A method according to claim 38 wherein R$^5$ and R$^6$ are independently selected from the group consisting of hydrogen, methoxy, ethoxy, propoxy, trimethylsilyloxy, and diethylamino; or R$^5$ and R$^6$ together represent —OCHR$^8$(CH$_2$)$_n$CHR$^9$—O— wherein n is zero or one and R$^8$ and R$^9$ are simultaneously hydrogen, methyl, or phenylmethoxymethyl.

40. A method according to claim 37 wherein R$^3$ and R$^4$ are the same lower-alkyl.

41. A method according to claim 40 wherein R$^3$ and R$^4$ are both methyl, or ethyl, and R$^7$ is hydrogen, or methyl.

42. A method according to claim 41 wherein:

R$^5$ and R$^6$ are independently selected from the group consisting of hydrogen, methoxy, ethoxy, propoxy, trimethylsilyloxy, and diethylamino; or R$^5$ and R$^6$ together represent —OCHR$^5$(CH$_2$)$_n$CHR$^9$—O— wherein n is zero or one and R$^8$ and R$^9$ are simultaneously hydrogen, methyl, or phenylmethoxymethyl.

43. A method according to claim 42 wherein the compound is 9-methoxy-12,12-diethoxy-13,13-dimethyl-6,11-ethano-6,11-dihydrobenzo[b]quinolizinium·PF$_6^-$.

44. A method according to claim 42 wherein the compound is 10-methoxy-12,12-diethoxy-13,13-dimethyl-6,11-ethano-6,11-dihydrobenzo[b]quinolizinium chloride.

45. A method according to claim 42 wherein the compound is (−)-12,12-diethoxy-13,13-dimethyl-6,11-ethano-6,11-dihydrobenzo[b]quinolizinium chloride.

46. A method according to claim 34 for the treatment or prevention of neurodegenerative disorders.

47. A method according to claim 34 for the treatment or prevention of neurotoxic injuries.

48. A method according to claim 47 wherein said neurotoxic injuries are associated with ischemic, hypoxic, or hypoglycemic conditions.

49. A method according to claim 48 wherein said ischemic, hypoxic, or hypoglycemic conditions are associated with stroke.

* * * * *